United States Patent [19]

Natsugari et al.

[11] Patent Number: 4,851,422
[45] Date of Patent: Jul. 25, 1989

[54] ANTIBIOTIC 2-(3-OXO-2-ISOXAZOLIDINYL)-5-OXO-2-TETRAHYDROFURAN-CARBOXYLATES

[75] Inventors: Hideaki Natsugari, Ashiya; Yasuhiko Kawano, Suita; Akira Morimoto, Ikeda; Kouichi Yoshioka, Kyoto, all of Japan

[73] Assignee: Takeda Chemical Industries, Ltd., Osaka, Japan

[21] Appl. No.: 857,834

[22] Filed: Apr. 30, 1986

[30] Foreign Application Priority Data

Apr. 30, 1985 [WO] PCT Int'l Appl. ... PCT/JP85/00247
Jul. 12, 1985 [WO] PCT Int'l Appl. ... PCT/JP85/00394
Dec. 16, 1985 [JP] Japan ........................ 284154
Mar. 20, 1986 [JP] Japan ........................ 63735

[51] Int. Cl.⁴ ............... A61K 31/42; C07D 407/14
[52] U.S. Cl. ............... 514/370; 514/212; 514/241; 514/252; 514/255; 514/256; 514/371; 514/380; 540/603; 544/216; 544/238; 544/333; 544/367; 544/405; 546/209; 546/275; 548/110; 548/115; 548/127; 548/128; 548/131; 548/134; 548/136; 548/143; 548/184; 548/185; 548/195; 548/196; 548/200; 548/214; 548/235; 548/238

[58] Field of Search ............... 548/243, 244, 184, 185, 548/115, 110, 127, 128, 131, 134, 136, 143, 200, 214, 235, 238, 195; 514/380, 370, 371, 212, 241, 252, 255, 256, 365; 544/238, 333, 367, 405, 216; 540/603; 546/275, 209

[56] References Cited

U.S. PATENT DOCUMENTS 4,546,101 10/1985 Takaya et al. ........................ 540/222
4,560,508 12/1985 Matsuo et al. ........................ 540/200
4,595,532 6/1986 Miller ........................ 540/200
4,619,787 10/1986 Götschi et al. ........................ 540/200
4,656,288 4/1987 Ono et al. ........................ 548/244

FOREIGN PATENT DOCUMENTS 1768114 10/1971 Fed. Rep. of Germany .
4073772 6/1979 Japan ........................ 548/243
4073775 6/1979 Japan ........................ 548/243
57-179133 11/1982 Japan .

1199547 7/1970 United Kingdom .

OTHER PUBLICATIONS

Vasella, Chemical Abstracts, vol. 87, No. 9 (1977), Abstract No. 68562M.
Vasella, Chemical Abstracts, vol. 87, No. 15 (1977), Abstract No. 118030j.
Vasella, Chemical Abstracts, vol. 95, No. 7 (1981), Abstract No. 62045p.
Vasella, Chemical Abstracts, vol. 98, No. 17 (1983), Abstract No. 143737e.
Vasella, Chemical Abstracts, vol. 99, No. 19 (1983), Abstract No. 158804u.
Tsuji et al., Heterocycles, vol. 8, 1977, pp. 153–157.
Yoshioka et al., CA 106-4760c.
Yoshioka et al., CA 106-119555g.
Natsujari et al., CA 106-196437x.
Nozaki et al., CA 106-116365j.
Chang, CA96-19.

Primary Examiner—Cecelia Shen
Attorney, Agent, or Firm—Wenderoth, Lind & Ponack

[57] ABSTRACT

The compound represented by the formula:

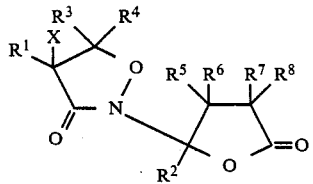

where $R^1$ stands for amino or an organic residue bonded through nitrogen; $R^2$ stands for carboxyl or a group derivable therefrom; $R^3$, $R^4$, $R^5$, $R^6$, $R^7$ and $R^8$ independently stand for hydrogen or an organic residue, including the case where $R^5$ or $R^6$ forms a chemical bond or a ring with $R^7$ or $R^8$; X stands for hydrogen, methoxy or formylamino; or a salt thereof, produceable by the present method, exhibits excellent antimicrobial activity, and is utilized as antimicrobial agents.

28 Claims, No Drawings

ANTIBIOTIC 2-(3-OXO-2-ISOXAZOLIDINYL)-5-OXO-2-TETRAHYDROFURAN-CARBOXYLATES

This invention relates to novel 2-(4-substituted amino3-oxo-2-isoxazolidinyl)-5-oxo-2-tetrahydrofurancarboxylic acid derivates exhibiting excellent antimicrobial activities and to process for production thereof.

Recently, a novel antibiotic TAN-588 (hereinafter referred to in some instances briefly as "TAN-588") exhibiting antimicrobial activity against gram-positive and gram-negative bacteria has been harvested from microorganisms belonging to the genera Empedobacter and Lysobacter which are isolated from soil.

The antibiotic TAN-588 has quite a new skeleton of a 3-oxoisoxazolidine ring having 5-oxo-2-tetrahydrofurancarboxylic acid bonded at its nitrogen atom.

The present inventors synthesized derivatives of the antibiotic TAN-588 and found that these derivatives possess excellent antimicrobial activity and are utilizable as an antimicrobial agent.

Heretofore, there has been reported a synthesis of a compound of a 3-oxoisoxazolidine ring having a 1-methylacetic acid group introduced at its nitrogen atom [Tsuji and Yamana; Heterocycles, 8, 153 (1977)]. However, it has been reported that the compound having the said 1-methylacetic acid group was not observed to exhibit antimicrobial activity.

The present invention aims at production of novel 2-(4-substituted amino-3-oxo-2-isoxazolidinyl)-5-oxo-2-tetrahydrofurancarboxylic acid derivatives which are observed to exhibit useful antimicrobial activity.

By further study and researches, the present inventors found that 2-(4-substituted amino-3-oxo-2-isoxazolidinyl)-5-oxo-2-tetrahydrofurancarboxylic acid derivatives optionally having substituents at 5-position of the 3-oxoisoxazolidine ring, or 3- or 4-position of the 5-oxotetrahydrofuran ring can be synthesized chemically. The finding was followed by further research, leading to the completion of this invention. The present invention is concerned with:

(1) A compound represented by the formula:

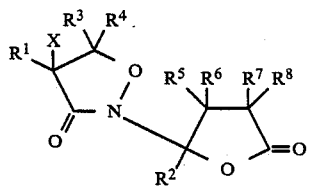

wherein $R^1$ stands for amino or an organic residue bonded through nitrogen; $R^2$ stands for carboxyl or a group derivable therefrom; $R^3$, $R^4$, $R^5$, $R^6$, $R^7$ and $R^8$ independently stand for hydrogen or an organic residue, including the cases where $R^5$ or $R^6$ forms a chemical bond or a ring with $R^7$ or $R^8$; X stands for hydrogen, methoxy or formylamino; provided that all of $R^3$, $R^4$, $R^5$, $R^6$, $R^7$ and $R^8$ are not hydrogen simultaneously; or a salt thereof, (2) a process for producing a compound represented by the formula;

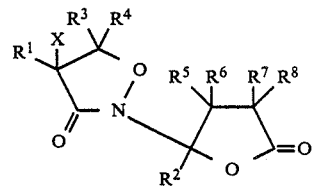

wherein $R^1$, $R^2$, $R^3$, $R^4$, $R^5$, $R^6$, $R^7$, $R^8$ and X are as defined above, including the case where all of $R^3$, $R^4$, $R^5$, $R^6$, $R^7$ and $R^8$ are hydrogen simultaneously, which comprises allowing a compound represented by the formula:

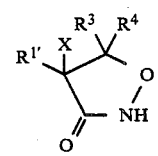

wherein $R^{1'}$ stands for an organic residue bonded through nitrogen; $R^3$, $R^4$ and X are defined above, including the case where $R^3$ and $R^4$ are hydrogen simultaneously to react with a compound represented by the formula:

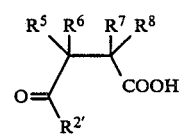

wherein $R^{2'}$ stands for a group derivable from carboxyl group; $R^5$, $R^6$, $R^7$ and $R^8$ are as defined above, including the case where all of $R^5$, $R^6$, $R^7$ and $R^8$ are hydrogen simultaneously, or a reactive derivative thereof, followed by, when necessary, subjecting the resultant compound to modification by $R^{1'}$ and/or $R^{2'}$, (3) a process for producing a compound (I'), which comprises allowing a compound (III) to react with a compound represented by the formula:

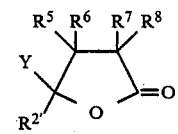

wherein Y stands for a leaving group, and $R^{2'}$, $R^5$, $R^6$, $R^7$ and $R^8$ are as defined above, including the case where all of $R^5$, $R^6$, $R^7$ and $R^8$ are hydrogen simultaneously, followed by, when necessary, subjecting the resultant compound to modification of $R^{1'}$ and/or $R^{2'}$, (4) a compound represented by the formula:

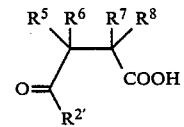

wherein $R^{2'}$, $R^5$, $R^6$, $R^7$ and $R^8$ are as defined above, including the case where all of $R^5$, $R^6$, $R^7$ and $R^8$ are hydrogen simultaneously, provided that, when all of $R^5$, $R^6$, $R^7$ and $R^8$ are hydrogen simultaneously, $R^{2'}$ is not ethoxycarbonyl, (5) a compound (IV), and (6) an antibiotic agent containing a compound (I) or a salt thereof.

The organic residue bonded through nitrogen, representable by $R^1$ or $R^{1'}$ in the above formulae, is exemplified by acylamino, a substituted amino through carbon, alkenylamino, thioamino, silylamino, phosphonoamino and a group including a group representable by the formula: —CO—CO—NH—.

The acyl in the above acylamino includes, for example, the conventionally known acyl groups, such as acyl groups being substituted in the 6-amino group of penicillin derivatives and acyl groups being substituted in the 7-amino group of cephalosporin derivatives.

Examples of the said acylamino group include groups of the formula:

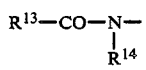

wherein $R^{13}$ stands for hydrogen, alkyl* (in the descriptions for each of the groups as used in the present specification, the groups bearing the mark "*" designate that they may have a substituent or subsituents), alkenyl*, cycloalkyl*, aryl*, heterocyclic ring*, alkoxy* or aryloxy*; $R^{14}$ stands for hydrogen or alkyl*, including the case where $R^{13}$ forms a ring* with $R^{14}$; groups of the formula:

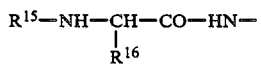

wherein $R^{15}$ stands for hydrogen, amino acid residue*, amino-protecting group or a group represented by the formula: $R^{17}$—$(CH_2)_n$—C(=Z)—{wherein $R^{17}$ stands for a heterocyclic ring*, alkoxy* or amino*; n is 0, 1 or 2; Z stands for O or S}; and $R^{16}$ stands for alkyl*, aryl*, cycloalkenyl* or heterocyclic ring*; groups of the formula.

wherein $R^{18}$ stands for a group represented by the formula;

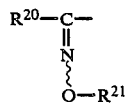

{wherein $R^{20}$ stands for alkyl*, heterocyclic ring* or aryl*; $R^{21}$ stands for hydrogen, alkyl*, alkenyl*, cycloalkyl*, heterocyclic ring*, or a group represented by the formula: —$R^{22}$—$R^{23}$ (wherein $R^{22}$ stands for alkylene*, cycloalkylene or alkenylene; $R^{23}$ stands for aryl*, carboxy* or its ester or mono- or dialkylamido) ; $R^{19}$ stands for a chemical bond or a group represented by the formula;

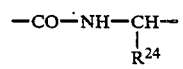

where $R^{24}$ stands for alkyl*, aryl* or heterocyclic ring*); groups of the formula:

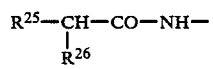

wherein $R^{25}$ stands for aryl*, heterocyclic ring* or cycloalkenyl*; $R^{26}$ stands for hydroxyl, sulfamoyl, sulfo, sulfoxy or acyloxy*}; groups of the formula:

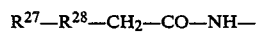

wherein $R^{27}$ stands for alkyl*, cyano, aryl*, aryloxy*, alkenylene*, heterocyclic ring*, amino* or a group represented by the formula; $R^{27'}$—C(=S)— (wherein $R^{27'}$ stands for alkoxy); $R^{28}$ stands for chemical bond or —S—; and groups of the formula:

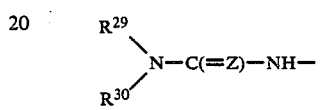

wherein $R^{29}$ and $R^{30}$ independently stand for hydrogen, alkyl*, aryl*, heterocyclic ring* or cycloalkyl; Z stand for O or S. The formula

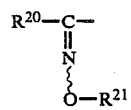

in the group $R^{18}$ represents the syn isomer represented by the formula:

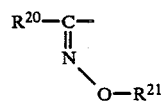

and the anti isomer represented by the formula:

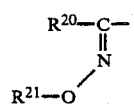

or a mixture therof.

Examples of the amino being substituted through carbon which exemplifies the organic residue bonded through nitrogen as represented by the above $R^1$ or $R^{1'}$ include groups of the formula:

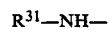

wherein $R^{31}$ stands for alkyl*, aryl*, alkenyl* or heterocyclic ring*; groups of the formula:

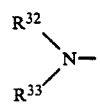

wherein $R^{32}$ and $R^{33}$ independently stand for alkyl*, aryl* or alkenyl*, including the case where $R^{32}$ and $R^{33}$ form a heterocyclic ring* cooperating with the adjacent nitrogen atom; and groups of the formula:

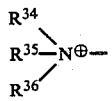

wherein $R^{34}$, $R^{35}$ and $R^{36}$ independently stand for alkyl*, aryl* or alkenyl*, and also $R^{34}$ and $R^{35}$ or $R^{36}$ cooperate with the adjacent nitrogen atom to form a hetercyclic ring*.

Examples of the alkenylamino which exemplifies the organic residue bonded through nitrogen as represented by the above $R^1$ or $R^{1\prime}$ include, for example, groups of the formula:

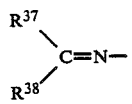

wherein $R^{37}$ and $R^{38}$ independently stand for hydrogen, alkyl*, aryl*, cycloalkyl, amino* or heterocyclic ring*, including the case where $R^{37}$ and $R^{38}$ form cycloalkyl* or heterocyclic ring* cooperating with the adjacent carbon atom.

Examples of the thioamino which exemplifies the organic residue bonded through nitrogen as represented by the above $R^1$ or $R^{1\prime}$ include groups of the formula:

$$R^{39}-SO_n-NH-$$

wherein $R^{39}$ stands for alkyl* or aryl*; n denotes 0, 1 or 2.

Examples of the silylamino which exemplifies the organic residue bonded through nitrogen as represented by the above $R^1$ or $R^{1\prime}$ include groups of the formula:

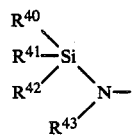

wherein $R^{40}$, $R^{41}$ and $R^{42}$ independently stand for alkyl* or aryl*, and also they form a cyclic group; $R^{43}$ stands for hydrogen or silyl*.

Examples of the phosphonoamino which exemplifies the organic residue bonded through nitrogen as represented by the above $R^1$ or $R^{1\prime}$ include groups of the formula:

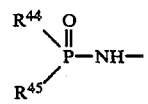

where $R^{44}$ and $R^{45}$ independently stand for alkyl*, aryl*, alkoxy* or aryloxy*, including the case where they form a heterocyclic ring*.

Examples of the groups of the formula: —CO—CO—NH— exemplified as the organic residue bonded through nitrogen represented by the above $R^1$ or $R^{1\prime}$ include groups of the formula:

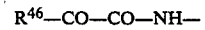

$$R^{46}-CO-CO-NH-$$

wherein $R^{46}$ stands for hydrogen, alkyl*, alkoxy*, aryl*, aryloxy*, heterocyclic ring* or amino*.

In the above formulae, the organic residue bonded through nitrogen as represented by $R^1$ or $R^{1\prime}$ is preferably of a molecular weight up to 500.

In the above formulae, the group derivable from carboxyl as represented by $R^2$ or $R^{2\prime}$ is exemplified by groups of the formula:

$$-COOR^{47}$$

wherein $R^{47}$ stands for alkyl*, alkenyl*, aryl*, cycloalkyl*, heterocyclic ring* or silyl, and groups of the formula;

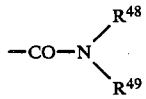

wherein $R^{48}$ and $R^{49}$ independently stand for hydrogen, alkyl*, aryl*, cycloalkyl*, alkenyl* or heterocyclic ring*, including the case where $R^{48}$ and $R^{49}$ form a heterocyclic ring* cooperating with the adjacent nitrogen atom.

In the above formulae, the group derivable from carboxyl as represented by $R^2$ or $R^{2\prime}$ is preferably of a molecular weight up to 500.

In the above formulae, the alkyl is preferably those, for example, of 1 to 6 carbon atoms, as exemplified by methyl, ethyl, n-propyl, isopropyl, n-butyl, isobutyl, sec-butyl, t-butyl, 1,1-dimethylpropyl, n-pentyl, isopentyl, n-hexyl and isohexyl.

The substituent group which the said alkyls may have includes, for example, halogen, oxo, thioxo, nitro, amino (which may have as a substituent alkyl, alkenyl, cycloalkyl, aryl, acyl, carbamoyl or N-sulfocarbamoyl), sulfo, cyano, hydroxy, carboxy (which may be esterified with alkyl), cycloalkyl, cycloalkenyl, alkoxy (which may have as a substituent amino, hydroxy, carboxy, halogen, aryl, cycloalkyl or alkoxy), aryl (which may have as a substituent halogen, alkyl, alkoxy, alkylamino, amino, carbamoyl, sulfo, alkylsulfonyl, cyano, hydroxy, carboxy, nitro, acyloxy, aralkyloxy, or sulfoxy), arylcarbonyl which may have substituents similar to those mentioned above for aryl, aryloxy which may have substituents similar to those mentioned above for aryl, heterocyclic ring (which may have as a substituent nitro, oxo, aryl, alkenylene, halogenoalkyl, alkylsulfonyl, alkyl, alkoxy, alkylamino, amino, halogen, carbamoyl, hydroxy, cyano, carboxy or sulfo), acyl (which may have as a substituent arylcarbonylhydrazino which may as a substituent hydroxy, halogen, amino or nitro), acyloxy, alkoxycarbonyl, alkoxycarbonyloxy (which may have as a substituent halogen), acyloxy-ethoxy, aralkyl (which may have as a substituent alkyl, alkoxy, halogen, amino, hydroxy, nitro, cyano, carbamoyl or sulfamoyl), aralkyloxy (which may have as a substituent acyloxy, alkyl, alkoxy, halogen, amino, hydroxy, nitro, cyano, carbamoyl or sulfamoyl), hydroxysulfonyloxy, alkylsulfonyloxy, arylsulfonyloxy, alkylsulfonyl, aminosulfonyl, alkylsulfinyl, arylsulfonyl, alkylsulfinyl, alkylthio (which may have as a substituent cyano, halogen, carboxyl, alkylamino, imino, carbamoyl or acylamino), arylthio, heterocyclic ring-thio (which may have as a substituent cyano, hydroxy, amino, alkylamino, alkyl, halogen or oxo), heterocyclic ring (which may have as a substituent cyano, hydroxy, amino, alkylamino, alkyl, halogen or oxo)-alkyl-thio, iminomethylamino, iminoethylamino, silyl (which may have alkyl or aryl as a substituent), alkyloxycarbonyl, arylcarbonyl (which may have as a substituent acyloxy, halogen, amino, hydroxy, alkoxy, or sulfamoyl), phthalimido, succinimido, dialkylamino, dialkylaminocarbonyl, arylcarbonylamino, carbamoyl, carbamoyloxy, N-sulfocarbamoyloxy, alkylcarbonylcarbamoyloxy (which may have as a substituent halogen), alkoxyimino, and groups of the formula:

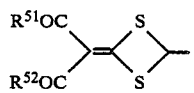

wherein $R^{51}$ and $R^{52}$ are the same or different and represent independently a hydroxyl or amino group.

In the above formulae, the alkylene as represented by $R^{22}$ is preferably, for example those of 1 to 6 carbon atoms, and their examples include, for example, methylene, ethylene, trimethylene, tetramethylene, pentamethylene and hexamethylene.

The substituent which the said alkylene group may have includes, for example, halogen, amino, hydroxy, alkoxy, carboxy, carbamoyl, cyano and nitro.

In the above formulae, the cycloalkyl, the cycloalkyl in cycloalkyloxy and the cycloalkyl forming a ring are desirably those of 3 to 8 carbon atoms, and their examples include, for example, cyclopropyl, cyclobutyl, cyclopentyl, cyclohexyl, cycloheptyl and cyclooctyl.

The substituent group which the said cycloalkyl groups may have includes, for example, halogen, nitro, amino, hydroxy, sulfo, cyano, carboxy, oxo and thioxo.

The cycloalkylene in the groups of the above formulae includes, for example, those consisting of the above cycloalkyl being provided with additional bond.

In the groups of the above formulae, the aryl in the aryl, arylcarbonyl, aryloxycarbonyl, aryloxy or arylthio includes, for example, phenyl, naphthyl, biphenyl, anthryl and indenyl.

The substituent which the said aryl group may have includes, for example, halogen, nitro, cyano, amino (which may have as a substituent alkyl, alkenyl, cycloalkyl or aryl), sulfo, mercapto, hydroxy, carboxy, acyl, sulfoxy, sulfamoyl, carbamoyl, alkyl (which may have as a substituent amino, halogen, hydroxy, cyano or carboxy), alkoxy, aralkyloxy, alkylsulfonamido, methylenedioxy, alkylsulfonyl and alkylsulfonylamino. Also, they, together with cycloalkyl, may form a fused ring (e.g., tetrahydronaphthyl, indanyl, acenaphthyl, etc.).

In the above formulae, the alkoxy is desirably those of 1 to 6 carbon atoms, and their examples include, methoxy, ethoxy, n-propoxy, isopropoxy, n-butoxy, isobutoxy, t-butoxy, n-pentyloxy and n-hexyloxy.

The substituent, which the said alkoxy group may have, includes, for example, halogen, nitro, amino, hydroxy, sulfo, cyano, carboxy, aryl (which may have as a substituent nitro, amino, hydroxy, alkyl or alkoxy) and silyl (which may have as a substituent alkyl, aryl or aralkyl).

In the above formulae, the alkylthio is preferably those of 1 to 6 carbon atoms, and is exemplified by methylthio, ethylthio, n-propylthio, isopropylthio, n-butylthio, isobutylthio, n-pentylthio and n-hexylthio. The substituent, which the said alkylthio group may have include those analogous to the substituents of the above-mentioned alkoxy.

In the groups of the above formulae, the alkenyl is preferably, for example, those of 1 to 6 carbon atoms, and their examples include, methylene, vinyl, allyl, isopropenyl, 1-propenyl, 2-butenyl, 3-methyl-3-butenyl, 1,3-butadienyl, 1,3-pentadienyl, 4-pentaenyl, 1,3-hexadienyl, ethylidene, propylidene, isopropylidene and butylidene.

The substituent which the said alkenyl group may have includes, for example, halogen, nitro, amino (which may have acyl as a substituent), sulfo, cyano, hydroxy, carboxy, carbamoyl, sulfamoyl, aryl and acyl.

In the groups of the above formulae, the alkenylene is preferably, for example, those of 2 to 6 carbon atoms, and their examples include, vinylene, 1-propenylene, 2-butenylene, 2-pentenylene and 1,3-hexadienylene.

The substituent which the said alkenylene group may have includes, for example, halogen, cyano and carbamoyl.

In the above formulae, the cycloalkenyl represented by $R^{16}$ $R^{15}$ is preferably those of 3 to 8 carbon atoms, and their examples include, for example, 1-cyclopropenyl, 1-cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl and 1,4-cyclohexadienyl. The substituent which the said cycloalkenyl groups may have include, for example, halogen, nitro, amino, sulfo, cyano, hydroxy, carboxy, carbamoyl and sulfamoyl.

In the groups of the above formulae, the heterocyclic ring or the heterocyclic ring formed by these groups includes, for example, 5-membered to 7-memebered heterocyclic groups containing a sulfur, nitrogen or oxygen atom, 5-membered to 6-membered heterocyclic groups containing 2 to 4 nitrogen atoms, and 5-membered to 6-membered heterocyclic groups containing 1 to 2 nitrogen atoms and a sulfur or oxygen atom, whereby these heterocyclic groups may be fused to a six-membered cyclic group containing not more than 2 nitrogen atoms, benzene ring or five-membered cyclic group containing a sulfur atom.

Specific examples of the above heterocyclic groups include 2-pyridyl, 3-pyridyl, 4-pyridyl, pyrimidinyl, pyrazinyl, pyridazinyl, piperazinyl, piperidyl, pyrazolyl, pyranyl, thiopyranyl, pyrimidyl, imidazolyl, thiazolyl, isothiazolyl, oxazolyl, isoxazolyl, pyrido[2,3-d]pyrimidyl, benzopyranyl, 1,8-naphthylidyl, 1,5-naphthylidyl, 1,6-naphthylidyl, 1,7-naphthylidyl 2,7-naphthylidyl, 2,6-naphthylidyl, quinolyl, thieno [2,3-b]-pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, hexahydro-1H-azepinyl, indolyl, isoindolyl and chromanyl.

The substituent which the said heterocyclic groups may have includes, for example, amino (which may have as a substituent acyl, halogen-substituted alkylacyl, phenyl or alkyl), helogen, nitro, sulfo, cyano, hydroxy, carboxy, oxo, thioxo, $C_{1-10}$-alkyl [which may have as a substituent aryl, halogen, amino, hydroxy, carboxy, alkoxy, alkylsulfonyl, dialkylamino or phosphono (which may have alkyl as a substituent)], cycloalkyl, alkoxy (which may have as a substituent halogen or hydroxy), acyl of 1 to 4 carbon atoms, aryl (which may have as a substituent halogen, nitro, alkyl, alkoxy, amino, sulfo, hydroxy or cyano), oxo, thioxo, amino acid residue-thio (examples of the amino acid residue include residues similar to those to be mentioned below), $C_{1-10}$-alkyl-thio [which may have as a substituent aryl, halogen, amino, hydroxy, carboxy, alkoxy, alkylsulfonyl, dialkylamino, or phosphono (which may have alkyl as a substituent)], heterocyclic rings (which may have as a substituent alkyl, alkoxy, halogen, nitro, cyano, carboxy, formyl or alkylsulfonyl) and groups of the formula $R^{53}$—CH=N—[wherein $R^{53}$ include heterocyclic ring (which may have alkyl, alkoxy, halogen, nitro, cyano, hydroxy, carboxy, formyl or alkylsulfonyl as a substituent)].

In the above formulae, the cyclic group represented by $R^{14}$ which is formed with $R^{13}$, includes cyclic groups which have, for example, phthaloyl, succinyl, maleoyl, citraconoyl, glutaryl, and adipoyl, and furthermore, 2,2-dimethyl-5-oxo-4-phenyl-imidazolidine. The substituent which the said cyclic groups may have includes, for example, halogen, nitro, amino, hydroxy, sulfo, cyano, and carboxy.

In the above formulae, the acyl in the acyloxy and the acyl in $R^{3-8,10,11}$ are preferably those of 1 to 4 carbon atoms, and their examples include formyl, acetyl, propionyl, butyryl and isobutyryl, and substituent groups for them include, for example, alkyl (which may have as a substituent amino, halogen, cyano, alkoxy, carboxy or hydroxy).

In the above formulae, the amino acid residue as represented by $R^{15}$ includes, for example, glycyl, alanyl, valyl, leucyl, isoleucyl, seryl, threonyl, cysteinyl, cystyl, methionyl, α- or β-aspargyl, α- or γ-glutamyl, lysyl, arginyl, phenylalanyl, phenylglycyl, thyrosyl, histidyl, tryptophanyl, and prolyl.

The substituent group which the said amino acid residue may have includes, for example, halogen, hydroxy, sulfo, carboxy, cyano, alkylamino, aralkyloxycarbonyl, aralkyloxy and guanidino.

In the above formulae, as a protective group for the amino group as represented by $R^{15}$, there are suitably used those to be used for this purpose in the fields of for example β-lactam and peptide synthesis. Their examples include aromatic acyl groups, such as phthaloyl, 4-nitrobenzoyl, 4-t-butylbenzoyl, 4-t-butylbenzenesulfonyl, benzenesulfonyl and toluenesulfonyl; aliphatic acyl groups, such as formyl, acetyl, propionyl, monochloroacetyl, dichloroacetyl, trichloroacetyl, methanesulfonyl, ethanesulfonyl, trifluoroacetyl, malonyl and succinyl; esterified carboxyl groups, such as methoxycarbonyl, ethoxycarbonyl, t-butoxycarbonyl, isopropoxycarbonyl, 2-cyanoethoxycarbonyl, 2,2,2-trichloroethoxycarbonyl, benzyloxycarbonyl, 4-nitrobenzoyloxycarbonyl, 4-methoxybenzyloxycarbonyl, diphenylmethyloxycarbonyl, methoxymethyloxycarbonyl, acetylmethyloxycarbonyl, isobornyloxycarbonyl, phenyloxycarbonyl; methylene groups, such as (hexahydro-1H-azepin-1-yl)methylene; sulfonyl groups, such as 2-amino-2-carboxyethylsulfonyl; and amino-protecting groups other than acyl groups, such as trityl, 2-nitrophenylthio, benzylidene, 4-nitrobenzylidene, di- or trialkylsilyl, benzyl and 4-nitrobenzyl. Selection of the said protective groups is not limited in this invention, but among others, monochloroacetyl, benzyloxycarbonyl, 4-methobenzyloxycarbonyl and 4-nitrobenzyloxycarbonyl are preferable.

In the above formulae, the substituent group in the carboxy group which may have a substituent includes, for example, alkyl (which may have as a substituent halogen, cyano or hydroxy), aryl (which may have as a substituent alkyl, alkoxy, halogen, hydroxy, acyloxy, sulfo, cyano or sulfamoyl), silyl (which may have as a substituent alkyl, aryl or aralkyl), heterocyclic rings (which may have as a substituent amino, alkylamino, sulfamoyl, carbamoyl, halogen, cyano or nitro) and amino (which may have as a substituent alkyl, aryl, cycloalkyl, sulfo or aralkyl, and which may form 5-membered to 6-membered heterocyclic ring together with the nitrogen in the said amino group).

In the above formulae, the ester group in the ester of carboxyl represented by $R^{23}$ is preferably those of 1 to 6 carbon atoms, and their examples includes methyl ester, ethyl ester, propyl ester, n-butyl ester, isobutyl ester and t-butyl ester.

In the above formulae, the substituent group in the amino which may have a substituent includes, for example, amidine, iminomethyl, imino-(aryl-substituted)-methyl, guanidylcarbonyl, heterocyclic ring (which may have substituents similar to those mentioned above for the heterocyclic rings), imino-(optionally substituted by heterocyclic ring)-methyl, alkylcarbonyl, arylcarbonyl, hydroxyalkyl and alkyl.

In the above formulae, the substituent group in the silyl which may have a substituent includes, for example, alkyl, aryl and aralkyl.

The above $R^{40}$, $R^{41}$ and $R^{42}$, together with $R^{43}$, may form a cyclic group, and its examples include 2,5-disilylazacyclopentyl and may have substituent groups such as alkyl and aryl.

The halogen in the description of the above substituent groups includes, for example, chlorine, bromine, fluorine and iodine.

The alkyl in the description of the above substituent groups is preferably those of 1 to 10, more preferably those of 1 to 6 or still more preferably those of 1 to 4 carbon atoms, and their examples include methyl, ethyl, n-propyl, isopropyl, n-butyl, isobutyl, t-butyl, sec-butyl, n-pentyl, isopentyl, n-hexyl, isohexyl, heptyl, octyl, nonyl and decyl.

The cycloalkyl as the above substituent group is preferably those of 3 to 6 carbon atoms, and their examples include cyclopropyl, cyclobutyl, cyclopentyl and cyclohexyl.

The alkoxy as the above substituent group is preferably those of 1 to 4 carbon atoms, and their examples include methoxy, ethoxy, n-propoxy, isopropoxy, n-butoxy, isobutoxy and t-butoxy.

The aryl as the above substituent group includes, for example, phenyl and naphthyl.

The heterocyclic ring as the above substituent group includes those similar to the heterocyclic rings mentioned above.

The acyl as the above substituent is preferably those of 1 to 6 carbon atoms, more preferably those of 1 to 4 carbon atoms, and includes, for example, formyl, acetyl, propionyl, butyryl, isobutyryl, valeryl, isovaleryl, pivaloyl and hexanoyl.

The aralkyl as the above substituent group includes, for example, benzyl, phenethyl, and phenyl-propyl.

The alkenyl as the above substituent includes, those similar to the alkenyl mentioned above.

The amino acid residue as the above substituent includes, those similar to the amino acid residues mentioned above for $R^{15}$.

The 5-membered to 6-membered heterocyclic ring formed together with nitrogen in the amino group as the above-mentioned substituent includes, for example, piperidine, pyrrolidine, imidazolidine, morpholine and piperazine.

The substituent groups in each of the above groups exist preferably in number of 1 to 3.

Especially, a group of the formula:

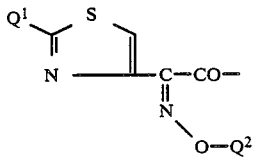

wherein $Q^1$ is amino or a protected amino group, and $Q^2$ is H, alkyl, alkenyl, a group —CH$_2$COOQ$^3$ or a group

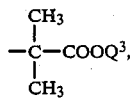

wherein $Q^3$ is H or alkyl*, is more preferably as the acyl moiety of the acylamino for $R^1$. The said alkyl, alkyl* and alkenyl are those mentioned above. The protective group in the said protected amino group includes those mentioned above.

Furthermore, thienylacetyl or phenylacetyl is more preferable as the acyl moiety.

In the above acyl groups, specific examples of the acylamino group as represented by the formula

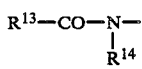

include, for example, 3-(2,6-dichlorophenyl)-5-methylisoxazol-4-yl-carbonyl amino, 4-ethyl-2,3-dioxo-1-piperazino-carbonylamino, 3-phenyl-5-methylisoxazol-4-yl-carbonylamino, 3-(2-chlorophenyl)-5-methylisoxazol-4-yl-carbonylamino, 3-(2-chloro-6-fluorophenyl)-5-methylisoxazol-4-yl-carbonylamino, nicotinylamino, benzoylamino, 4-bromobenzoylamino, 2,6-dimethoxybenzoylamino, formylamino, acetylamino, propionylamino, butyrylamino, isobutyrylamino, pivaloylamino, methoxycarbonylamino, benzyloxycarbonylamino, 1-aminocyclohexylcarbonylamino, 2-aminocyclohexylcarbonylamino, 3-ethoxynaphthylamino, 2-(2-amino-4-thiazolyl)-2-ethylidene-acetylamino, 2-(2-amino-4-thiazolyl)-2-chloromethyleneacetylamino, phthalimido, succinimido, 1,2-cyclohexanedicarboximide, 2-(trimethylsilyl)ethoxycarbonylamino, 2,2-dimethyl-5-oxo-4-phenylimidazolidine and 4-(carbamoylcarboxymethylene) -1,3-dithiethan-2-yl-carbonylamino:

Specific examples of the acylamino group represented by the formula

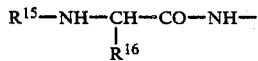

include D-alanylamino, benzyl-N-carbobenzoxy-γ-D-glutamyl-D-alanylamino, D-phenylglycyl-D-alanylamino, N-carbobenzoxy-D-alanylamino, N-carbobenzoxy-D-phenylglycylamino, D-alanyl-D-phenylglycyl-amino, γ-D-glutamyl-D-alanylamino, 2-(4-ethyl-2,3-dioxo-1-piperazinocarboxamido)-2-phenylacetylamino, 2-(4-cyclohexyl-2,3-dioxo-1-piperazinocarboxamido)-2-phenylacetylamino, 2-(4-ethyl-2,3-dioxo-1-piperazinocarboxamido)-2-(4-sulfoxyphenyl)acetyl-amino, N-(4-ethyl-2,3-dioxo-1-piperazinocarbonyl)-D-alanylamino, N-(4-ethyl-2,3-dioxo-1-piperazinocarbonyl)-D-phenylglycylamino, 2-(2-amino-4-thiazolyl)-2-(4-ethyl-2,3-dioxo-1-piperazinocarboxamido)acetylamino, 2-(4-hydroxy-6-methylnicotinamido)-2-phenylacetylamino, 2-(4-hydroxy-6-methylnicotinamido-2-(4-hydroxyphenyl)acetylamino, 2-{5,8-dihydro-2-(4-formyl-1-piperazinyl)-5-oxopyrido[2,3-d]pyrimidine-6-carboxamido}-2-phenylacetylamino, 2-(3,5-dioxo-1,2,4-triazine-6-carboxamido)-2-(4-hydroxyphenyl)acetylamino, 2-(3-furfurylideneamino-2-oxoimidazolidine-1-carboxamido)-2-phenylacetylamino, 2-(coumarin-3-carboxamido)-2-phenylacetylamino, 2-(4-hydroxy-7-methyl-1,8-naphthylidene-3-carboxamido)-2-phenylacetylamino, 2-(4-hydroxy-7-trifluoromethylquinoline-3-carboxamido)-2-phenylacetylamino, N-[2-(2-amino-4-thiazolyl)acetyl]-D-phenylglycylamino, 2-(6-bromo-1-ethyl-1,4-dihydro-4-oxothieno[2,3-b]pyridine-3-carboxamido)-2-phenylacetylamino, 2-(4-ethyl-2,3-dioxo-1-piperazinocarboxamido)-2-thienylacetylamino, 2-(4-n-pentyl-2,3-dioxo-1-piperazinocarboxamido)-2-thienylacetylamino, 2-(4-n-octyl-2,3-dioxo-1-piperazinocarboxamido)-2-thienylacetylamino, 2-(4-cyclohexyl-2,3-dioxo-1-piperazinocarboxamido)-2-thienylacetylamino, 2-[4-(2-phenylethyl)-2,3-dioxo-1-piperazinocarboxamido]-2-thienylacetylamino, 2-(3-methylsulfonyl-2-oxoimidazolidine-1-carboxamido)-2-phenylacetylamino, 2-(3-furfurylideneamino-2-oxoimidazolidine-1-carboxamido)-2-(4-hydroxyphenyl)acetylamino, 2-(4-ethyl-2,3-dioxo-1-piperazinocarboxamido)-2-(4-benzyloxyphenyl)acetylamino, 2-(4-ethyl-2,3-dioxo-1-piperazinocarboxamido)-2-(4-methoxyphenyl)acetylamino, 2-(8-hydroxy-1,5-naphthylidine-7-carboxamido)-2-phenylacetylamino, 2-(2-amino-4-thiazolyl)-2-formamidoacetylamino, 2-(2-amino-4-thiazolyl)-2-acetoamidoacetylamino, 2-phenyl-2-ureidoacetylamino, 2-phenyl-2-sulfoureidoamino, 2-thienyl-2-ureidoacetylamino, 2-amino-3-sulfamoylpropionylamino, 2-amino-2-(1H-indol-3-yl)acetylamino, 2-amino-2-(3-benzo[b]thienyl)acetylamino, 2-amino-2-(2-naphthyl)-acetylamino, D-phenylglycyl, D-2-amino-(4-hydroxyphenyl)-acetylamino, D-2-amino-2-(1,4-cyclohexadienyl)acetylamino, D-2-amino-2-(1-cyclohexenyl)acetylamino, D-2-amino-2-(3-chloro-4-hydroxyphenyl)acetylamino, 2-hydroxymethylamino-2-phenylacetylamino, 2-(1-cyclohexenyl)-2-(4-ethyl-2,3-dioxo-1-piperazinocarboxamido)acetylamino, N-[2-(4-ethyl-2,3-dioxo-1-piperazinocarbonyl)]-D-threonylamino, 2-guanylcarboxamido-2-phenylacetylamino, 2-(4-ethyl-2,3-dioxo-1-piperazinocarboxamido-2-(3,4-dihydroxyphenyl)acetylamino, 2-(4-carboxy-5-imidazolylcarboxamido)-2-phenylacetylamino and 2-amino-2-(3-methyl-sulfonamidophenyl)acetylamino.

Specific examples of the acylamino group represented by the formula $R^{18}$—$R^{19}$—CO—NH— include, for example, N-[2-(2-amino-4-thiazolyl)-2-methoxyiminoacetyl]-D-alanylamino, N-[2-(2-amino-4-thiazolyl)-2-methoxyiminoacetyl]-D-phenylglycylamino, 2-(2-amino-4-thiazolyl)-2-[2-(2-amino-4-thiazolyl)-2-methoxyiminoacetamido]acetylamino, 2-(2-chloroacetamido-4-thiazolyl)-2-methoxyiminoacetylamino, 2-(2-amino-4-thiazolyl)-2-methoxyiminoacetylamino, 2-(2-amino-4-thiazolyl)-2-ethoxyiminoacetylamino, 2-(2-amino-4-thiazolyl)-2-isopropoxyiminoacetylamino, 2-(2-amino-4-thiazolyl)-2- butoxyiminoacetylamino, 2-(2-amino-4-thiazolyl)-2-cyclopropylmethyloxyiminoacetylamino, 2-(2-amino-4-thiazolyl)-2-benzyloxyiminoacetylamino, 2-(2-amino-4-thiazolyl)-2-allyloxyiminoacetylamino, 2-(2-amino-4-thiazolyl)-2-[(1-methyl-1-carboxyethyl)oxyimino]acetylamino, 2-(2-amino-4-thiazolyl)-2-[(1-methyl-1-methoxycarbonylethyl)oxyiminolacetylamino, 2-(2-amino-4-thiazolyl)-2-carboxymethyloxyiminoacetylamino, 2-(2-amino-4-thiazolyl)-2-carboxyvinyloxyiminoacetylamino, 2-(2-amino-4-thiazolyl)-2-carboxyethyloxyiminoacetylamino, 2-(2-amino-4-thiazolyl)-2-methoxycarbonylethyloxyiminoacetylamino, 2-(2-amino-5-chloro-4-thiazolyl)-2-methoxyiminoacetylamino, 2-(2-amino-5-bromo-4-thiazolyl)-2-methoxyiminoacetylamino, 2-(2-amino-4-thiazolyl)-2-oxyiminoacetylamino, 2-thienyl-2-methoxyiminoacetylamino, 2-furyl-2-methoxyiminoacetylamino, 2-(1,2,4-thiadiazol-3-yl)-2-methoxyiminoacetylamino, 2-(1,2,4-thiadiazol-5-yl)-2-methoxyiminoacetylamino, 2-(1,3,4-thiadiazolyl)-2-methoxyiminoacetylamino, 2-(4-hydroxyphenyl)-2-methoxyiminoacetylamino, 2-phenyl-2-methoxyiminoacetylamino, 2-phenyl-2-oxyiminoacetylamino, 2-4-(γ-D-glutamyloxy)phenyl]-2-oxyiminoacetylamino, 2-[4-(3-amino-3-carboxypropoxy)phenyl]-2-oxyiminoacetylamino, 2-thienyl-2-oxyiminoacetylamino, 2-(5-amino-1,2,4-thiadiazol-3-yl)-2-methoxyiminoacetylamino, 2-(5-amino-1,2,4-thiadiazol-3-yl)-2-ethoxyiminoacetylamino, 2-(5-amino-1,2,4-thiadiazol-3-yl)-2-carboxymethyloxyiminoacetylamino, 2-(5-amino-1,2,4-thiadiazol-3-yl)-2-[(1-methyl-1-carboxyethyl)oxyimino]-acetylamino, 2-(2-amino-4-thiazolyl)-2-(2-amino-2-carboxy)-ethyloxyiminoacetylamino, 2-(2-amino-4-thiazolyl)-2-(dimethyl-amidomethyloxyimino)acetylamino, 2-(2-amino-4-thiazolyl)-2-(3,4-diacetoxy-benzoyloxyimino)acetylamino, 2-(2-amino-4-thiazolyl)-2-(1-carboxycyclopropyloxyimino)acetylamino, 2-(2-amino-4-thiazolyl)-2-(1-carboxycyclobutyloxyimino)acetylamino, 2-(2-amino-4-thiazolyl)-2-(2-imidazolylmethyloxyimino)acetylamino, 2-(2-amino-4-thiazolyl)-2-(2-methyl-4-nitro-1-imidazolylethyloxyimino)acetylamino, 2-(2-amino-4-thiazolyl)-2-(3-pyrazolylmethyloxyimino)acetylamino, 2-(2-amino-4-thiazolyl)-2-(1H-tetrazol-5-yl-methyloxyimino)acetylamino, 2-(2-amino-4-thiazolyl)-2-(2-oxo-3-pyrrolidinyloxyimino)acetylamino, 2-[2-(2-amino-2-carboxyethylthio)]-4-thiazolyl-2-methoxyiminoacetylamino, and 2-(2-thioxo-4-thiazolidinyl)-2-methoxyiminoacetylamino.

Specific examples of the acylamino group represented by the formula

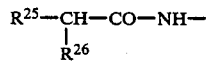

include 2-phenyl-2-sulfo-acetylamino, 2-hydroxy-2-phenylacetylamino, 2-phenyl-2-sulfamoylacetylamino, 2-carboxy-2-phenylacetylamino, 2-(4-hydroxyphenyl)-2-carboxyacetylamino, 2-phenoxycarbonyl-2-phenylacetylamino, 2-phenyl-2-tolyloxycarbonylacetylamino,2-(5-indanyloxycarbonyl)-2-phenylacetylamino, 2-formyloxy-2-phenylacetylamino, 2-alanyloxy-2-phenylacetylamino, 2-carboxy-2-thienylacetylamino, 2-(2-methylphenoxycarbonyl)-2-thienylacetylamino, 2-(2-amino-4-thiazolyl)-2-hydroxyacetylamino and 2-[4-(2-amino-2-carboxyethoxycarboxamido)phenyl]-2-hydroxyacetylamino.

Specific examples of the acylamino group represented by the formula $R^{27}-R^{28}-CH_2-CO-NH-$ include cyanoacetylamino, phenylacetylamino, phenoxyacetylamino, trifluoromethylthioacetylamino, cyanomethylthioacetylamino, difluoromethylthioacetylamino, 1H-tetrazolyl-1-acetylamino, thienylacetylamino, 2-(2-amino-4-thiazolyl)acetylamino, 4-pyridylthioacetylamino, 2-thienylthioacetylamino, 3,5-dichloro-1,4-dihydro-4-oxopyridine-1-acetylamino, β-carboxyvinylthio-acetylamino, 2-(2-aminomethylphenyl)acetylamino, 2-chloroacetylamino, 3-aminopropionylamino, (2-amino-2-carboxy)ethyl-thioacetylamino, 4-amino-3-hydroxybutyrylamino, 2-carboxy-ethylthioacetylamino, 2-benzyloxycarbonylaminoacetylamino, β-carbamoyl-β-fluorovinylthioacetylamino, 2-(1-isopropylamino-1-isopropyliminomethylthio)acetylamino, 2-[1-(2-dimethylamino-ethyl)-1H-tetrazol-5-yl-thio]acetylamino, 2-(1-methyl-1,3,5-triazol-2-yl)acetylamino, and 2-(4-cyano-3-hydroxy-5-isothiazolylthio)acetylamino.

Specific examples of the group represented by the formula

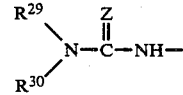

include carbamoylamino, methylaminocarbonylamino, ethylaminocarbonylamino, t-butyl-aminocarbonylamino, isobutylaminocarbonylamino, dimethylaminocarbonylamino, 2-methylphenylaminocarbonylamino, phenylaminocarbonylamino, 3-chlorophenylaminocarbonylamino, 4-nitrophenylaminocarbonylamino, 4-bromophenylaminocarbonylamino, thiocarbamoylamino, methylaminothiocarbonylamino, ethylaminothiocarbonylamino, phenylaminothiocarbonylamino, dimethylaminocarbonylamino and 3-fluorophenylaminocarbonylamino.

Specific examples of the group represented by the formula $R^{31}$-NH- include methylamino, ethylamino, allylamino, cyclohexylamino, cylcohexylmethylamino, benzylamino, 4-chlorobenzylamino, phenylamino, 2-imidazolylamino, 1-methyl-2-imidazolylamino, 2-(2-amino-4-thiazolyl)-2-methoxyiminothioacetylamino, 1-benzyl-4-pyridiniumamino, and 2-acetyl-1-methylvinylamino.

Specific examples of the alkylamino group represented by the formula

include dimethylamino, diethylamino, dipropylamino, dibenzylamino, dicyclohexylamino, N-benzylN-methylamino, diallylamino, N-phenyl-N-methylamino, pyrrolidinyl, piperidinyl, piperazinyl and morpholinyl.

Specific examples of the alkylamino group represented by the formula

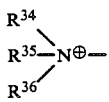

include trimethylammonium, benzyldimethylammonium, methylpyrrolidinium and methylpiperidinium.

Specific examples of the alkenylamino group represented by the formula

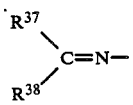

include dimethylaminomethyleneamino, 1-dimethylaminoethylideneamino, hexahydro-1H-azepin-1-ylmethyleneamino, 1-(N-benzyl-N-methylamino)ethylideneamino, 4-dimethylaminobenzylideneamino, (p-nitro)benzylideneamino and benzylideneamino.

Specific examples of the thioamino group represented by the formula $R^{39}-SO_n-NH-$ include benzene-sulfonylamino, 4-methylbenzenesulfonylamino, 4-methoxy-benzenesulfonylamino, 2,4,6-trimethylbenzenesulfonylamino, benzylsulfonylamino, 4-methylbenzylsulfonylamino, trifluoromethylsulfonylamino, phenacylsulfonylamino, methylsulfonylamino, ethylsulfonylamino, 4-fluorobenzenesulfonylamino, benzenesulfinylamino, 2-nitrobenzenesulfinylamino, 2,4-dimethylbenzenesulfinylamino, 4-chlorobenzenesulfinylamino, 4-methoxybenzenesulfinylamino, phenylthioamino, 2,4-dinitrophenylthioamino, triphenylmethylthioamino and 2-nitro-4-methoxyphenylthioamino.

Specific examples of the silylamino group represented by the formula

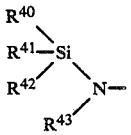

include trimethylsilylamino, triethylsilylamino, t-butyldimethylsilylamino, t-butyldiphenylsilylamino, isopropyldimethylsilylamino, triphenylsilylamino, triisopropylsilylamino, tribenzylsilylamino, (triphenylmethyl)dimethylsilylamino, and 2,2,5,5-tetramethyl-2,5-disilylazacyclopentane.

Specific examples of the group represented by the formula

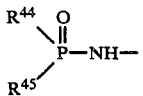

include dimethylphosphoamino, diethylphosphoamino, diphenylphosphoamino, dibenzylphosphoamino, and di-4-chlorophenylphosphoamino.

Specific examples of the group represented by the formula $R^{46}-CO-CO-NH-$ include methoxalylamino, ethoxalylamino, phenoxalylamino, benzyloxalylamino, pyruvoylamino, ethyloxalylamino, oxamoylamino, benzylaminooxalylamino, thienyloxalylamino, 2-amino-4-thiazolyl-oxalylamino and ethyl-aminooxalylamino.

Specific examples of the group represented by the formula $-COOR^{47}$ include methyl ester, ethyl ester, n-propyl ester, isopropyl ester, t-butyl ester, t-amyl ester, benzyl ester, 4-bromobenzyl ester, 4-nitrobenzyl ester, 2-nitrobenzyl ester, 3,5-dinitrobenzyl ester, 4-methoxy-benzyl ester, benzhydryl ester, phenacyl ester, 4-bromo-phenacyl ester, phenyl ester, 4-nitrophenyl ester, methoxy-methyl ester, methoxyethoxymethyl ester, ethoxymethyl ester, benzyloxymethyl ester, acetoxymethyl ester, pivaloyloxymethyl ester, 2-methylsulfonylethyl ester, 2-trimethylsilylethyl ester, methylthiomethyl ester, trityl ester, 2,2,2-trichloroethyl ester, 2-iodoethyl ester, cyclohexyl ester, cyclopentyl ester, allyl ester, cinnamyl ester, 4-picolinyl ester, 2-tetrahydropyranyl ester, 2-tetrahydrofuranyl ester, trimethylsilyl ester, t-butyldimethyl silyl ester, t-butyldiphenylsilyl ester, acetylmethyl ester, 4-nitrobenzoylmethyl ester, 4-mesylbenzoylmethyl ester, phthalimidomethyl ester, propionyloxymethyl ester, 1,1-dimethylpropyl ester, 3-methyl-3-butenyl ester, succinimidomethyl ester, 3,5-di-t-butyl-4-hydroxybenzyl ester, mesylmethyl ester, benzenesulfonylmethyl ester, phenyl-thiomethyl ester, iminomethylaminoethyl ester, 1-iminoethylaminoethyl ester, dimethylaminoethyl ester, pyridine-1-oxido-2-methyl ester, methylsulfinylmethyl ester, bis-(4-methoxy-phenyl)methyl ester, 2-cyano-1,1-dimethylethyl ester, t-butyloxycarbonylmethyl ester, benzoylaminomethyl ester, 1-acetoxyethyl ester, 1-isobutyryloxyethyl ester, 1-ethoxycarbonyloxyethyl ester, phthalide ester, 4-t-butylbenzyl ester, 5-indanyl ester, 5-methyl-2-oxo-1,3-dioxolen-4-yl-methyl ester, and 5-t-butyl-2-oxo-1,3-dioxolen4-yl-methyl ester.

Specific examples of the group represented by the formula

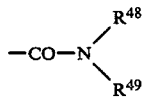

include dimethylamide, diethylamide, dipropylamide, dibenzylamide, dicyclohexylamide, N-benzylN-methylamide, diallylamide, N-phenyl-N-methylamide, pyrrolidineamide, piperidineamide, piperazineamide, morpholineamide, carboxymethylamide and 1-carboxyethylamide.

In the above formulae, as the organic residue represented by $R^3$ and $R^4$ are mentioned those bonded through carbon.

Preferable examples of these organic residue bonded through carbon are alkyl*, cycloalkyl, alkenyl*, aryl*, acyl, cyano, or optionally esterified, or amidated carboxyl.

In the above formulae, as the organic residue represented by $R^5$, $R^6$, $R^7$ and $R^8$ are mentioned those bonded through carbon; those bonded through oxygen, nitrogen or sulfur; or halogen. Preferable examples of the organic residue bonded through carbon are alkyl*, cycloalkyl, alkenyl*, aryl*, acyl, cyano, carbamoyl, heterocyclic ring* or optionally esterified or amidated carboxyl.

Preferable organic residues bonded through oxgen are those represented by the formula; $-O-R^9$ [wherein $R^9$ stands for hydrogen, alkyl, aryl, acyl or carbamoyl] or oxo group.

Preferable organic residues bonded through nitrogen are, for example, those represented by the formula;

[wherein $R^{10}$ and $R^{11}$ independently stand for hydrogen, alkyl, aryl or acyl].

Preferable organic residues bonded through sulfur are, for example, those represented by the formula; $-S(O)_n-R^{12}$ [wherein $R^{12}$ stands for hydrogen, alkyl*, aryl*, heterocyclic ring* or amino*, and n denotes 0, 1 or 2].

The substituent group, which the alkyl group at the afore-mentioned $R^3$, $R^4$, $R^5$, $R^6$, $R^7$ and $R^8$ may have, includes, for example, hydroxy, acyloxy, carbamoyloxy, amino, dialkylamino, acylamino, alkylthio, heterocyclic-thio, carboxy, alkoxycarbonyl, carbamoyl, cyano, azide, aryl and halogen.

The substituent group, which the aryl group at the afore-mentioned $R^3$, $R^4$, $R^5$, $R^6$, $R^7$ and $R^8$ may have, includes, for example, halogen, alkoxy and alkyl.

The substituent group, which the alkenyl group at the afore-mentioned $R^3$, $R^4$, $R^5$, $R^6$, $R^7$ and $R^8$ may have, includes, for example, aryl.

The substituent group, which the heterocyclic ring at the afore-mentioned $R^5$, $R^6$, $R^7$ and $R^8$ may have, includes, for example, alkyl.

The substituent group, which the amino group at the afore-mentioned $R^{12}$ may have, includes, for example, monoalkyl, dialkyl, monoaryl, etc.

The optionally esterified carboxyl group at the afore-mentioned $R^3$, $R^4$, $R^5$, $R^6$, $R^7$ and $R^8$ includes, for example, carboxyl and alkyloxycarbonyl.

The optionally amidated carboxyl group at the afore-mentioned $R^3$, $R^4$, $R^5$, $R^6$, $R^7$ and $R^8$ includes, for example, the group represented by the formula;

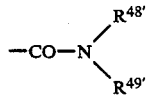

[wherein $R^{48'}$ and $R^{49'}$ independently stand for hydrogen or alkyl, which may form a heterocyclic ring taken together with the adjacent nitrogen atom].

The afore-mentioned alkyl (including alkyl in a group) is preferably those having 1 to 6 carbon atoms.

The afore-mentioned cycloalkyl is preferably those having 3 to 6 carbon atoms.

The afore-mentioned alkenyl is preferably those having 1 to 4 carbon atoms.

The afore-mentioned acyl (including acyl in a group) is preferably those having 1 to 6 carbon atoms, e.g. aryl carbonyl.

The afore-mentioned alkoxy (including alkoxy in a group) is preferably those having 1 to 6 carbon atoms.

Specific examples of the afore-mentioned alkyl having 1 to 6 carbon atoms, cycloalkyl having 3 to 6 carbon atoms, alkenyl having 1 to 4 carbon atoms, acyl having 1 to 6 carbon atoms, alkoxy having 1 to 6 carbon atoms, aryl, heterocyclic ring (excepting the case where the heterocyclic ring is formed together with the adjacent nitrogen atom) and halogen are those set forth as examples for the afore-mentioned $R^1$ etc.

The heterocyclic ring formed together with the adjacent nitrogen is preferably those of five- to six- membered ring, as exemplified by pyrrolyl, pyrrolidinyl, piperidinyl, piperazinyl, etc.

Preferable examples of the afore-mentioned groups represented by $R^3$ and $R^4$ include methyl, ethyl, isopropyl, vinyl, allyl, cyclopropyl, cyclopentyl, cyclohexyl, phenyl, parachlorophenyl, para-methoxyphenyl, acetyl, propionyl, benzoyl, methoxycarbonyl, ethoxycarbonyl, carbamoyl, dimethylaminocarbonyl, cyano, carboxyl, hydroxymethyl, acetoxymethyl, carbamoyloxymethyl, chloromethyl, methylthiomethyl, 1-methyl1H-5-tetrazolylthiomethyl, azidomethyl, acetamidomethyl, cyanomethyl, methoxycarbonylmethyl, hydroxyethyl, acetoxyhydroxyethyl, carbamoyloxyethyl, chloroethyl, methylthioethyl, 1-methyl-5-tetrazolylthioethyl, cyanoethyl, acetamidoethyl, styryl, phenethyl, etc.

Preferable examples of the afore-mentioned groups represented by $R^5$, $R^6$, $R^7$ and $R^8$ include methyl, ethyl, cyclopropyl, cyclopentyl, cyclohexyl, vinyl, allyl, phenyl, benzyl, para-chlorophenyl, para-methoxyphenyl, acetyl, propionyl, benzoyl, cyano, carbamoyl, methoxycarbonyl, ethoxycarbonyl, dimethylaminocarbonyl, acetoxymethyl, methoxymethyl, methylthiomethyl, acetamidomethyl, hydroxy, methoxy, ethoxy, acetoxy, phenyloxy, benzoyloxy, carbamoyloxy, methylamino, dimethylamino, phenylamino, acetylamino, methylthio, ethylthio, 2-acetamidoethylthio, 2-N,N-dimethylaminoethylthio, 2-aminoethylthio, 2-hydroxyethylthio, carboxymethylthio, methoxycarbonylmethoxythio, carbamoylmethylthio, phenylthio, 3-pyridazinylthio, 2-pyrimidinylthio, 4-pyridylthio, 1-methyl-1H-5-tetrazolylthio, benzylthio, 4-pyridylmethylthio, sulfamoyl, phenylaminosulfonyl, chloro, bromo, fluoro, etc.

As the case where $R^5$ or $R^6$ forms a ring with $R^7$ or $R^8$, it may be mentioned the case where the ring is formed with the carbon atoms at the 3- and 4-positions of the 5-oxotetrahydrofuran ring.

Examples of the ring include aryl, heterocyclic ring and cycloalkyl group. The aryl group includes phenyl and so on. The heterocyclic ring includes those analogous to the above-mentioned heterocyclic ring. The cycloalkyl group includes those having 3 to 8 carbon atoms, and examples of the cycloalkyl group include those analogous to the abovementioned cycloalkyl. In the above formulae, the leaving group representable by Y may be any one substitutive with hydrogen at 2-position of the compound (III), which is exemplified by halogen (e.g. bromine, chlorine), sulfonyloxy (e.g. p-toluenesulfonyloxy, p-nitrophenylsulfonyloxy, methanesulfonyloxy) having a substituent (e.g. alkyl, aryl) (the alkyl and the aryl are substituents similar to those mentioned in the foregoing) and di-substituted phosphoryloxy (e.g. diphenylphosphoryloxy, diethylphosphoryloxy).

The compound (III) is allowed to react with the Compound (II) or a reactive derivative thereof to give the compound (I-2) represented by the formula:

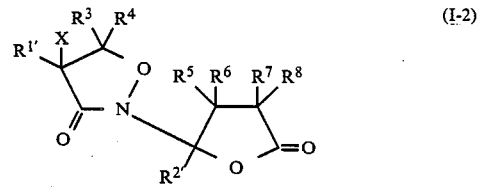

wherein $R^{1'}$, $R^{2'}$, $R^3$, $R^4$, $R^5$, $R^6$, $R^7$, $R^8$ and X are as defined in the foregoing, including the case where all of R³, R⁴, R⁵, R⁶, R⁷, and R⁸ are hydrogen simultaneously, then, when necessary, the compound (I-2) is subjected to modification of R¹' and/or R²' to give the compound (I') represented by the formula:

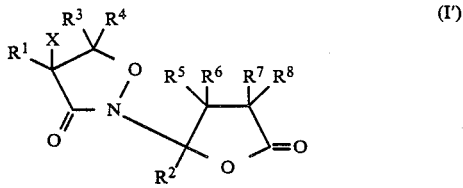

wherein R¹ stands for amino group or an organic residue bonded through nitrogen; R² stands for carboxyl group or a group derivable therefrom; R³, R⁴, R⁵, R⁶, R⁷ and R⁸ independently stand for hydrogen or an organic residue, including the case where R⁵ or R⁶ forms a chemical bond with R⁷ or R⁸, also including the case where all of R³, R⁴, R⁵, R⁶, R⁷ and R⁸ are hydrogen simultaneously; and X stands for hydrogen, methoxy or formylamino.

The reaction of the compound (II) with the compound (III) is conducted in a solvent in the presence of a condensing agent or a Lewis acid. The reaction between a reactive derivative of the compound (II) and the compound (III) is conducted in a solvent.

The condensing agent to be employed is specifically exemplified by N,N'-dicyclohexylcarbodiimide (DCC), a mixture of DCC and N-hydroxysuccinimide or 1-hydroxybenzotriazole; N-ethyl-N'-[3-(dimethylamino)-propyl]carbodiimide; carbonyl diimidazole; N-ethyl-5-isoxazolium3'-sulfonate; 2-ethyl-7-hydroxybenzisoxazolium trifluoroborate; 1-ethoxycarbonyl-2-ethoxy-1,2-dihydroquinoline; combination of 2,2'-dipyridyl disulfide and triphenyl phosphine; combination of carbon tetrachloride and triphenyl phosphine; 2-halogenopyridinium salt e.g. 2-chloro-1-methyl-pyridinium iodide or 2-fluoro-1-methyl-pyridinium tosylate; pyrimidinium salts e.g. 2-chloro-1-methyl pyrimidinium fluorosulfate; and onium salts of azalene e.g. 2-chloro-3-ethyl-benzoxazolium tetrafluoroborate and 2-fluoro-3-methylbenzothiazolium fluorosulfate [cf: Angewandte Chemie, International Edition), 18, 707 (1979)].

The Lewis acid to be employed is exemplified by boron trifluoride etherate, zinc chloride, tin tetrachloride, aluminium chloride, titanium tetrachloride, boron trichloride, etc.

As the reactive derivatives of the compound (II) are usable those employed c-terminal activation process in the synthesis of peptide. These reactive derivatives prepared in a solvent can be used for the condensation reaction as they are, without subjecting to isolation process. Specific examples of the reactive derivatives of carboxylic acid used herein are acid halides e.g. acid chloride and acid bromide; acid azide; mixed acid anhydrides with carbonic acid monoalkyl ester e.g. a mixed acid anhydride with aliphatic carboxylic acid e.g. acetic acid, pivalic acid, valeric acid, isovaleric acid, trichloroacetic acid, etc., a mixed acid anhydride with an acid e.g. phosphoric acid such as diphenyl phosphoric acid, diethyl phosphoric acid, etc. and sulfuric acid, etc., a mixed acid anhydride with e.g. benzoic acid, symmetric type acid anhydrides; amido compounds in which acyl group is bonded to the nitrogen in the ring of e.g. pyrazole, imidazole, 4-substituted imidazole, dimethyl pyrazole, benzotriazole, triazolidine-2-thione, etc.; active esters with e.g. 4-nitrophenyl, 2,4-dinitrophenyl, trichlorophenyl, pentachloropheyl, pentafluorophenyl, cyanomethyl, N-hydroxysuccinimide, N-hydroxyphthalimide, etc.; and active thioester with, among others, heterocyclic thiol e.g. 2-pyridylthio, 2-benzthiazolyl thiol, etc.

The reaction is conducted by, in a solvent, allowing the compound (III) to react with equimolar or a little excess amount of the compound (II) and equimolar or a little excess amount of a condensing agent or a catalytic amount of a Lewis acid, or with equimolar or a little excess amount of a reactive derivative of the compound (II). As the solvent, any one can be employed so long as it is inert to the reaction, which is exemplified by conventional ones such as dichloromethane, chloroform, tetrahydrofuran, dioxane, diethylester, ethyl acetate, benzene, toluene, n-hexane, acetonitrile and N,N-dimethylformamide.

Depending on cases, this reaction may be conducted in the presence of a base (for example, in case where 2-chloro-1-methylpyridinium iodide, 2,2'-dipyridyl disulfide-triphenylphosphine, carbon tetrachloridetriphenylphosphine or the like is employed). Preferable examples of the base include triethylamine, isopropylethylamine, N-methylmorpholine and 3,4-dihydro-2H-pyrido[1,2-a]pyrimidin-2-one, and, among them, 3,4-dihydro-2H-pyrido[1,2-a]pyrimidin-2-one is preferable.

Further, there is such a case where the reaction may be conducted in the presence of e.g. silver chloride, silver tetrafluoroborate or silver perchlorate (for example, 2,2'-dipyridyldisulfide-triphenylphosphine is employed as the condensing agent).

The reaction temperature is not specifically limited, as far as the reaction proceeds, but the reaction is conducted normally at about −50° C. to 150° C., preferably about −10° C. to 100° C. The reaction time varies with the types of starting compounds, reagents and solvents employed, but it is usually about five minutes to about 30 hours. When the condensation is conducted in the presence of a Lewis acid as the catalyst, a dehydrating agent such as Molecular Sieves is in some instances allowed to co-exist in the reaction system.

Alternatively, the compound (III) is allowed to react with the compound (IV) to give the compound (I-2), then, when necessary, the compound (I-2) is subjected to modification of R¹' and/or R²' to give the compound (I').

The reaction between the compound (III) and the compound (IV) is conducted in a solvent in the presence of a base. The base is exemplified by organic amines such as triethylamine, tripropylamine, tri-n-butylamine, diisopropylethylamine, triethylene diamine (DABCO), 1,8-diazabicyclo[5.4.0]-7-undecene(DBU), N-methylmorpholine, N-methylpiperidine, N-methyl-pyrrolidine, 3,4-dihydro-2H-pyrido[1,2-a]pyrimidin-2-one, 4-dimethyl aminopyridine, pyridine, lutidine, γ-colidine, etc.; alkali metals such as lithium, sodium, potassium, cesium, etc.; alkaline earth metals such as magnesium, calcium, etc.; or hydrides, hydroxides, carbonates or alcoholates of them. The solvent is exemplified by conventional ones such as dichloromethane, chloroform, tetrahydrofuran, dioxane, benzene, toluene, acetonitrile, dimethylacetamide, dimethylformamide, etc. Among the above-mentioned bases, liquid ones can be used to allow them to serve dual purposes of the base and solvent. In this reaction, the compound (IV) and the base are normally used about 1 mole per mole of the compound (III), but can also be employed in excess, unless it affects adversely the reaction. The reaction temperature is in the range of about $-20°$ C. to $100°$ C., and the reaction time ranges normally about 5 minutes to 30 hours.

When necessary, the compound (I-2) thus obtained above are subjected to modification of $R^{1'}$ and $R^{2'}$ to give the compound (I'). The reaction for performing this modification is exemplified by deprotecting reaction, acylation, ureido formation (thioureido formation), alkylation, alkenylation, thionation, silylation, phosphorylation, esterification, amidation, etc.

The above-mentioned deprotecting reaction can be conducted, depending on the kinds of the protecting groups, by suitably selecting from conventional ones including methods using an acid, a base or hydrazine, and reduction. When the method using an acid is employed, the acid is exemplified by inorganic acids such as hydrochloric acid, sulfuric acid, phosphoric acid, etc.; organic acids such as formic acid, acetic acid, trifluoroacetic acid, propionic acid, etc.; as well as acid ion-exchange resins, though varying with the kinds of protecting groups or other conditions. When the method using a base is employed, the base is exemplified by inorganic bases including e.g. hydroxides or carbonates of alkali metals such as sodium and potassium, alkaline earth metals such as calcium and magnesium; organic bases including e.g. metal alkoxides, organic amines or quaternary ammonium salts; as well as basic ion-exchange resins, though varying with the kinds of protecting groups or other conditions. In the above cases where acids or bases are used, when the use of a solvent is required, a hydrophilic organic solvent, water or a mixture solvent is often counted.

In the case of resorting to reduction, are employed among others, the method where a metal e.g. tin, zinc, etc. or a metal compound e.g. chromium dichloride, chromium acetate, etc. and an organic or inorganic acid e.g. acetic acid, propionic acid, hydrochloric acid, etc. are used and the method where the reduction is conducted in the presence of a metal catalyst for catalytic reduction. Examples of the catalyst for catalytic reduction include platinum catalysts e.g. platinum wire, spongy platinum, platinum black, platinum oxide and colloidal platinum, palladium catalysts e.g. spongy palladium, palladium black, palladium oxide, palladium barium sulfate, palladium barium carbonate, palladium carbon, palladium silica-gel and colloidal palladium, reducing nickel, nickel oxide, Raney nickel and Urushibara nickel. In the case of resorting to reduction using a metal and an acid, are employed a metal such as iron or chromium and an inorganic acid such as hydrochloric acid or an organic acid such as formic acid, acetic acid or propionic acid. The method resorting to reduction is usually conducted in a solvent. In the catalytic reduction, for example, alcohols e.g. methanol, ethanol, propyl alcohol or isopropyl alcohol or ethyl acetate are often used. In the method of using a metal and an acid, are often employed water, acetone, etc., but, when the acid is liquid, it is allowed to serve as a solvent as well.

The reaction temperature in the methods using an acid or a base or resorting to reduction usually ranges from that under cooling to that under warming.

For removing the protecting groups in the respective groups in the compounds obtained, procedures similar to that mentioned above can be applied.

By subjecting the compound (I-2) to deprotection reaction, the compound (I-3), which corresponds to the compound (I') wherein $R^1$ is amino group and $R^2$ is a group derived from carboxyl group, or the compound (I-4), which corresponds to the compound (I') wherein $R^2$ is carboxyl group and $R^1$ is an acid residue bonded through nitrogen, can be prepared.

By further subjecting these compounds to deprotection reaction, the compound (I-5), which corresponds to the compound (I') wherein $R^1$ is amino group and $R^2$ is carboxyl group, can be prepared.

Alternatively, by subjecting the compound (I-2) to deprotecting reaction, the compound (I-5) can be prepared at one stroke.

When a compound (I') wherein $R^5$ or $R^6$ forms a chemical bonds with $R^7$ or $R^8$ is obtained, the compound (5-oxo-2,5-dihydro-2-furancarboxylic acid derivative) may be subjected, when necessary, to hydrogenation at the double bond. The hydrogenation is conducted by a reducing procedure similar to that used for elimination of the protecting group as mentioned above. By conducting the reduction reaction, hydrogenation at the double bond and elimination of the protecting group can be conducted simultaneously.

Also, the compound (I-3) can be led to the compound (I-2) by subjecting to, for example, acylation, ureido formation (thioureido formation), alkylation, alkenylation, thionation, silylation and phosphorylation. These reactions are described in detail as follows:

Acylation

Acylation of the amino group can be carried out by reacting a starting compound with an acylating agent containing the acyl group in the group $R^1$, such as a reactive derivative of carboxylic acid, in a solvent. As the reactive derivative of carboxylic acid, there are used, for example, acid halides, acid anhydrides, amide compounds, active esters or active thioesters, and specific examples of such a reactive derivative are to be mentioned in the following.

(1) Acid halides:

As the acid halide as employed herein, there are used, for example, acid chlorides, or acid bromides.

(2) Acid anhydrides:

As the acid anhydride as employed herein, there are used, for example, monoalkyl carbonic acid mixed acid anhydrides, mixed acid anhydrides comprising aliphatic carboxylic acid, (e.g. acetic acid, pivalic acid, valeric acid, isovaleric acid, trichloroacetic acid, etc.), mixed acid anhydrides comprising aromatic carboxylic acids (e.g., benzoic acid, etc.) or symmetric type acid anhydrides.

(3) Amide compounds:

As the amide compound as employed herein, there are used, for example, compounds having an acyl group attached to the nitrogen in the ring, such as pyrazole, imidazole, 4-substituted imidazoles, dimethylapyrazole and benzotriazole.

(4) Active esters:

As the active ester, there are used, for example, esters such as methyl esters, ethyl esters, methoxymethyl esters, propargyl esters, 4-nitrophenyl esters, 2,4-dinitrophenyl esters, trichlorophenyl esters, pentachlorophenyl esters and mesylphenyl esters as well as esters formed with 1-hydroxy-1H-2-pyrrolidone, N-hydroxysuccinimide or N-hydroxyphthalimide, etc.

(5) Active thioesters:

As the active thioester, there are used, for example, thioesters formed with heterocyclic thiols, such as 2-pyridylthiol or 2-benzothiazolylthiol.

Various kinds of reactive derivatives as above are selected depending upon the type of carboxylic acids.

This reaction is in some instances carried out in the presence of a base. Examples of the suitable base include aliphatic tertiary amines (e.g., trimethylamine, triethylamine, tripropylamine, tri-n-butylamine, etc.), tetriary amines such as N-methylpiperidine, N-methylpyrrolidine, cyclohexyldimethylamine and N-methylmorpholine, dialkylamines such as di-n-butylamine, diisobutylamine and dicyclohexylamine, aromatic amines such as pyridine, lutidine and γ-collidine, hydroxides or carbonates of alkali metals such as lithium, sodium and potassium, or hydroxides or carbonates of alkaline earth metals such as calcium and magnesium, etc.

In this procedure, the reactive derivative of carboxylic acid is normally used at a ratio of about 1 mole per mole of the compound (I-3), but can also be employed in excess, unless it affects adversely the reaction. In the case of a base being used, the amount of such base to be used is normally about 1 to 30 moles per mole of the compound (I-3), preferably about 1 to 10 moles, varying with the types of the starting compound (I-3) used and reactive derivative of carboxylic acid employed and other reaction conditions. This reaction is carried out normally in a solvent. As the said solvent, there are used conventional solvents, either alone or as a mixture, for example, ethers such as dioxane, tetrahydrofuran, diethyl ether, diisopropyl ether, propylene oxide and butylene oxide, esters such as ethyl acetate and ethyl formate, halogenated hydrocarbons such as chloroform, dichloromethane, 1,2-dichloroethane and 1,1,1-trichloroethane, hydrocarbons such as benzene, toluene and n-hexane, amides such as N,N-dimethylformamide and N,N-dimethylacetamide, or nitriles such as acetonitrile. In the above mentioned bases, the liquid ones can also be used to allow them to serve dual purposes of the base and solvent. The reaction temperature is not specifically limited, as far as the reaction proceeds, but the reaction is conducted normally at about −50° C. to 150° C., preferably about −30° C. to 80° C. The reaction goes to termination normally within several ten minutes to several ten hours, e.g. about 10 nimutes to 10 hours, varying with the types of starting compound and base employed, the reaction temperature and the kind of solvent, but it in some instances requires several ten days.

Ureido formation (thioureido formation)

The reaction of converting the amino group into the ureido or thioureido group is carried out by reacting the starting compound with a substituted isocyanate or isothiocyanate containing a group represented by the abovedescribed formula:

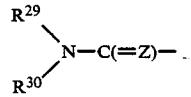

(wherein $R^{29}$, $R^{30}$ and Z are as defined hereinbefore) in the presence of a solvent. As the said substituted isocyanate, there are used, for example, methyl isocyanate, ethyl isocyanate, phenyl isocyanate or p-bromophenyl isocyanate, while as the substituted isothiocyanate, there are employed, for example, methyl isothiocyanate or phenyl isothiocyanate. In this reaction, the substituted isocyanate or substituted isothiocyanate is normally used to a ratio of about 1 mole per mole of the compound (I-3), but can also be employed in excess, unless it affects adversely the reaction. As the suitable solvent, there are used, for example, tetrahydrofuran, diethyl ether, ethyl acetate, chloroform, dichloromethane or toluene. The reaction temperature is in the range of about −20° C. to 50° C., and the reaction time ranges normally from about 10 minutes to 5 hours.

Alkylation

The reaction of combining the amino group of the compound (I-3) with a group bonded through carbon is to be described below as alkylation.

The alkylated derivative of the compound (I-3) can be prepared by reacting the compound (I-3) with an alkylating agent containing a group bonded to the relevant nitrogen of the group $R^1$ through carbon. As the alkylating agent, there are used, for example, halogenated alkyl compounds such as propyl chloride, butyl chloride, benzyl chloride, butyl bromide, benzyl bromide, allyl bromide, methyl iodide, ethyl iodide and propyl iodide, dialkyl sulfate compounds such as dimethyl sulfate and diethyl sulfate, substituted sulfonate compounds such as methyl mesylate, ethyl mesylate, methyl tosylate and ethyl tosylate, or dihalogenated alkyl compounds (e.g., 1,5-dichloropentane, 1,4-dichlorobutane, etc.). This reaction is normally carried out in a solvent, and examples of the solvent usable include water, methanol, ethanol, benzyl alcohol, benzene, N,N-dimethylformamide, tetrahydrofuran or acetonitrile. The temperature of this reaction is about 20° C. to 200° C., while the reaction time ranges from about 30 minutes to 50 hours. This reaction, by changing the reaction conditions, such as a molar ratio of the compound (I-3) to the alkylating agent, permits selective production of a secondary amine, tertiary amine or quaternary amine compound. It is also possible to introduce different substituent groups into the nitrogen, by conducting the reaction in stepwise. The reaction of introducing a group bonded through carbon other than alkyl groups can be carried out by procedures comparable to the above one.

Alternatively, the said alkylation can also be conducted by combining the compound (I-3) with a carbonyl compound in the presence of a reducing agent. Examples of the reducing agent which is useful in this reaction include lithium aluminum hydride, sodium cyanoborohydride, sodium borohydride, sodium, sodium amalgam and combinations of zinc with acids. Also, the reaction can be carried out through catalytic reduction using for example palladium, platinum and rhodium as a catalyst. The reaction of converting the amino group into a group represented by $R^{31}$-NH- (imino-substituted alkylamino, alkylimino-substituted alkylamino or substituted guanidino group):

The reaction of converting the amino group into an imino-substituted alkylamino or alkylimino-substituted alkylamino group is carried out by reacting the starting compound with for example imidoesters in a solvent such as dioxane, tetrahydrofuran, N,N-dimethylformamide, chloroform, acetone, acetonitrile and water. As the suitable imidoesters, there are used, for example, methyl formimidate, ethyl formimidate, benzyl formimidate, methyl acetoimidate, ethyl acetoimidate, methylphenyl acetoimidate, ethyl N-methylformimidate, methyl N-ethylformimidate or methyl N-isopropylformimidate. The reaction temperature is in the neighborhood of 0° C. to 25° C., while the reaction time ranges normally from 1 to 6 hours. The reaction of converting the amino group into guanidino group is conducted by reacting the starting compound with, for example, O-alkyl- or O-aryl pseudourea or S-alkyl- or S-aryl pseudothioureas in a solvent, such as water, N,N-dimethylformamide and hexamethylphosphoramide. As the above pseudoureas, there are used, for example, O-methyl pseudourea, S-methyl pseudourea, O-2,4-dichlorophenyl pseudourea or O-N, N-trimethyl pseudourea, while as the above pseudothioureas, there are employed, for example, S-p-nitrophenyl pseudothiourea. The reaction temperature is in the neighborhood of 0° to 40° C., while the reaction time is normally in the range of 1 to 24 hours.

Alkenylation (imination)

Alkenylation (imination) of the conpond (I-3) can be carried out by dehydration condensation of the compound (I-3) with a carbonyl compound. This reaction proceeds in the absence of solvent, but can also be carried out in a solvent. Acid or base is in some instances used as a catalyst. The objective compound can also be prepared by heating under reflux the compound (I-3) and a carbonyl compound in the presence of a dehydrating agent or with use of a dehydration apparatus such as Dean-Stark. The solvent, which is usable in this reaction, includes, for example, benzene, toluene, dichloromethane or ethanol. The reaction temperature ranges from about 0° C. to 200° C., while the reaction time ranges from about 1 hour to 20 hours. The acid, which is used as a catalyst, includes, for example, benzenesulfonic acid, methanesulfonic acid, sulfuric acid, boron trifluoride and zinc chloride, while the base includes, for example, potassium hydroxide, and sodium carbonate. The dehydrating agent, which is useful in this reaction, includes, for example, Molecular Sieves, silica gel, anhydrous magnesium sulfate and anhydrous sodium sulfate.

Thionation

The thionation reaction for the compound (I-3) is normally carried out by reacting the compound (I-3) with a halogenated thio compound (e.g., halogenated sulfonyl, halogenated sulfinyl, halogenated sulfenyl, etc.) containing a group represented by the formula $R^{39}$-$SO_n$- (wherein $R^{39}$ and n are as defined hereinbefore) in a solvent in the presence of a base. The solvent, which is used in this reaction, includes, for example, water, acetone, dioxane, N, N-dimethylformamide, benzene, tetrahydrofuran, dichloromethane, or solvent mixtures thereof. As the base, there are used, for example, organic bases, such as pyridine, picoline, triethylamine, isopropylamine and N-methylmorpholine, and inorganic bases, such as sodium hydroxide, potassium hydroxide, sodium carbonate, sodium hydrogencarbonate, and potassium carbonate. This reaction normally requires about 1 equivalent of the halogenated thio compound and about 1 to 10 equivalents of the base to be used against the compound (I-3). The reaction temperature is about −20° C. to 80° C. and the reaction time ranges from 15 minutes to 10 hours.

This reaction is also conducted using a thioacid anhydride (e.g., toluenesulfonic anhydride, trifluoromethanesulfonic anhydride, etc.) in place of the halogenated thio compound. Also, this reaction can be carried out by reacting the starting compound with a thionating reagent such as N-sulfonyl-N-methylpyrrolidinium, N-sulfonylimidazolide or N-sulfonyl-1H-1,2,4-triazolide.

Silylation

The silylation reaction for the compound (I-3) can be carried out normally by reacting the compound (I-3) with a halogenated silyl compound (e.g., silyl chloride compounds, silyl bromide compounds, etc.) containing a group represented by the formula

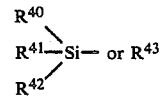

(wherein $R^{40-43}$ are as defined hereinbefore) in the presence of a base. The said base includes for example, organic bases such as pyridine, picoline, triethylamine, diisopropylamine and N-methylmorpholine. The reaction is preferably carried out in a solvent, and the said solvent includes, for example, acetone, dioxane, N,N-dimethylformamide, benzene, tetrahydrofuran and dichloromethane. The reaction temperature is about −20° C. to the boiling point of the solvent used, or about −20° C. to 80° C., while the reaction time ranges from about 15 minutes to 20 hours.

Phosphorylation

The phosphorylation reaction for the compound (I-3) is normally carried out by reacting the compound (I-3) with an approximately equimolar amount of a phosphoryl chloride (e.g., dimethylphosphoryl chloride, diethylphosphoryl chloride, diphenylphosphoryl chloride, dibenzylphosphoryl chloride, etc.) containing a group represented by the formula

(wherein $R^{44}$ and $R^{45}$ are as defined hereinbefore) in a solvent in the presence of an approximately equimolar or excessive amount of a base. As the base, there are used, for example, organic bases such as pyridine, picoline, triethylamine and N-methylmorpholine, and inorganic bases, such as sodium hydroxide, potassium hydroxide, sodium hydrogencarbonate and sodium carbonate. As the solvent, there are employed, for example, either alone or as a solvent mixture, water, acetone, acetonitrile, dioxane, N,N-dimethylformamide, tetrahydrofuran and dichloromethane. The reaction temperature is about −20° C. to 80° C., while the reaction time ranges from 15 minutes to 15 hours.

The compound (I-5) can be converted to the compound (I-4) by subjecting to, for example, acylation, ureido formation (thioureido formation), alkylation, alkenylation, thionation, silylation or phosphorylation. These reactions can be conducted in a manner similar to the above-mentioned conversion reaction from the compound (I-3) to the compound (I-2).

Alternatively, the compound (I-4) can be converted to the compound (I-2) by subjecting to, for example, esterification of the carboxylic acid or amidation of the carboxylic acid. These reactions are described as follows:

Esterification of carboxylic acid

The esterification is carried out, for example, by the following procedures:

(1) The starting compound is reacted with a diazoalkane, such as diazomethane, phenyldiazomethane and diphenyldiazomethane, in a solvent, such as tetrahydrofuran, dioxane, ethyl acetate and acetonitrile, at about 0° C. to its refluxing temperature for about 2 minutes to 2 hours.

(2) An alkali metal salt of the starting compound is reacted with an activated alkyl halide such as methyl iodide, benzyl bromide, p-nitro-benzyl bromide, m-phenoxybenzyl bromide, p-t-butylbenzyl bromide and pivaloyloxymethyl chloride. With reference to the suitable reaction conditions, the reaction is allowed to proceed in a solvent, such as N,N-dimethylformamide, dimethylsulfoxide or hexamethylphosphoramide, at about 0° C. to 60° C. for about 2 minutes to 4 hours. Coexistence of triethylamine, etc. in this reaction solution does not affect adversely the reaction.

(3) The starting compound is reacted with an alcohol such as methanol, ethanol and benzyl alcohol. This reaction is carried out in the presence of a carbodiimide condensing agent such as DCC, at about 0° C. to the refluxing temperature of the used solvent for about 15 minutes to 18 hours. As the solvent, there are used, for example, chloroform, dichloromethane and dichloroethane.

(4) An acid anhydride of the starting compound formed by reacting the starting compound with an acid chloride, such as ethyl chlorocarbonate and benzyl chlorocarbonate is reacted with an alcohol, such as those as mentioned in the above item (3) under the reaction conditions as described in the above item (3). The acid anhydride is obtainable by reacting the starting compound with the acid chloride in a solvent, such as tetrahydrofuran and dichloromethane, at 25° C. to the refluxing temperature for about 15 minutes to 10 hours.

(5) The starting compound is reacted with a silylating agent, such as trimethylsilyl chloride and t-butyl-dimethylsilyl chloride, in the co-presence of, for example, triethylamine in a solvent such as dichloromethane, chloroform and tetrahydrofuran, at about 0° C. to the refluxing temperature for about 15 minutes to 16 hours.

Amidation of carboxylic acid

The amidation of carboxylic acid is carried out by synthesizing an acid anhydride of the starting compound from the starting compound and an acid chloride, such as ethyl chlorocarbonate, benzyl chlorocarbonate and pivaloyl chloride, or an acid anhydride, such as acetic anhydride and trifluoroacetic anhydride, followed by reaction with ammonia or a selected amine, for example, the above-mentioned alkyl-, dialkyl-, aralkyl- or heterocyclic-ring amine reagent. Alternatively, the reaction of carboxylic acid with the above-mentioned amine may be conducted in the presence of a condensing agent such as DCC or N-3-dimethylaminopropyl-N-ethylcarbodiimide.

The above reaction is carried out in a solvent, such as dichloromethane, tetrahydrofuran and N,N-dimethylformamide, at about 0° C. to the refluxing temperature (e.g. up to about 160° C.) for 15 minutes to 16 hours.

The compound (I') wherein X is methoxy can be prepared also by subjecting the compound (I') wherein X is hydrogen to methoxylation.

Methoxylation

With reference to the above-mentioned methoxylation there can be applied the methoxylation methods for the 6-position or 7-position conventionally adapted in the fields of penicillin or cephalosporin. The methoxylation of penicillin or cephalosporin is described in detail, for example, by E. M. Gordon, R. B. Sykes, et. al. in "Chemistry and Biology of $\beta$-Lactam Antibiotics", vol. 1, p. 199 (1982), published by Academic Press, where the description is given on the methods of methoxylation through (1) a diazo intermediate, (2) acylimine intermediate, (3) keteneimine or related imine intermediate, (4) quinoidoimine intermediate, (5) sulfeneimine intermediate, (6) eneimine intermediate, etc. Any of these methods can permit the production of the objective compound, and as their representative example, the detailed description is to be given to the method of methoxylation through an acylimine intermediate.

The methoxylation reaction is carried out by acting an alkali metal salt of methanol and a halogenating agent on the starting compound in the presence of methanol. As the alkali metal salt of methanol, there are used, for example, lithium methoxide, sodium methoxide and potassium methoxide, while as the halogenating agent, there are employed, for example, t-butyl hypochloride, N-chlorosuccinimide, N-bromosuccinimide, N-chloroacetamide, N-bromoacetamide, N-chlorobenzenesulfonamide, chlorine and bromine. This reaction is carried out in a solvent, and as the solvent, there are used, for example, tetrahydrofuran, dioxane, dichloromethane, chloroform, acetonitrile, methanol and N,N-dimethylformamide. This reaction is desirably carried out by dissolving or suspending the starting compound in the above-mentioned solvent and adding an alkali metal salt of methanol, methanol and an halogenating agent to the solution or suspension to allow the reaction to proceed. In this case, it is preferable to add not less than 1 equivalent of methanol, about 1 to 3.5 equivalents of an alkali metal salt of methanol and about 1 to 2 equivalents of a halogenating agent relative to the starting compound to allow the reaction to proceed. The reaction proceeds at about $-80°$ C. to 30° C. for about one to 30 minutes and is suspended by making the reaction system acidic. As the acid to be used for the suspension of the reaction, there are used, for example, formic acid, acetic acid or trichloroacetic acid. After the termination of the reaction, the excess of halogenating agent is removed for example by treatment with a reducing agent, such as sodium thiosulfate and trialkyl esters of phosphorous acid. The compound (I') wherein X is formylamino can be prepared also by subjecting the compound (I') wherein X is hydrogen to formylamination.

Formylamination

The formylamination is carried out by converting the compound (I') wherein X is hydrogen into an imine derivative of the formula:

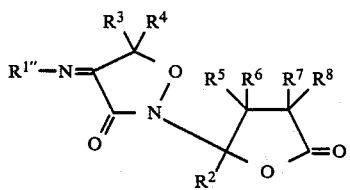

wherein R[1"] is the moiety other than nitrogen in the organic residue bonded through nitrogen; R[2], R[3], R[4], R[5], R[6], R[7] and R[8] are as defined hereinbefore, including the case where all of R[3], R[4], R[5], R[6], R[7] and R[8] are simultaneously hydrogen, and acting a nucleophilic derivative of formamide on it. The nucleophilic derivative of formamide includes, for example, N-silyl, N-stannyl and N-phosphorylformamide derivatives, and among them, the suitable one is N,N-bis(trimethylsilyl) formamide. The said formylamination reaction is normally carried out in a solvent under an inert atmosphere of nitrogen, argon, etc., whereby the reaction temperature is about $-100°$ C. to $-20°$ C., preferably about $-80°$ C. to $-50°$ C., and the reaction time is about 10 minutes to 8 hours, preferably about 15 minutes to 2 hours. The solvent to be used may suitably be any aprotic solvent, and includes, for example, tetrahydrofuran, N,N-dimethylformamide, hexamethylphosphoramide or dioxane. Subsequent to the reaction, hydrolysis, with acid or base or treatment with metal ions such as ions of mercury, silver, thallium or copper, can be carried out to produce the formylamino group. It is added that the imine derivative can be produced by a procedure similar to the procedure for the methoxylation described in the literature by E. M. Gordon, et. al. mentioned above.

The objective compound (I') thus obtained can be isolated and purified by the per se known means, such as concentration, pH adjustment, solvent extraction, lyophilization, crystallization, recrystallization, fractional distillation and chromatography.

The presence of two asymmetric carbons in the basic skeleton allows theoretically the objective compound (I') to exist in four kinds of stereoisomers, and their individual stereoisomers and mixtures thereof fall into the scope of this invention. Similarly, the occurrence of any asymmetric carbon in the groups represented by R[1] to R[8], and at 5-position of the 3-oxoisoxazolidine ring and/or 3- or 4- position of the 5-oxotetrahydrofuran ring results in existence of stereoisomers, and their individual stereoisomers and mixtures thereof are also included in the scope of this invention. In cases in which the above-described reaction produces these stereoisomers as a mixture, their individual stereoisomers can be isolated by the conventional methods, such as various chromatographic procedures and recrystallization, if necessary.

The conpound (I') of this invention can in some instances act on bases to form salts. The said base includes, for example, inorganic bases, such as sodium, potassium, lithium, calcium, magnesium and ammonia, and organic bases, such as pyridine, collidine, triethylamine and triethanolamine.

The compound (I'), when produced in the free form, may be allowed to form salts by use of the conventional means, and the compound (I') obtained in the form of salt may be converted into the free form by use of the conventional means.

Also, the compound (I') in some instances forms the intramolecular salt, and such salt falls within the scope of this invention, as well.

The stereoisomers of the compound (I'), either alone or as a mixture, can be used as a drug.

The compound (IV) employable as a starting material for the method of this invention can be prepared by, for example, the following processes. In the formula, R[2'], R[5], R[6], R[7] and R[8] and Y are as defined above.

Compound (II) →Compound (IV)

This process is to convert the compound (II) to the compound (IV). This reaction is usually conducted by allowing the compound (II) to react with an activating agent. Examples of the activating agent include halogenating agents such as thionyl chloride, thionyl bromide, sulfuryl chloride, phosphorus oxychloride, oxalyl chloride, chlorine, bromine or carbon tetrachloride and triphenyl phosphine; sulfonylating agents such as p-toluene sulfonic anhydride, p-nitrobenzene sulfonic anhydride, 2,4,6-triisopropylphenyl sulfonic anhydride, methanesulfonic anhydride, p-toluene sulfonyl chloride and p-chlorobenzene sulfonyl chloride; and phosphorylating agents such as diphenyl phosphoryl chloride, dimethyl phosphoryl chloride and diethyl phosphoryl chloride. This reaction is conducted by allowing the compound (II) to react with about equimolar to excess amount of the above-mentioned activating agent in a solvent or in the absence of solvent. This reaction can also be conducted by using a base such as triethylamine, diisopropylamine, pyridine, 4-dimethylamino pyridine, etc., so long as it does not affect the reaction adversely. The solvent to be employed is exemplified by dichloromethane, chloroform, carbon tetrachloride, 1,2-dichloroethane, N,N-dimethylformamide, N,N-dimethyl acetamide, acetonitrile, tetrahydrofuran, benzene, toluene, etc. The reaction temperature is usually about $-20°$ C. to about $100°$ C., and the reaction time is about 30 minutes to about 50 hours.

Compound (IV) →Compound (IV)

This process is to prepare the compound (IV) (The following explanation is directed to preparing the compound (IV) wherein R[6] and R[8] form a chemical bond, and Y stands for halogen) by allowing a compound representable by the formula;

to react with a halogenating agent. While the starting compound (VI), wherein R[2']=methyl, R[5]=R[6]=H, is known (cf. official gazette of Japanese Patent Publication No. Sho35 (1960)-9031), and other species of the compound (VI) can be prepared by a method analogous to that described in this literature reference. This reaction is conducted by allowing equivalent or a little excess amount of a halogenating agent to react with the compound (VI) in a solvent. Preferable halogenating agent are chlorine, bromine, etc. The solvent to be employed includes chloroform, carbon tetrachloride, dichloromethane, 1,2-dichloroethane, benzene, acetonitrile, etc. The reaction temperature is about 0° C. to 80° C., and the reaction time is about 10 minutes to 10 hours.

The compound (IV) can also be prepared by subjecting a starting compound corresponding to the compound (IV) wherein R²' is carboxyl group to, for example, a reaction similar to the afore-mentioned esterification or amidation of the carboxylic acid to convert the compound (I-4) to the compound (I-2).

The compound (II) employable as the starting compound for the method of this invention can be prepared by, for example, the following process. In the formula, R²', R⁵, R⁶, R⁷ and R⁸ are as defined in the foregoing.

Compound (V)→Compound (II)

This process is to prepare a half-ester derivative of the compound (II) by selective esterification of the carboxyl group at 1-position of a compound representable by the formula;

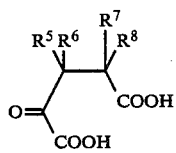

This reaction is conducted by allowing the compound (V) to react with about equivalent or a little excess amount of an esterifying agent in a solvent in the presence of an equivalent base. The esterifying agent is exemplified by halides such as methyl iodide, benzyl bromide, p-nitrobenzyl bromide, m-phenoxybenzyl bromide, p-t-butylbenzyl bromide, diphenylmethyl bromide, pivaloyoxymethyl chloride, etc., and dialkyl sulfates such as dimethyl sulfate, diethyl sulfate, etc. The base is exemplified by organic amines such as diisopropylamine, dicyclohexylamine, cyclohexylisopropylamine, triethylamine, tripropylamine, tri-n-butylamine, diisopropyl ethylamine, DABCO, DBU, N-methyl morpholine, N-methyl piperidine, N-methyl pyrrolidine, 3,4-dihydro-2H-pyride [1,2-a]pyrimidin-2-one, 4-dimethylamino pyridine, pyridine, lutidine, γ-colidine, etc., hydrides, hydroxides and carbonates of an alkali metal such as lithium, sodium, potassium, cesium, etc.

The solvents to be employed are, among others, N,N-dimethylformamide, N,N-dimethylacetamide, hexamethyl phosphoramide, dimethyl sulfoxide, dichloromethane, acetonitrile and tetrahydrofuran. The reaction temperature usually ranges from about −20° C. to about 100° C., and the reaction time is about 5 minutes to about 30 hours.

Compound (V)→Compound (VII)→Compound (VII')→Compound (II)

This process is to prepare the compound (II), which comprises allowing benzylcarbamate to react with the compound (V) to give the compound (VII) represented by the formula;

subjecting the compound (VII) to esterification to give the compound (VII') represented by the formula;

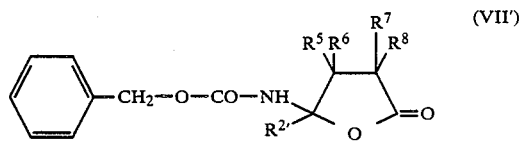

then by subjecting the compound (VII') to the treatment with an acid.

This reaction is conducted by subjecting the compound (V) and about equivatent or a little excess amount of benzylcarbamate to heating under reduced pressure of about 0.1 mmHg to about 50 mmHg usually in the absence of solvent to cause dehydrative condensation. The reaction temperature usually ranges from about 50° C. to about 120° C., and the reaction time is about 30 minutes to 20 hours. The compound (VII) is then subjected to esterification to convert into the compound (VII'). The esterification was conducted by applying conditions similar to the above-mentioned esterification of the compound (V) to the compound (II). Alternatively, the esterification is conducted between diazo-alkanes e.g. diazo-methane and e.g. methanol, ethanol or benzyl alcohol in the presence of a carbodiimide condensing agent e.g. DCC. While the method for the esterification is suitably selected depending on the ester then desired, the ester is preferably a one relatively stable against acid, because the ester is then subjected to the acid treatment. The compound (VII') is converted to the compound (II) by the acid treatment. Examples of the acid include hydrochloric acid, sulfuic acid, hydrobromic acid, perchloric acid, periodic acid, formic acid, acetic acid, trifluoracetic acid and p-toluenesulfonic acid, and they can be used singly or in combination. Among them, use of the combination of hydrobromic acid and acetic acid is preferable. The reaction temperature ranges from about 0° C. to 50° C. and the reaction time is about 15 minutes to 5 hours.

Compound (V)→Compound (VIII)→Compound (II)

This process comprises allowing halogeno-carbonic acid ester to react with the compound (V) to give the compound (VIII) represented by the formula;

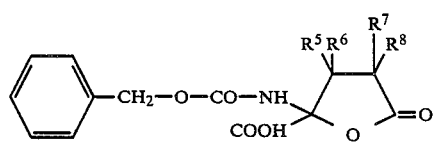

then subjecting the compound (VIII) to decarboxylation to produce the compound (II). It has been known by a literature reference [J. M. Domagala, Tetrahedron Letters, 21, p.4997, 1980] that 1-ethyl ester of 2-oxoglutaric acid was synthesized by allowing 2-oxoglutaric acid [the compound (V) wherein R⁵=R⁶=R⁷=R⁸=H] to react with ethyl chlorocarbonate, then subjecting the resultant to decarboxylation. The reaction of the present invention comprises allowing the compound (V) to react with halogeno-carbonic acid ester in a solvent in the presence of a base then subjecting the resultant to decarboxylation to give the compound (II). Specific examples of the halogeno-carbonic acid ester include, methyl chlorocarbonate, ethyl chlorocarbonate, benzyl chlorocarbonate, 2,2,2-trichloroethyl chlorocarbonate, etc. The base and the solvent to be employed are, for example, those mentioned in the process of the compound (IV)→the compound (I-2). For this reaction, a base and a halogeno-carbonic acid ester, each being about equivalent to the compound (V), are used. The reaction temperature usually ranges from about −30° C. to 60° C., and the reaction time is about one minute to two hours. The compound (VIII) is not necessarily isolated, but the decarboxylation reaction proceeds successively under the above-mentioned reaction conditions to obtain the compound (II) at one pot reaction.

Compound (V)→Compound (IX)→Compound (II)

This process is to prepare the compound (II), which comprises allowing a dehydrating agent to act on the compound (V) to give the compound (IX), an acid anhydride, represented by the formula;

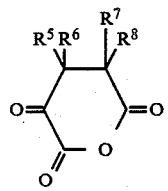 (IX)

followed by allowing alcohol to react with the compound (IX). The examples of the dehydrating agent include halogenides such as phosphorus oxychloride, thionyl chloride and chloride and chlorosulfonic acid; acid anhydrides of lower fatty acid such as acetic anhydride, trifluoroacetic anhydride; acid halides such as acetyl chloride; imidazole derivatives such as N,N'-carbonyl diimidazole, N-trifluoroacetylimidazole; and DCC. When the above acid halide is employed, an organic base such as pyridine and triethylamine used together. This reaction is conducted by employing about equivalent or an excess amount of adehydrating agnet relative to the compound (V) in a solvent. When the dehydrating agent is liquid, it can be used to serve dual purposes of the dehydrating agent and solvent. The solvent to be used is exemplified by dichloromethane, benzene, toluene, acetonitrile, etc. The reaction temperature ranges from about 0° C. to about 100° C., and the reaction time is within the range from 15 minutes to 30 hours. Then, the compound (IX) is allowed to react with about equivalent to excess alcohol to give the compound (II). Specific examples of the alcohol include methanol, ethanol, benzyl alcohol, p-nitrobenzyl alcohol, t-butyl alcohol and trimethylsilylethanol. In this reaction, a catalyst such as sulfuric acid, p-toluene sulfonic acid, zinc chloride, sodium acetate, pyridine, 4-dimethyl aminopyridine, 4-pyrrolidinopyridine, triethylamine and calcium carbonate is employed in some instances. The reaction temperature ranged from about 0° C. to about 100° C., and the reaction time is about 10 minutes to 4 days.

Compound (V)→Compound (X)→Compound (XI)→Compound (XII)→Compound (II)

This process is to prepare the compound (II), which comprises subjecting the compound (V) to diesterification to give the compound (X) represented by the formula;

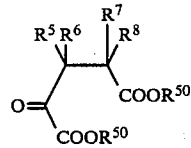 (X)

hydrolyzing selectively the ester group at the 1-position thereof to give the compound (XI) represented by the formula;

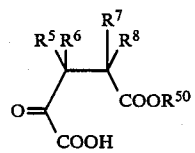 (XI)

introducing into the carboxyl group at its 1-position an ester group which is different from the ester group at its 5-position to give the composition (XII) represented by the formula;

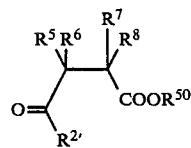 (XII)

then converting selectively the ester group at the 5-position thereof into carboxyl group. Examples of the $R^{50}$ in the above formulae (X), (XI) and (XII) include an alkyl group such as methyl and ethyl or an aralkyl group such as benzyl, p-bromobenzyl and p-nitrobenzyl.

The reaction of "compound (V)→compound (X)" is conducted by using about two to exess amount each of an esterifying agent and a base relative to the compound (V), in the process described above in the preparation of the compound (II). The hydrolysis of "compound (X)→compound (XI)" is usually conducted in a solvent by using a base such as hydroxides, carbonates, alcoholates of alkali metals e.g. lithium, sodium, potassium, cesium, etc. As the solvent, there may be used, among others, water, methanol, ethanol, tetrahydrofuran or dimethyl slfoxide, singly or in combination. This hydrolysis is conducted by employing about equivalent base to the compound (X). The reaction temperature ranges usually from about 0° C. to about 80° C., and the reaction time is about 10 minutes to 20 hours. The esterification "(XI)→(XII)" can be conducted by a process analogous to that for preparing the compound (II) from the compound (V) mentioned above. Depending on cases, the compound (XI) is allowed to react with isobutene in the presence of an acid catalyst. The conversion of the compound (XII) can be performed, when the ester group at the 1-position is stable against the base but the ester group at the 5-position is not (for example, the case where $R^{2'}$=t-butyloxycarbonyl, $R^{50}$=methyl), by applying the above-mentioned process of alkali hydrolysis of "compound (X)→compound (XI)". When the ester group at the 1-position is stable against reduction conditions and the ester group at the 5-position is not (for example, where $R^{2'}$=t-butyloxycarbonyl, $R^{50}$=benzyl), half-ester compounds [compound II] can be obtained selectively by means of reduction. As the method of reduction, there may be counted, among others, catalytic reduction using a metal catalyst e.g. palladium-carbon, palladium black, palladium-barium carbonate, platinum oxide, platinum black and Raney nickel, or a method using a metal e.g. zinc, iron and chromium together with an acid e.g. hydrochloric acid, formic acid and acetic acid. The reduction is conducted usually in a solvent e.g. water, methanol, ethanol, ethyl acetate, acetone or the above-mentioned acids. The reaction temperature ranges usually from about 0° C. to about 60° C., and the reaction time is about 10 minutes to 20 hours.

Compound (XIII)→Compound (XIV)→Compound (XV)→Compound (XVI)→Compound (XII)→Compound (II)

This process is to prepare the compound (II), which comprises subjecting the compound (XIII) represented by the formula;

to esterification to give the compound (XIV) represented by the formula;

subjecting the compound (XIV) to hydrolysis to give the compound (XV) represented by the formula;

subjecting the compound (XV) to esterification again to give the compound (XVI) represented by the formula;

subjecting the hydroxyl group of the compound (XVI) to oxidation to give the compound (XII) (described above), then subjecting this compound to the above-mentioned reaction of "the compound (XII)→the compound (II)".

Among the starting compounds (XIII), those wherein $R^5=R^6=R^7=R^8=H$ are known by a literature reference and can be prepared easily from glutamic acid [cf. M. Taniguchi et al., Tetrahedron, 30, 3547 (1974)]. Compounds having substituents at $R^5\sim R^8$ can be synthesized also by a process analogous to the above. The esterification "the compound (XIII)→the compound (XIV)" is conducted by a similar process to that for preparation of the compound (II) from the compound (V) as described above. In some instances t-alkyl ester is prepared by subjecting the compound (XIII) to addition reaction with an alkene e.g. isobutene in the presence of a catalyst such as sulfuric acid and boron trifluoride. This reaction is conducted usually in a solvent such as dichloromethane, chloroform, dioxane, diethyl ether, tetrahydrofuran and benzene. The reaction is allowed to proceed in a sealed vessel after introducing an excess amount of isobutene. The reaction temperature ranges from about 0° C. to 50° C., and the reaction time is about 5 hours to about several days. The hydrolysis of the compound (XIV) to the compound (XV) by the use of an alkali can be performed by applying the process described above for the preparation of the compound (XI) from the compound (X). For conducting this reaction, it is required to choose the compound (XIV) whose ester group is relatively stable against alkali (e.g. $R^{2'}$=t-butyloxycarbonyl). The esterification "the compound (XV)→the compound (XVI)" can be conducted by a similar process to that for preparation of the compound (VII') from the compound (VII) as described above. The oxidation "the compound (XVI)→the compound (XII)" is conducted by subjecting the compound (XVI) to the treatment with an oxidizing agent in a solvent. Examples of the oxidizing agent include potassium permanganate, manganese dioxide, dimethyl sulfoxide (DMSO)-DCC, DMSO-oxalyl chloride, and DMSO-phospharus pentachloride. As the solvent, there are employed dichloromethane, chloroform, acetonitrile, ethyl acetate, benzene, toluene, DMSO, N,N-dimethylformamide, acetone, ether, etc. In the reaction, the oxidizing agent is used in an amount of usually about equivalent or in excess relative to the compound (XVI). The reaction temperature ranges from about −80° C. to about 60° C., and the reaction time is about 10 minutes to 30 hours.

The compound (II) wherein $R^{2'}$ is amidated carboxyl group can be prepared by applying to the compound (XI) the above-mentioned amidation process of carboxylic acid, followed by a process analogous to that for preparation of the compound (II) from the compound (XII) described as above.

The compound (V), which is the starting compound employed for the present invention can be prepared by various processes already reported. Some of the compounds (V) are known by, for example, the literature references set forth as below, and others can be prepared by processes analogous to those described thereon.

(1) Organic Synthesis, Collective vol. 3, 510 (1955)
(2) M. E. E. Blaise et al., Bulletin de la Societe Chimique de France, 9, 458 (1911)
(3) W. H. Perkin et al., Journal of the Chemical Society, 79 729 (1901)
(4) J. C. Bardhan, Journal of the Chemical Society, 1928, 2591
(5) W. N. Haworth et al., Journal of the Chemical Society, 105, 1342 (1914)
(6) F. C. Hartman, Biochemistry 20 894 (1981)
(7) G Hasse et al., Annalen der Chemie, 697, 62 (1966)

The compound wherein $R^5$=H, for example, can be prepared in accordance with e.g. the following reaction scheme.

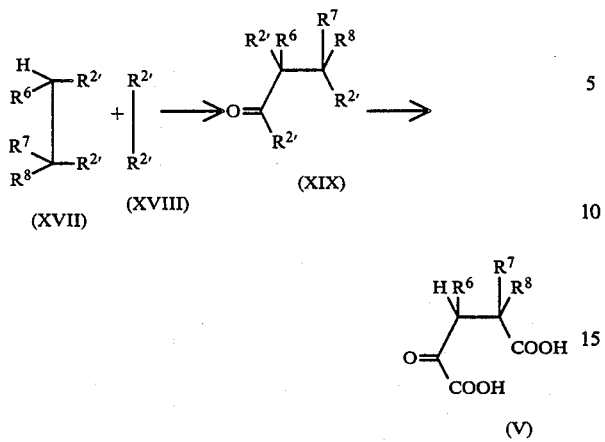

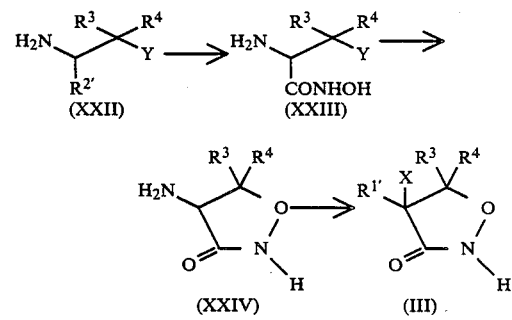

In the above formulae, $R^{2'}$, $R^6$, $R^7$ and $R^8$ are as defined above.

Conversion of the compound (XVII) to the compound (XIX) is a well-known reaction as so-called "Claisen condensation", and is a process of subjecting the compound (XVII) and the compound (XVIII) to condensation in a solvent in the presence of a base. Examples of the base to be employed for this reaction include alkali metal e.g. lithium, sodium and potassium; alkaline earth metal e.g. magnesium and calcium; hydrides, alcoholates, amides and alkyl metals thereof; or quaternary ammonium salts (e.g. tetra-n-butyl ammonium hydroxide). Examples of the solvent include alcohols e.g. methanol and ethanol (when alcoholate is used, the same alcohol as the alkoxyl group of the ester), ether, tetrahydrofuran, dioxane, N,N-dimethyformamide, 1,2-dimethoxyethane, dichloromethane, benzene, toluene, etc.

The reaction temperature ranges usually from about 0° C. to about 80° C., and the reaction time is about 10 minutes to 10 hours.

The conversion "the compound (XIX)→the compound (V)" is a process of preparing the compound (V) by conducting acid, alkali or reductive treatment. This reaction can be carried out analogously to the afore-mentioned processes, for example, the compound (X)→the compound (XI) or the compound (XII)→the compound (II).

The compound (III), the counter-part of the starting materials employed in the present invention, can be prepared by various known processes. The compound (III) is per se known by literature references as set forth below or can be prepared by processes analogous to those described thereon.

(1) Pl. A. Plattner et al., Helvetica Chimica Acta 40, 1531 (1957)
(2) C. H. Stammer et al., Journal of the American Chemical Society 79, 3236 (1957)
(3) C. H. Stammer et al., Journal of the Medicinal Chemistry 21, 709 (1978) The compound (III) (X=H) can be prepared by, for example, the following reaction scheme.

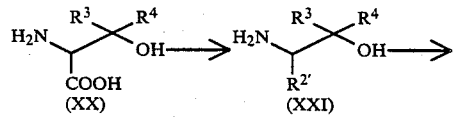

[symbols in the reaction scheme are of the same meaning as defined above]. The esterification "the compound (XX)→the compound (XXI)" can be performed by various conventional esterification processes, for example, a process analogous to the afore-mentioned esterification processes. Among them, treatment with thionyl chloride in alcohol is preferable. In this case, the amino group may sometimes form a salt as e.g. hydrochloride, but it does not at all affect the reaction adversely. The reaction "the compound (XXI)→the compound (XXII)" is a process of converting the hydroxyl group to the leaving group Y. This conversion can be performed by a process analogous to the reaction "the compound (II)→the compound (IV)". The reaction "the compound (XXII)→the compound (XXIII)→the compound (XXIV)" is a process of preparing the compound (XXII) by allowing hydroxylamine to react with the compound (XXII) in the presence of a base. Thus-prepared compund (XXIII) can be isolated, but it can be converted at one pot to the compound (XXIV) without isolation from the reaction system. This reaction is usually conducted by using water as the solvent, and by allowing about equivalent or a little excess amount of hydroxylamine to react with the compound (XVII) in the presence of about equivalent or excess amount of a base relative to the compound (XXII). As the base, use is made of, for example, hydroxides and carbonates of an alkali metal such as lithium, sodium, potassium and cesium, or of an alkaline earth metal such as magnesium and calcium. The reaction temperature ranges normally from about −20° C. to 60° C., and the reaction time is about 10 minutes to 10 hours.

The compound (XXIV) can be subjected to the next reaction step without isolation and purification.

The reaction "the compound (XXIV)→the compound (III)" is a process of preparing the compound (III) by modifying the amino group of the compound (XXIV) into an organic residue bonded through nitrogen. This reaction can be conducted similarly to the process of converting the compound (I-3) to the compound (I-2).

The compound (III) wherein X is methoxy can be prepared also by subjecting the compound (III) whose X is hydrogen to methoxylation or formylamination. The methoxylation and formylamination can be conducted similarly to the reaction in case, as mentioned above, where the compound (I') whose X is hydrogen is subjected to methoxylation or formylamination. Incidentally, when the compound (III) whose X is hydrogen is subjected to formylamination, the said compound (III) is first led to an imine derivative represented by the general formula;

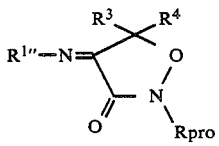

wherein $R^{1''}$, $R^3$ and $R^4$ are of the same meaning as defined above, and Rpro means a protecting group, followed by allowing a nucleophilic derivative of formamide to react therewith. As the protecting group representable by Rpro are mentioned those which were exemplified as the amino-protecting group in the foregoing. The reaction can be conducted similarly to the reaction of subjecting the compound (I') whose X is hydrogen to formylamination as described above.

Various intermediates obtained thus above can be isolated by per se known means such as concentration, pH adjustment, solvent extraction, lyophilization, crystallization, recrystallization, fractional distillation and chromatography.

Thus-obtained compounds (II), (III) and (IV) are useful as starting compounds for preparing for example the compound (I').

The compound (I') thus obtained is useful as a drug, having antimicrobial activity against some species of gram-positive and gram-negative bacteria. Typical compounds of the compound (I') demonstrate antimicrobial spectra against different microorganisms as shown in Table 1.

TABLE 1

| Test microorganism | Minimum growth inhibitory concentration (μg/ml)* Compound (25)** |
|---|---|
| *Straphylococcus aureus* FDA 209P | 6.25 |
| *Escherichia coli* NIHJ JC-2 | 3.13 |
| *Klebsiella pneumoniae* DT | 3.13 |
| *Pseudomonas aeruginosa* IFO 3455 | >100 |

*Medium, Trypticase soy agar
Amount of a bacterium inoculated, $10^8$ CFU/ml
**The compound (25) means the compound (25) prepared in Example 25.

The compound (I') is of low toxicity.

As described above, the compound (I') of this invention and its salts have antimicrobial activity against some species of gram-positive and gram-negative bacteria, and they can be used, as a therapeutic agent for bacterial infections or an antibiotic agent, for the treatment of bacterial infections (e.g., respiratory tract infections, urinary tract infections, suppurative diseases, bile duct infections, intratestinal infections, gynecological infections, surgical infections, etc.) in mammals (e.g., mouse, rat, dog, pig, cattle, human being) caused by infections with bacteria.

The daily doses of the compound (I') or its salt is in the amount of about 2 to 100 mg/kg as the compound (I'), preferably about 5 to 50 mg/kg, more preferably about 5 to 40 mg/kg.

For administration of the compound (I'), the compound (I') or its pharmacologically acceptable salt can be formulated by the conventional means with suitable, pharmacologically acceptable carrier, excipient and diluent into such dosage forms as tablet, granule, capsule or troche to administer orally, and also can be processed into injectable agent by the conventional means, followed by incorporation into a sterile carrier prepared by the conventional means to administer parenterally.

In producing the above-described oral pharmaceutical preparations, such as tablets, there can suitably be formulated binding agents (e.g., hydroxylpropylcellulose, hydroxypropylmethyl cellulose, macrogol, etc.), disintegrating agents (e.g., starch, carboxymethylcellulose calcium, etc.), excipients (e.g., lactose, starch, etc.), lubricants (e.g., magnesium stearate, talc, etc.) and the like.

In manufacturing non-oral or parenteral pharmaceutical preparations, such as injectable solutions, there can suitably be formulated isotonizing agents (e.g., glucose, D-sorbitol, D-mannitol, sodium chloride, etc.), preservatives (e.g., benzul alcohol, chlorobutanol, methyl p-oxybenzoate, propyl p-oxybenzoate, etc.), buffering agents (e.g., phosphate buffers, sodium acetate buffer, etc.) and the like.

The Reference Examples and Examples are described in the following to illustrate this invention in more detail, but this invention is understood not be limited to these.

In the resins to be used, the ones designated by the abbreviations are defined as follows:
HP-20: Diaion HP-20 (manufactured by Mitsubishi Chemical Industries, Ltd., Japan)
XAD-2: Amberlite XAD-2 (manufactured by Rohm & Haas Co., U.S.A.)

In the NMR data, abbreviations denote the following: s; singlet, d; doublet, dd; doublet of doublets, t; triplet, q; quartet, m; multiplet, b; broad (same in IR spectrum).

REFERENCE EXAMPLE 1

Production of (4S, 5R)-4-benzyloxycarbonylamino-5-methyl-3-isoxazolidinone:

In a sodium chloride-ice bath was cooled 4 ml of an aqueous solution of 1.88 g of sodium hydroxide, to which was added 1.88 g of methyl (2S, 3S)-2-amino-3-chlorobutyrate hydrochloride prepared by the method described in Helvetica Chimica Acta, 40, 1531 (1957), and the mixture was stirred for 30 minutes. The mixture was further stirred for 1.5 hour under ice-cooling, followed by addition of 10 ml of tetrahydrofuran, 5 ml of water and 5 ml of tetrahydrofuran solution of 2.14 ml of carbobenzoxy chloride under ice-cooling in that order, then the whole mixture was stirred for 30 minutes, while keeping the pH at 7.0 by the addition of an aqueous solution of sodium hydrogen carbonate. The reaction solution was adjusted to pH 3.0 by the addition of 30 ml of ethyl acetate. The organic layer was taken and concentrated. The concentrate was dissolved in ethyl acetate, and the solution was subjected to extraction with 30 ml of an aqueous solution of 1.6 g of sodium carbonate (by two installments). The aqueous solution was adjusted to pH 2.5 with 5 N HCl, followed by extraction with ethyl acetate (twice). The organic layer was washed with a saturated saline and dried (over $MgSO_4$), followed by concentration under reduced pressure. To the concentrate was added ether, and the precipitated crystals were collected by filtration to give 1.16 g of the subject compound, m.p. 141–143° C.

I R $\nu_{max}^{KBr}$ cm$^{-1}$: 3300, 1710, 1695, 1680, 1545, 1330, 1250

N M R (90M Hz, C D C $l_3$—$d_6$—D M S O) δ: 1.19(3H,d,J=5Hz), 4.5–5.0(2H,m), 5.11(2H,s), 6.14(1H,d,J=7Hz), 7.34(5H,s)

Elemental analysis for: $C_{12}H_{14}N_2O_4$

Calcd. C, 57.59; H, 5.64; N, 11.19
Found C, 57.67; H, 5.52; N, 10.94

REFERENCE EXAMPLE 2

Production of (4S,5R)-4-benzyloxycarbonylamino-5-methyl-3-isoxazolidinone:

In 30 ml of dichloromethane was suspended 5.09 g of L-allothreonine. To the suspension was added 6.56 g of phosphorus pentachloride little by little under ice-cooling with stirring, then the reaction was allowed to proceed at room temperature for 2 hours. The solvent was then evaporated off under reduced pressure. Crystals then precipitated were collected and washed with ethyl acetate to give 5.6 g of methyl (2S, 3R)-2-amino-3-chlorobutyrate hydrochloride. This product was subjected to reaction similar to the procedure in Reference Example 1 to give 1.86 g of the subject compound as colourless crystals, m.p. 127–128° C.

I R $\nu_{max}^{KBr}$ cm$^{-1}$: 1735, 1695, 1540, 1295, 1250, 1055

N M R (90M Hz, C D C l$_3$)δ: 1.46(3H,d,J=5Hz), 4.0–4.6(2H,m), 5.11(2H,s), 5.75(1H,bs), 7.34 (5H,s), 8.8(1H,bs)

Elemental analysis for: $C_{12}H_{14}N_2O_4$:
Calcd. C, 57.59; H, 5.64; N, 11.19
Found C, 57.58; H, 5.55; N, 10.90

REFERENCE EXAMPLE 3

Production of (4R)-4-benzyloxycarbonylamino-3-isoxazolidinone:

To a solution of 1.02 g of (4R)-4-amino-3-isoxazolidinone in 15 ml of tetrahydrofuran and 15 ml of water. To the solution were added 1.25 g of sodium hydrogen carbonate under stirring and ice-cooling. The mixture was stirred for one hour. To the reaction solution was added ethyl acetate, and the aqueous layer was separated. The ethyl acetate layer was subjected to extraction with 5% aqueous solution of sodium carbonate. The extract was combined with the aqueous layer, which was washed with ethyl acetate. The aqueous layer was adjusted to pH 3 to 4 with 1N HCl, followed by extraction with ethyl acetate. The extract solution was washed with water and dried (Na$_2$SO$_4$). Then, the solvent was evaporated off to give 1.80 g of the subject compound as colorless crystals, m.p. 133–134° C.

I R $\nu_{max}^{Nujol}$ cm$^{-1}$: 3325, 1700, 1550, 1310, 1280

N M R (90M Hz, C D C l$_3$—d$_6$—D M S O)δ: 4.03(1H,m), 4.67(2H,m), 5.10(2h,s), 6.0(1H,b), 7.33(5H,s)

REFERENCE EXAMPLE 4

Production of (4S)-4-benzyloxycarbonylamino-3-isoxazolidinone:

By following the procedure of Reference Example 3 for producing (4R)-4-benzyloxycarbonylamino-3-isoxazolidinone, while employing (4S)-4-amino-3-isoxazolidinone instead of (4R)-4-amino-3-isoxazolidinone, the reaction was conducted to give the subject compound, m.p. 135–136.5° C. IR and NMR spectra of this compound were in agreement with those of the compound obtained in Reference Example 3.

REFERENCE EXAMPLE 5

Production of (4S)-4-(4-nitrobenzyloxycarbonylamino)-3-isoxazolidinone:

By a procedure analogous to Reference Example 3 for producing (4R)-4-benzyloxycarbonylamino-3-isoxazolidinone, while employing (4S)-4-amino-3-isoxazolidinone in place of (4R)-4-amino-3-isoxazolidinone, 4-nitrobenzyloxycarbonyl chloride in place of benzyloxycarbonyl chloride, the reaction was conducted to give the subject compound as colorless crystals, m.p. 160–161° C.

I R $\nu_{max}^{Nujol}$ cm$^{-1}$: 3280, 1705, 1550, 1520, 1350, 1275, 1100

N M R (90M Hz, C D C l$_3$—d$_6$—D M S O)δ: 4.07(1H,dd.J=11,15Hz), 4.65(2H,m), 5.21(2H,s), 6.6(1H,b), 7.53(2h,d,J=9Hz), 8.21(2H,d,J=9Hz)

Elemental analysis for: $C_{11}H_{11}N_3O_6$
Calcd. C, 46.98; H, 3.94; N, 14.94
Found C, 47.20; H, 3.89; N, 14.93

REFERENCE EXAMPLE 6

Production of (4S*, 5R*)-2-benzyloxycarbonyl-4-benzyloxycarbonylamino-5-methoxycarbonyl-3-isoxazolidinone [Compound (R-6-A)] and (4S*, 5S*)-2-benzyloxycarbonyl-4-benzyloxycarbonylamino-5-methoxycarbonyl-3-isoxazolidinone [Compound (R-6-B)]:

4-Amino-5-methoxycarbonyl-3-isoxazolidinone synthesized from 1.87 g of diethyl trans-aziridine-2,3-dicarboxylate by the procedure described in Journal of Medicinal Chemistry 21, 709(1978) was dissolved in 10 ml of water and 10 ml of tetrahydrofuran. To the solution was added 0.571 ml of benzyloxycarbonyl chloride while stirring under ice-cooling, and the mixture was stirred for 1 hour, while keeping the pH of the reaction solution at 7.0 with an aqueous solution of sodium hydrogen carbonate. The reaction solution was subjected to extraction with ethyl acetate twice. The extract was washed with a saline solution, dried (MgSO$_4$) and concentrated under reduced pressure. The concentrate was subjected to a silica gel column chromatography, followed by elution with hexane-ethyl acetate (3:2) to give 0.36 g of the subject compound (R-6-A), N M R (90M Hz, C D C l$_3$)δ: 3.76(3H,s), 4.6–5.1(2h,m), 5.10(2H,s), 5.30(2H,s), 5.90(1H,d,J=7Hz), 7.35(5H,s), 7.39(5H,s) and 0.176 g of the subject compound (R-6-B), N M R (90M Hz, C D C l$_3$)δ: 3.61(3H,s), 5.0–5.3(2H,m), 5.13(2H,s), 5.34(2H,s), 5.70(1H,d,J=5Hz), 7.2–7.5(10H,m)

REFERENCE EXAMPLE 7

Production of (4S*, 5R*)-4-benzyloxycarbonylamino-5-methoxycarbonyl-3-isoxazolidinone:

In 30 ml of ethyl acetate was dissolved 0.36 g of (4S*, 5R*)-2-benzyloxycarbonyl-4-benzyloxycarbonylamino-5-methoxycarbonyl-3-isoxazolidinone. To the solution was addes 120 mg of 5% palladium-carbon. The mixture was stirred under ice-cooling in nitrogen streams for 20 minutes. The catalyst was filtered off and washed with ethyl acetate. The filtrate combined with the washing was concentrated. The concentrate was chromatographed on silica gel, followed by elution with hexane-ethyl acetate-acetic acid (50:50:1) to give 150 mg of the subject compound.

I R $\nu_{max}^{KBr}$ cm$^{-1}$: 3340, 1765, 1730, 1695, 1535, 1290, 1245, 1225.

N M R (90 M Hz, C D C l$_3$—(C D$_3$)$_2$C O)δ: 3.74(3H,s), 4.6–5.0(2H,m), 5.10(2H,s), 7.00(1H,broad s), 7.32(5H,s).

REFERENCE EXAMPLE 8

Production of (4S*,5S*)-4-benzyloxycarbonylamino-5-methoxycarbonyl-3-isoxazolidinone:

By using 176 mg of (4S*,5S*)-2-benzyloxycarbonyl-4-benzyloxycarbonylamino-5-methoxycarbonyl-3-isoxazolidinone, the reaction was allowed to proceed analogous to Reference Example 7 to give 54 mg of the subject compound.

I R $\nu_{max}^{KBr}$ cm$^{-1}$: 3300, 1750, 1710 (shoulder). 1690, 1540, 1255, 1225.

N M R (90M Hz, C D C l$_3$—(C D$_3$)$_2$C O)δ: 3.65(3H,s), 4.9–5.4(2H,m), 5.12(2H,s), 6.42(1H.bs), 7.34(5H,s).

REFERENCE EXAMPLE 9

Production of 5-phenyl-4-(2-thienylacetamide)-3-isoxazolidinone:

In a mixture of 12 ml of water and 2 ml of methanol were dissolved 1.6 g of hydroxylamine hydrochloride and 2.3 g of sodium hydroxice. To the solution was added little by little 3.0 g of ethyl 2-amino-3-chloro-3-phenyl propionate hydrochloride under ice-cooling. The mixture was stirred for 2.5 hours. The reaction mixture was neutralized with concentrated hydrochloric acid, to which was added 15 ml of tetrahydrofuran. To the resultant solution was added dropwise a solution of 2.73 g of 2-thiopheneacetyl chloride in 1 ml of tetrahydrofuran under ice-cooling while keeping the pH at 7 with sodium hydrogen carbonate, followed by stirring for one hour under ice-cooling. To the reaction solution was added 30 ml of ethyl acetate. The aqueous layer was made acid with hydrochloric acid, then the organic layer was separated. The aqueous layer was subjected to extraction with ethyl acetate. The organic layers were combined and concentrated. The concentrate was dissolved in an aqueous solution of sodium carbonate, which was subjected extraction with ethyl acetate. The aqueous layer was separated and made acid with hydrochloric acid again, which was subjected to extraction with ethyl acetate. The organic layer was dried (MgSO$_4$), then the solvent was evaporated off. The residue was chromatographed on silica gel column, followed by elution with chloroform-methanol (98:2) to give 613 mg of the subject compound.

I R $\nu_{max}^{KBr}$ cm$^{-1}$: 3300, 1705, 1660, 1510, 740, 690

N M R (90M Hz, C D C l$_3$—d$_6$—D M S O)δ: 3.50(2H.s), 5.05(1H,t,J=8Hz), 5.56(1H,d,J=8Hz), 6.56–7.10(3H,m), 7.21(5H,s), 7.92(1H,d,J=8Hz)

REFERENCE EXAMPLE 10

Production of 5-phenyl-4-(2-phenylacetamido)-3-isoxazolidinone:

By using 4.7 g of ethyl 2-amino-3-chloro-3-phenylpropionate hydrochloride and 4.1 g of phenylacetyl chloride, a reaction analogous to Reference Example 9 was conducted to give 617 mg of the subject compound.

I R $\nu_{max}^{KBr}$ cm$^{-1}$: 3300, 1690, 1640 1495, 1450, 695

N M R (90M Hz, C D C l$_3$—d$_6$—D M S O)δ: 3.27(2H,s), 5.00(1H,t,J=7Hz), 5.56(1H,d,J=7Hz), 6.79–7.03(1H,m), 7.16–7.33(10H,bs), 8.27(1H,d,J=7Hz)

REFERENCE EXAMPLE 11

Production of 4-[2-chloroacetamido-4-thiazolyl)-(Z)-2-(methoxyimino)acetamido]-5-phenyl-3-isoxazolidinone:

Employing 3.0 g of ethyl 2-amino-3-chloro-3-phenylpropionate hydrochloride and 5.67 g of 2-(2-chloroacetamido-4-thiazolyl)-(Z)-2-(methoxyimino) acetyl chloride hydrochloride, a reaction was allowed to proceed by the procedure to Reference Example 9 to give 420 mg of the subject compound.

I R $\nu_{max}^{KBr}$ cm$^{-1}$: 1680, 1540, 1450, 690

N M R (90M Hz, C D C l$_3$—d$_6$—D M S O)δ: 3.92(3H,s), 4.29(2H,bs), 5.19(1H,t,J=8Hz), 5.68(1H,d,J=8Hz), 7.33(5H,s), 7.69(1H,s), 8.36(1H,d,J=8Hz)

REFERENCE EXAMPLE 12

Production of (4S)-4-(2-thienylacetamido)-3-isoxazolidinone:

Employing methyl (2S)-2-amino-3-chloropropionate hydrochloride, a reaction was allowed to proceed by the procedure of Reference Example 9 to give the subject compound.

I R $\nu_{max}^{KBr}$ cm$^{-1}$: 3300, 1720, 1660, 1520, 1250, 1100

N M R (90M Hz, C D Cl$_3$—C D$_3$O D)δ: 3.72–4.13(5H,m), 4.59–4.91(2H,m), 6.90–7.29(3H,m)

EXAMPLE 1

Production of 1-(4-nitrobenzyl) 2-oxoglutarate [Compound (1)]:

(a) To 20 ml of N,N-dimethylformamide solution of 2.93 g of 2-oxoglutaric acid was added 3.63 g of dicyclohexylamine. The mixture was heated to 50° C., to which was added 4.75 g of 4-nitrobenzyl bromide, followed by stirring at 70° C. for 15 minutes. The reaction mixture was cooled, to which was added 100 ml of ethyl acetate. The crystals which separated out were filtered off, and washed with ethyl acetate. The filtrate and the washing were combined, washed with water and a saturated saline solution, followed by drying (MgSO$_4$). The solvent was concentrated under reduced pressure. The concentrate was subjected to a silica gel column chromatography, followed by elution with hexane-ethyl acetate-acetic acid (50:50:1) to give 5.2 g of the subject Compound (1) as crystals, m.p. 100–102° C.

I R $\nu_{max}^{KBr}$ cm$^{-1}$: 1735, 1707, 1530, 1345, 1275, 1085

N M R (90M Hz, C D C l$_3$—d$_6$—D M S O)δ: 2.5–2.8(2H,m), 2.9–3.3(2H,m), 5.40(2h,s), 7.62(2H,d,J=9Hz), 8.28(2H,d,J=9Hz)

Elemental analysis for: C$_{12}$H$_{11}$NO$_7$
Calcd. C, 51.25; H, 3.94; N, 4.98
Found C, 51.17; H, 3.92; N, 4.96

(b) To 20 ml of N,N-dimethylformamide solution of 2.93 g of 2-oxoglutaric acid were added 2.79 ml of triethyl amine and then 4.53 g of 4-nitorbenzyl bromide. The mixture was stirred at room temperature for 5 hours. The reaction solution was poured into ice-water, which was subjected to extraction with ethyl acetate (twice), then by following the procedure of Example 1(a), there was obtained 3.6 g of the subject Compound (1).

(c) To 30 ml of N,N-dimethylformamide suspension of 3.36 g of monosodium 2-oxoglutarate was added 4.53 g of 4-nitrobenzyl bromide. The mixture was stirred at 50–60° C. for 2 hours. The reaction solution was poured into ice-water, which was subjected to extraction with ethyl acetate (twice), then by following the procedure of Example 1(a), there was obtained 3.92 g of the subject Compound (1) as crystals.

EXAMPLE 2

Production of 4-nitrobenzyl 2-[(4S,5R)-4-benzyloxycarbonylamino-5-methyl-3-oxo-2-isoxazolidinyl]-5-oxo-2-tetrahyrdofuran carboxylate [Compound (2)]:

In 5 ml of dichloromethane were dissolved 125 mg of (4S,5R)-benzyloxycarbonylamino-5-methyl-3-isoxazolidinone and 155 mg of Compound (1) obtained in Example 1. To the solution was added 114 mg of N,N'-dicyclohexylcarbodiimide (DCC). The mixture was stirred at room temperature for 30 minutes. The crystals which separated out were filtered off, and washed with dichloromethane. The filtrate and the washing were combined and concentrated under reduced pressure. The concentrate was subjected to a silica gel column chromatography, followed by elution with hexane-ethyl acetate (1:1) to give 185 mg of the subject Compound (2) as colorless foamy substance.

IR $\nu_{max}^{Neat}$ cm$^{-1}$: 3325, 1805, 1770(shoulder), 1730, 1530, 1350, 1050

NMR (90M Hz, CDCl$_3$)δ: 1.17, 1.23(each 1.5H,d,J=6Hz), 2.3–3.3(4H,m), 4.6–5.1(2H,m), 5.10(2H,s), 5.37(2H,s), 5.48(1H,d,J=5Hz), 7.33(5H,s), 7.51, 8.20(each 2H,d,J=9Hz)

EXAMPLE 3

Production of sodium 2-[(4S,5R)-4-(2-thienylacetamido)-5-methyl-3-oxo-2-isoxazolidinyl]-5-oxo-2-tetrahydrofurancarboxylate [Compound (3)]:

In a mixture of 5 ml of ethyl acetate and 5 ml of water was dissolved 185 mg of Compound (2). To the solution was added 200 mg of 5% palladium-carbon. The mixture was stirred at room temperature for 50 minutes in hydrogen streams. The catalyst was filtered off and washed with water. The filtrate and the washing were combined. The aqueous layer was taken, to which 5 ml of tetrahydrofuran was added. To the mixture were added under ice-cooling and stirring 67 μl of 2-thiophene acetyl chloride and an aqueous solution of sodium hydrogen carbonate. The reaction was allowed to proceed for 30 minutes while keeping the pH around 7.0. Tetrahydrofuran was evaporated off under reduced pressure. The resulting aqueous solution was washed with ethyl acetate, and the aqueous layer was purified by means of an XAD-2 column. The fractions eluted with water were lyophilized to give 87 mg of the subject Compound (3) as pale yellow powder.

IR $\nu_{max}^{KBr}$ cm$^{-1}$: 1775, 1720, 1655, 1380, 1195

NMR (90M Hz, CDCl$_3$—d$_6$—DMSO)δ: 1.08(3H,d,J=6Hz), 2.2–3.3(4H,m), 3.76(2H,s), 4.4–5.0(2H,m), 6.8–7.4(3H,m), 8.81, 8.85(each 0.5H,d,J=8Hz)

Elemental analysis for: C$_{15}$H$_{15}$N$_2$NaO$_7$S
Calcd. C, 44.12; H, 4.20; N, 6.86
Found C, 44.35; H, 4.23; N, 6.82

EXAMPLE 4

Production of sodium 2-{(4S,5R)-4-[2-(2-amino-4-thiazolyl)-(Z)-2-(methoxyimino)acetamido]-5-methyl-3-oxo-2-isoxazolidinyl}-5-oxo-2-tetrahydrofurancarboxylate [Compound (4)]:

In a mixture of 5 ml of ethyl acetate and 5 ml of water was dissolved 257 mg of the Compound (2) obtained in Example 2. To the solution was added 250 mg of 5% palladium-carbon, and the mixture was stirred at room temperature for 45 minutes in hydrogen streams. The catalyst was filtered off and washed with water. The filtrate and the washing were combined, and the aqueous layer was taken, to which 10 ml of tetrahydrofuran was added. To the mixture were added, under ice-cooling and stirring, 217 mg of 2-(2-chloroacetamido-4-thiazoly)-(Z)-2-methoxyiminoacetyl chloride hydrochloride and an aqueous solution of sodium hydrogen carbonate. The reaction was allowed to proceed while keeping the pH around 7.0, followed by addition of 165 mg of sodium N-methyldithiocarbamate. The mixture was stirred at room temperature for 45 minutes, then tetrahydrofuran was evaporated off under reduced pressure. The concentrate was washed with ethyl acetate, followed by purification by means of an XAD-2 column. The fractions eluted with water were lyophilized to give 149 mg of the subject Compound (4) as yellow powder.

IR $\nu_{max}^{KBr}$ cm$^{-1}$: 1775, 1720, 1660, 1535, 1380, 1040

NMR (90M Hz, CDCl$_3$—d$_6$—DMSO)δ: 1.21(3H,d,J=6Hz), 2.2–3.3(4H,m), 3.86(3H,s), 4.5–5.1(2H,m), 6.72(1H,s), 7.07(2H,s), 9.02, 9.19(each 0.5H,d,J=8Hz)

Elemental analysis for: C$_{15}$H$_{16}$N$_5$NaO$_8$S·1.5H$_2$O
Calcd. C, 37.82; H, 4.02; N, 14.07
Found C, 38.01; H, 4.07; N, 14.76

EXAMPLE 5

Production of 4-nitrobenzyl 2-[(4S,5S)-4-benzyloxycarbonylamino-5-methyl-3-oxo-2-isoxazolidinyl]-5-oxo-2-tetrahydrofurancarboxylate [Compound (5)]:

Employing 376 mg of (4S,5S)-4-benzyloxycarbonylamino-5-methyl-3-isoxazolidinone obtained in Reference Example 2 and 464 mg of the Compound (1) obtained in Example 1, the reaction was allowed to proceed by the procedure of Example 2 to give 593 mg of the subject Compound (5) as colorless foamy substance.

IR $\nu_{max}^{Neat}$ cm$^{-1}$: 3350, 1805, 1760(shoulder), 1730, 1530, 1350, 1185, 1055

NMR (90M Hz, CDCl$_3$)δ: 1.38, 1.42(each1.5H,d,J=5Hz), 2.2–3.3(4H,m), 4.0–4.7(2H,m), 5.07(2H,s), 5.32(2H,s), 5.57(1H,d,J=7Hz), 7.31(5H,s), 7.47, 7.50(each 1H,d,J=11Hz), 8.16(2H,d,J=11Hz)

EXAMPLE 6

Production of sodium 2-[(4S,5S)-4-(2-thienylacetamido)-5-methyl-3-oxo-2-isoxazolidinyl]-5-oxo-2-tetrahydrofurancarboxylate [Compound (6)]:

Employing 265 mg of the Compound (5) obtained in Example 5, the reaction was allowed to proceed by the procedure of Example 3 to give 162 mg of the subject Compound (6) as colorless powder.

IR $\nu_{max}^{KBr}$ cm$^{-1}$: 1780, 1730, 1655, 1380, 1200

NMR (90M Hz, CDCl$_3$—d$_6$—DMSO)δ: 1.28(3h,d,J=6Hz), 2.2–3.3(4H,m), 3.73, 3.75(each 1H,s), 4.0–4.8(2H,m), 6.8–7.3(3H,m), 8.77(1H,d,J=8Hz)

EXAMPLE 7

Production of sodium 2-{(4S,5S)-4-[2-(2-amino-4-thiazolyl)-(Z)-2(methoxyimino)acetamido]-5-methyl-3-oxo-2-isoxazolidinyl}-5-oxo-2-tetrahydrofurancarboxylate [Compound (7)]

Employing 257 mg of the Compound (5) obtained in Example 5, the reaction was allowed to proceed by the procedure of Example 4 to give 149 mg of the subject Compound (7) as pale yellow powder.

IR $\nu_{max}^{KBr}$ cm$^{-1}$: 1785, 1730, 1655, 1530, 1380, 1200, 1035

NMR (90M Hz, CDCl$_3$—d$_6$—DMSO)δ: 1.36(3H,d,J=6Hz), 2.1–3.3(4H,m), 3.87(3H,s), 4.1–4.9(2H,m), 6.89, 6.92(each 0.5H,s), 7.13(2H,s), 9.06, 9.08(each 0.5H,d,J=8Hz)

EXAMPLE 8

Production of 4-nitrobenzyl 2-[(4R)-4-benzyloxycarbonylamino-3-oxo-2-isoxazolidinyl]-5-oxo-2-tetrahydrofurancarboxylate [Compound (8)]:

(a) In 3 ml of dichloromethane were dissolved 85 mg of the Compound (1) obtained in Example 1 and 41 mg of 1-hydroxybenzotriazole (HOBT). To the solution was added 62 mg of DCC, and the mixture was stirred at room temperature for 30 minutes, to which was added 60 mg of (4R)-4-benzyloxycarbonylamino-3-isoxazolidinone, prepared by the method described in Journal of Medicinal Chemistry, 13 1013 (1970), followed by stirring at room temperature for 30 minutes. The insolubles which separated out were filtered off and washed with dichloromethane. The filtrate and the washing were combined and concentrated. The concentrate was dissolved in ethyl acetate. The solution was washed with an aqueous solution of sodium hydrogen carbonate and a saturated saline, successively, which was then dried (Na$_2$SO$_4$). The solvent was evaporated off under reduced pressure, and the residue was subjected to a silica gel column chromatography, followed by elution with hexane-ethyl acetate (1:1) to give 96 mg of the subject compound (8) as colorless foamy substance.

IR $\nu_{max}^{Neat}$ cm$^{-1}$: 3330, 1805, 1760(shoulder), 1730, 1530, 1350, 1270, 1245, 1185, 1055

NMR (90M Hz, CDCl$_3$)δ: 2.3–3.4(4H,m), 4.0–4.4(1H,m), 4.4–5.1(2H,m), 5.11(2H,s), 5.36(2H,s), 5.53, 5.59(each 0.5H,d,J=6Hz), 7.33(5H,s), 7.50, 7.52(each 1H,d,J=9Hz), 8.18(2H,d,J=9Hz)

Mass Spectrum m/e:4 9 9 M$^+$)

(b) In 2 ml of dichloromethane were dissolved 85 mg of Compound (1) and 60 mg of (4R)-4-benzyloxycarbonylamino-3-isoxazolidinone. To the solution were added 77 mg of 2-chloro-1-methylpyridinium iodide and 84 μl of triethylamine. The mixture was stirred at room temperature for 40 minutes, followed by concentration under reduced pressure. The residue was dissolved in ethyl acetate, followed by conducting workup similar to that in Example 8(a) to give 31 mg of the subject Compound (8).

EXAMPLE 9

Production of 4-nitrobenzyl 2-[(4S)-4-benzyloxycarbonylamino-3-oxo-2-isoxazolidinyl]-5-oxo-2-tetrahydrofurancarboxylate [Compound (9)]:

(a) In 20 ml of dichloromethane were dissolved 236 mg of (4S)-4-benzyloxycarbonylamino-3-isoxazolidinone obtained in Example 4 and 365 mg of the Compound (1) obtained in Example 1. To the solution was added 277 mg of DCC, followed by stirring at room temperature for 14 hours. The crystals which separated out were filtered off and washed with dichloromethane. The filtrate combined with the washing was washed with an aqueous solution of sodium hydrogen carbonate then with water, and dried (Na$_2$SO$_4$). Then the solvent was evaporated off, and the residue was subjected to a silica gel column chromatography, followed by elution with hexane-ethyl acetate (1:1) to give 297 mg of the subject Compound (9) as colorless foamy substance.

IR $\nu_{max}^{Neat}$ cm$^{-1}$: 3350, 1800, 1770–1700, 1520, 1340, 1260, 1230, 1180, 1050

NMR (90M Hz, CDCl$_3$)δ: 2.3–3.3(4H,m), 4.1(1H,m), 4.5–4.8(2H,m), 5.11(2H,s), 5.3(1H,b), 5.37(2H,s), 7.35(5H,s), 7.53(2H,d,J=9Hz), 8.23(2H,d,J=9Hz) Mass Spectrum m/e:4 9 9 (M$^+$)

(b) In 10 ml of dichloromethane was dissolved 282 mg of Compound (1), and the solution was cooled on a sodium chloride-ice bath, to which were added 140 μl of triethylamine and 96 μl of ethyl chlorocarbonate. To the mixture was added 119 mg of (4S)-4-benzyloxycarbonylamino-3-isoxazolidinone. The mixture was stirred for one hour under ice-cooling and for one hour at room temperature. The solvent was evaporated off under reduced pressure. The residue was subjected to extraction with ethyl acetate, and the organic layer was washed with an aqueous solution of sodium hydrogen carbonate, then with a saturated saline solution, followed by drying (MgSO$_4$). Then, the solvent was evaporated off, and the residue was subjected to a silica gel chromatography, followed by elution with 1,2-dichloroethane-ethyl acetate (9:1), then with hexane-ethyl acetate (1:1) to give 73 mg of the subject Compound (9).

(c) In 5 ml of dichloromethane were dissolved 155 mg of Compound (1) and 119 mg of (4S)-4-benzyloxycarbonylamino-3-isoxazolidinone. To the solution were added two drops of boron trifluoride etherate (47% ether solution) and 2 g of Molecular Sieves (3A). The mixture was allowed to stand at room temperature for 2 days. The reaction solution, after removing the Molecular Sieves, was washed with a cooled aqueous solution of sodium hydrogen carbonate, followed by drying (MgSO$_4$). The solvent was evaporated off under reduced pressure, and the residue was purified by subjecting to a silica gel preparative thin-layer chromatography [developed with 1,2-dichloroethane-ethyl acetate (5:1)] to give 12.5 mg of the subject Compound (9).

EXAMPLE 10

Production of 1-methyl 2-oxoglutarate [Compound (10)]:

In 100 ml of N,N-dimethylformamide was dissolved 27.93 g of 2-benzyloxycarbonylamino-5-oxo-2-tetrahydrofurancarboxylic acid obtained by the method described in Journal of Organic Chemistry, 6 878 (1941). To the solution was added 4.0 g of sodium hydride (60% oil), to which was further added 28.4 of methyl iodide, and the reaction was allowed to proceed at room temperature for 4 hours. The reaction mixture was supplemented with 14.2 g of methyl iodide, which was stirred for further 3 hours. The reaction solution was poured into water, which was subjected to extraction with ethyl acetate. The organic layer was washed with sodium hydrogen carbonate and a saturated saline solution, successively, followed by drying (MgSO$_4$). The solvent was evaporated off, and the crystals which separated out were collected by filtration, followed by washing with ether to give 27.25 g of methyl 2-benzyloxycarbonylamino-5-oxo-2-tetrahydrofurancarboxylate as colorless crystals, m.p. 134–134.5° C.

IR $\nu_{max}^{KBr}$ cm$^{-1}$: 3295, 1780, 1758, 1700, 1540, 1308, 1196, 1049

To 10.0 g of this compound was added 20 ml of 30% hydrobromic acid solution, and the mixture was stirred for 30 minutes. The reaction mixture was washed (decantation) twice with 500 ml (twice) of hexane-ether (9:1) under ice-cooling. To the resultant was added water, and the mixture was subjected to extraction (4 times) with ethyl acetate. The organic layer was washed with a saturated saline solution and dried (MgSO$_4$), then the solvent was evaporated off. The residue was subjected to a silica gel column chromatography, followed by elution with hexane-ethyl acetate (1:1) to give 2.95 g of the subject Compound (10) as colorless crystals, m.p. 54.5–55.0° C.

IR $\nu_{max}^{KBr}$ cm$^{-1}$: 3430, 1750, 1735, 1710, 1275, 1255, 1225, 1080

NMR (90M Hz, CDCl$_3$)δ: 2.60–3.27(4H,m), 3.88(3H,s), 8.20(1H,bs)

Elemental analysis for: C$_6$H$_8$O$_5$
Calcd. C, 45.01; H, 5.04
Found C, 44.92; H, 4.92

EXAMPLE 11

Production of 1-(4-nitrobenzyl) 2-oxoglutarate [Compound (1)]:

In 5 ml of N,N-dimethylformamide solution was dissoved 838 mg of 2-benzyloxycarbonylamino-5-oxo-2-tetrahydrofurancarboxylic acid. To the solution was added 120 mg of sodium hydride (60% oil). To the mixture was added 648 mg of 4-nitrobenzyl bromide, followed by stirring at room temperature for 2.5 hours. To the reaction solution was added a saturated aqueous solution of sodium hydrogen carbonate, which was subjected to extraction with ethyl acetate. The aqueous layer was then dried (MgSO$_4$), followed by removal of the solvent by evaporation. The residue was subjected to a silica gel column chromatography, followed by elution with hexane-ethyl acetate (1:1) to give 687 mg of 4-nitrobenzyl 2-benzyloxycarbonylamino-5-oxo-2-tetrahydrofurancarboxylate as colorless crystals, m.p. 127–127.5° C.

IR $\nu_{max}^{KBr}$ cm$^{-1}$: 3310, 1780, 1759, 1728, 1520, 1345, 1185, 1042

Employing 2.07 g of this product, the reaction was conducted in a manner similar to that of Example 10 to give 1.14 g of the subject Compound (1). This product was in complete agreement with the Compound (1) obtained in Example 1 in the melting point, IR and NMR spectrum.

EXAMPLE 12

Production of methyl 2-[(4R)-4-benzyloxycarbonylamino-3-oxo-2-izoxazolidinyl]-5-oxo-2-tetrahydrofurancarboxylate [Compound (12)]:

(a) In 8 ml of dichloromethane were dissolved 74 mg of (4R)-4-benzyloxycarbonyamino-3-izoxazolidinone, 50 mg of the Compound (10) obtained in Example 10, 96 mg of 2-chloro-1-methylpyridinium iodide and 103.5 mg of dihydropyridopyrimidone. The solution was stirred at room temperature for 15 hours in nitrogen streams. To the reaction solution was added ethyl acetate, and insolubles which separated out were filtered off. The filtrate was concentrated to dryness. The concentrate was subjected to a silica gel column chromatography, followed by elution with hexane-ethyl acetate (1:1) to give 40.1 mg of the subject Compound (12).

IR $\nu_{max}^{KBr}$ cm$^{-1}$: 3375, 1805, 1740, 1525

NMR (90M Hz, CDCl$_3$)δ: 2.20–3.40(4H,m), 3.75(3H,s), 4.15(1H,m), 4.75(2H,m), 5.13(2H,s), 5.45(1H,bd), 7.34(5H,s)

(b) In 8 ml of dichloromethane were dissolved 82 mg triphenylphosphine and 70 mg of 2,2'-dipyridyl disulfide. The solution was stirred at room temperature for 5 minutes in nitrogen streams, followed by addition of 290 mg of silver chloride and 154 mg of 3,4-dihydro-2H-pyrido[1,2-a]pyrimidin-2-one and by stirring for 5 minutes. To the mixture were added 74 mg of (4R)-4-benzyloxycarbonylamino-3-isoxazolidinone and 50 mg of Compound (10). The whole mixture was stirred at room temperature for 7.5 hours, followed by subjecting the resultant to workup in a manner similar to that in Example 12(a) to give 69.6 mg of the subject Compound (12).

(c) In 8 ml of acetonitrile were dissolved 74 mg of (4R)-4-benzyloxycarbonylamino-3-isoxazolidinone, 50 mg of Compound (10), 50 mg of 3,4-dihydro-2H-pyrido-[1,2-a]pyrimidin-2-one and 90 mg of triphenylphosphine. The solution was stirred at room temperature in nitrogen streams. To the mixture was added 100 μl of carbon tetrachloride, which was stirred for 6 hours, followed by subjecting the resultant to workup similar to that in Example 12(a) to give 46 mg of the subject Compound (12).

(d) In 10 ml of dichloromethane solution were dissolved 74 mg of (4R)-4-benzyloxycarbonylamino-3-isoxazolidinone, 50 mg of Compound (10) and 52 mg of 3,4-dihydro-2H-pyrido[1,2-a]pyrimidin-2-one. To the solution was added 80 μl of diphenylphosphoryl azide at room temperature under stirring in nitrogen streams, then the reaction was allowed to proceed for 20 hours. The reaction solution was concentrated, and the concentrate was subjected to a silica gel column chromatography, followed by elution with hexane-ethyl acetate (1:1) to give 30 mg of the subject Compound (12).

(e) In 8 ml of dichloromethane were dissolved 74 mg of (4R)-4-benzyloxycarbonylamino-3-isoxazolidinone, 50 mg of Compound (10) and 94 mg of 1-ethoxycarbonyl-2-ethoxy-1,2-dihydroquinoline. The solution was stirred for 18 hours in nitrogen streams, followed by subjecting to workup similar to that of the above (d) to give 111 mg of the subject Compound (12).

EXAMPLE 13

Production of methyl 2-chloro-5-oxo-2-tetrahydrofurancarboxylate [Compound (13)]:

(a) A mixture of 80 mg of the Compound (10) obtained in Example 10, 131 mg of triphenylphosphine and 5 ml of carbon tetrachloride was heated under reflux for 4 hours in nitrogen streams. The solvent was evaporated off. The residue was subjected to a flash chromatograph using silica gel, followed by elution with hexane-ethyl acetate (1:2) to give 46 mg of the subject Compound (13) as colorless crystals, m.p. 50.5–51.0° C.

IR $\nu_{max}^{KBr}$ cm$^{-1}$: 1820, 1750, 1175, 1160, 1100, 1075

NMR (90 MHz, CDCl$_3$)δ:2.40–3.23(4H,m), 3.90(3H,s)

Elemental analysis for: C$_6$H$_7$ClO$_4$
Calcd. C,40.36; H,3.95
Found C,40.35; H,3.94

(b) In 10 ml of dichloromethane was dissolved 1.0 g of Compound (10). To the solution were added 911 μl of thionyl chloride and one drop of N,N-dimethylformamide. The mixture was stirred at room temperature for 15 hours. The reaction solution was concentrated. The concentrate was subjected to a flash chromatography using silica gel, followed by elution with hexane-ethyl acetate (1:2) to give 985 mg of the subject Compound (13).

EXAMPLE 14

Production of methyl 2-[(4R)-4-benzyloxycarbonylamino-3-oxo-2-isoxazolidinyl]-5-oxo-2-tetrahydrofurancarboxylate [Compound (12)]:

In 3 ml of N,N-dimethylformamide was dissolved 236 mg of (4R)-4-benzyloxycarbonylamino-3-isoxazolidinone. To the solution was added 326 mg of cesium carbonate. The mixture was stirred at room temperature for 20 minutes, to which was added 179 mg of the Compound (13) obtained in Example 13, followed by stirring for two hours. To the reaction solution was added a dilute saline solution. The mixture was subjected to extraction with ethyl acetate. The organic layer was washed with a saturated saline solution, which was dried ($Na_2SO_4$), then the solvent was evaporated off. The residue was subjected to a silica gel column chromatography, followed by elution with hexane-ethyl acetate (1:1) to give 101 mg of the subject Compound (12). The IR and NMR spectra of this product were in complete agreement with those of the Compound (12) obtained in Example 12.

EXAMPLE 15

Production of 4-nitrobenzyl 2-chloro-5-oxo-2-tetrahydrofurancarboxylate [Compound (15)]:

In 16 ml of 1,2-dichloroethane was dissolved 0.40 g of the Compound (1) obtained in Example 1. To the solution was added 0.88 ml of thionyl chloride. The mixture was heated for 10 hours under reflux. The solvent was evaporated off, and the residue was subjected to a silica gel column chromatography, followed by elution with hexane-ethyl acetate (3:1) to give 0.36 g of the subject Compound (15) as colorless oil.

IR$\nu_{max}^{Neat}$ cm$^{-1}$: 1815,1760,1520,1340,1160,1080
NMR(90 MHz, CDCl$_3$)$\delta$: 2.8(4H,m),5.43 (2H,s),7.60(2H,d,J=9 Hz),8.30(2H,d,J=9 Hz)
Mass Spectrum m/e: 3 0 1 , 2 9 9 (M$^+$)

EXAMPLE 16

Production of 4-nitrobenzyl 2-[(4R)-4-benzyloxycarbonylamino-3-oxo-2-isoxazolidinyl]-5-oxo-2-tetrahydrofurancarboxylate [Compound (8)]:

In 4 ml of dichloromethane was dissolved 60 mg of (4R)-4-benzyloxycarbonylamino-3-isoxazolidinone. To the solution were added under ice-cooling 0.08 ml of diisopropyl ethylamine and 90 mg of the Compound (15) obtained in Example 15. The mixture was stirred for 15 minutes under ice-cooling, followed by stirring at room temperature for 30 minutes. The reaction solution was washed with water, which was dried ($Na_2SO_4$), then the solvent was evaporated off. The residue was subjected to a silica gel column chromatography, followed by elution with hexane-ethyl acetate (1:1) to give 71 mg of the subject Compound (8) as colorless foamy product. The IR and NMR spectra of this product were in agreement with those of the Compound (8) obtained in Example 8.

EXAMPLE 17

Production of sodium 2-{(4R)-4-(2-amino-4-thiazolyl)-(Z)-2-(methoxyimino)acetamido]-3-oxo-2-isoxazolidinyl}-5-oxo-2-tetrahydrofurancarboxylate [Compound (17)]:

In a mixture of 5 ml of ethyl acetate and 7.5 ml of a phosphate buffer solution of pH 7.0 was dissolved 220 mg of the Compound (8) obtained in Example 8. To the solution was added 220 mg of 10% palladium-carbon, and the mixture was stirred for 90 minutes under ice-cooling in hydrogen streams. The catalyst was filtered off and washed with water. The filtrate and the washing were combined, and the aqueous layer was taken, to which was added 5 ml of tetrahydrofuran. To the resultant were added, under ice-cooling and stirring, 110 mg of sodium hydrogen carbonate and 195 mg of 2-(2-chloroacetamido-4-thiazolyl)-(Z)-2-methoxyiminoacetyl chloride hydrochloride. The reaction solution was stirred for 20 minutes, to which was added 110 mg of sodium N-methyl dithiocarbamate. The mixture was stirred at room temperature for 30 minutes. Tetrahydrofuran was evaporated off under reduced pressure. The residue was washed with ethyl acetate, followed by purification by means of an HP-20 column. Fractions eluted with water were lyophilized to give 107 mg of the subject Compound (17) as white powder.

IR$\nu_{max}^{KBr}$ cm$^{-1}$: 1775, 1720, 1650, 1530, 1380,1190,1035
NMR (90 MHz, D$_2$O)$\delta$: 2.6–3.5(4H,m),4.23 (3H,s),4.6(1H,m),5.0(1H,m)5.4(1H,m),7.28(1H,s)
Elemental analysis for: $C_{14}H_{14}NaO_8S \cdot 1.5H_2O$
Calcd. C,36.37; H,3.71; N,15.15
Found C,36.29; H,3.58; N,15.04

EXAMPLE 18

Production of 4-nitrobenzyl 2-[(4S)-4-benzyloxycarbonylamino-3-oxo-2-isoxazolidinyl]-5-oxo-2-tetrahydrofurancarboxylate [Compound 9]:

In 5 ml of dichloromethane was dissolved 118 mg of (4S)-4-benzyloxycarbonylaminoisoxazolidinone obtained in Reference Example 4. To the solution were added, under ice-cooling and stirring, 0.14 ml of triethylamine and 1 ml of dichloromethane solution dissolving 160 mg of the Compound (1) obtained in Example 1. The reaction solution was stirred at room temperature for 30 minutes, which was then washed with water and dried ($Na_2SO_4$). The solvent was evaporated off. The residue was subjected to a silica gel chromatography, followed by elution with hexane-ethyl acetate (1:1) to give 135 mg of the subject compound as colorless foamy product. The IR and NMR spectra of this product were in agreement with those of the Compound (9) obtained in Example 9.

EXAMPLE 19

Production of sodium 2-{(4S)-4-[2-(2-amino-4-thiazolyl)-(Z)-2-(methoxyimino)acetamido]-3-oxo-2-isoxazolidinyl}-5-oxo-2-tetrahydrofurancarboxylate [Compound (19):

In a mixture of 6 ml of ethyl acetate and 6 ml of a phosphate buffer solution of pH 7.0 was dissolved 125 mg of the Compound (9) obtained in Example 9. To the solution was added 125 mg of 10% palladium-carbon, and the mixture was stirred for one hour under ice-cooling in hydrogen streams. The catalyst was filtered off and washed with water. The filtrate and the washing were combined, and the aqueous layer was taken, to which was added 4 ml of tetrahydrofuran. To the mixture were added, under ice-cooling and stirring, 63 mg of sodium hydrogen carbonate and 102 mg of 2-(2-chloroacetamido-4-thiazolyl)-(Z)-2-methoxyiminoacetyl chloride hydrochloride. The reaction solution was stirred for 20 minutes, to which was added 57 mg of sodium N-methyl dithiocarbamate, followed by stirring at room temperature for 40 minutes. Tetrahydrofuran was evaporated off under reduced pressure, and the residue was washed with ethyl acetate, followed by purification by means of an HP-20 column. Fractions eluted with water were lyophilized to give 70 mg of the subject Compound (19) as white powder. The IR and NMR spectra of this product were in agreement with those of the (4R) type Compound (17) obtained in Example 17.

Elemental analysis for: $C_{14}H_{14}N_5NaO_8S \cdot 1.5H_2O$
Calcd. C,36.37; H,3.71; N,15.15
Found C,36.59; H,3.85; N,15.31

EXAMPLE 20

Production of 1-benzyl 2-oxoglutarate [Compound (20)].

In 20 ml of anhydrous N,N-dimethylformamide was dissolved 2.92 g of 2-oxoglutaric acid. To the solution were added 3.63 g of dicyclohexylamine and 2.61 ml of benzyl bromide. The mixture was stirred at room temperature for two hours. To the reaction solution was added ethyl acetate. The crystals which separated out were filtered off. The filtrate was washed with water and dried ($Na_2SO_4$). The solvent was evaporated off. The residue was subjected to a silica gel column chromatography, followed by elution with hexane-ethyl acetate-acetic acid (50:50:1) to give 3.20 g of the subject Compound (20) as colorless crystals. Recrystallization from ether-hexane gave colorless prisms, m.p. 51°–52° C.

$IR\nu_{max}^{Nujol}$ $cm^{-1}$:1740,1705,1270,1090,1040

NMR(90 MHz, $CDCl_3$)δ: 2.67(2H,t,J=6 Hz), 2.97(2H,m),5.26(2H,s),7.35(5H,s),8.9(1H,b)

Elemental analysis for :$C_{12}H_{12}O_5$
Calcd. C,61.01; H,5.12
Found C,61.02; H,5.12

EXAMPLE 21

Production of 1-(4-nitrobenzyl) 4-methyl-2-oxoglutarate [Compound(21)]:

In 6 ml of anhydrous N,N-dimethylformamide was dissolved 0.74 g of 4-methyl-2-oxoglutaric acid. To the solution were added 0.94 ml of dicyclohexylamine and 1.0 g of 4-nitrobenzyl bromide. The mixture was stirred at room temperature for 14 hours. To the reaction solution was added ethyl acetate. Crystals which separated out were filtered off. The filtrate was washed with water and dried ($Na_2SO_4$), then the solvent was evaporated off. The residue was subjected to a silica gel column chromatography, followed by elution with hexane-ethyl acetate (1:1→1:3) to give 0.66 g of the subject Compound (21) as pale yellow oil.

$IR\nu_{max}^{Neat}cm^{-1}$: 1780–1700, 1520, 1345, 1220,1170

NMR (90 MHz, $CDCl_3$)δ:1.32(3H,d,J=6 Hz), 2.2–3.3(3H,m),5.38(2H,s),6.0(1H,b),7.55(2H,d,J=9 Hz),8.22(2H,d,J=9 Hz)

EXAMPLE 22

Production of 4-nitrobenzyl 2-chloro-4-methyl-5-oxo-2-tetrahydrofurancarboxylate [Compound (22)]:

In 5 ml of 1,2-dichloroethane was dissolved 0.13 g of the Compound (21) obtained in Example 21. To the solution was added 0.13 ml of thionyl chloride. The mixture was heated for 90 minutes under reflux. The solvent was evaporated off, and the residue was subjected to a silica gel column chromatography, followed by elution with hexane-ethyl acetate (3:1) to give 0.11 g of the subject Compound (22) as colorless oil.

$IR\nu_{max}^{Neat}cm^{-1}$:1810,1755,1600, 1520, 1345, 1165,1070,1010

NMR (90 MHz, $CDCl_3$)δ: 1.35(1.5H,d,J=6 Hz),1.47(1.5H,d,J=6 Hz),2.3–3.5 (3H,m), 5.42(2H,s),7.59(2H,d,J=9 Hz),8.25(2H,d,J=9 Hz)

EXAMPLE 23

Production of 4-nitrobenzyl 2-[(4S)-4-benzyloxycarbonylamino-3-oxo-2-isoxazolidinyl]-4-methyl-5-oxo-2-tetrahydrofurancarboxylate [Compound (23)]:

In 4 ml of 1,2-dichloroethane were dissolved 118 mg of (4S)-4-benzyloxycarbonylamino-3-isoxazolidinone obtained by Reference Example 4 and 150 mg of the Compound (21) obtained in Example 21. To the solution was added 160 mg of DCC, and the mixture was stirred for 90 minutes at room temperature. Crystals which separated out were filtered off, which were washed with dichloromethane. The filtrate and the washing were combined and washed with an aqueous solution of sodium hydrogen carbonate then with water, followed by drying ($Na_2SO_4$). The solvent was evaporated off. The residue was subjected to a silica gel column chromatography, followed by elution with hexane-ethyl acetate (3:2) to give 152 mg of the subject Compound (23) as colorless oil.

$IR\nu_{max}^{Neat}cm^{-1}$:1795, 1760–1700, 1520, 1450, 1345,1260,1180,1080,1010

NMR(90 MHz, $CDCl_3$)δ:1.27(3H,d,J=6 Hz), 2.0(1H,m),2.7–3.5(2H,m),4.1(1H,m),4.7(2H,m), 5.10(2H,s),5.35(2H,s),7.33(5H,s),7.55(2H,d,J=9 Hz),8.22(2H,d,J=9 Hz)

Mass Spectrum m/e: 5 1 3($M^+$)

EXAMPLE 24

Production of Compound (23):

In 4 ml of dichloromethane was dissolved 55 mg of (4S)-4-benzyloxycarbonylamino-3-isoxazolidinone obtained in Reference Example 4. To the solution were added under ice-cooling and stirring, 0.7 ml of triethylamine and 1.5 ml of dichloromethane solution dissolving 80 mg of the Compound (22) obtained in Example 22. The reaction solution was stirred at room temperature for one hour, followed by washing with water and drying ($Na_2SO_4$). The solvent was evaporated off. The residue was subjected to a silica gel column chromatography, followed by elution with hexane-ethyl acetate (3:2) to give 78 mg of the subject Compound (23) as colorless oily product. The IR and NMR spectra of this product were in agreement with those of the Compound (23) obtained in Example 23.

EXAMPLE 25

Production of sodium 2-{(4S)-4-[2-(2amino-4-thiazolyl)-(Z)-2-(methoxyimino)acetamido]-3-oxo-2-isoxazolidinyl}-4-methyl-5-oxo-2-tetrahydrofurancarboxylate [Compound (25)]:

In a mixture of 5 ml of ethyl acetate and 7.5 ml of a phosphate buffer of pH 7.0 was dissolved 225 mg of the Compound (23) obtained in Example 23. To the solution was added 225 mg of 10% palladium-carbon. The mixture was stirred for 75 minutes under ice-cooling in hydrogen streams. The catalyst was filtered off and washed with water. The filtrate and the washing were combined, and the aqueous layer was taken. To the aqueous layer was added 5 ml of tetrahydrofuran. To the mixture were added, under ice-cooling and stirring, 110 mg of sodium hydrogen carbonate and 180 mg of 2-(2-chloroacetamido-4-thiazolyl)-(Z)-2-methoxyiminoacetyl chloride hydrochloride. The reaction solution was stirred for 30 minutes, to which was added 100 mg of sodium N-methyl dithiocarbamate. The mixture was stirred at room temperature for 45 minutes. Tetrahydrofuran was evaporated off under reduced pressure, and the residue was washed with ethyl acetate, followed by purification by means of an HP-20 column. Fractions eluted with water were lyophilized to give 106 mg of the subject Compound (25) as white powder.

IRν$_{max}^{KBr}$ cm$^{-1}$:1775,1720,1660,1530, 1380, 1200,1030

NMR(90 MHz, D$_2$O)δ: 1.4(3H,m),2.3(1H,m), 2.9–3.7(3H,m),4.12 (3H,s),4.5(1H,m),4.9–5.5(2H,m),7.17(1H,s)

Elemental analysis for:C$_{15}$H$_{16}$N$_5$NaO$_8$S·H$_2$O
Calcd. C,38.55; H,3.88; N,14.98
Found C,38.56; H,3.89; N,14.66

EXAMPLE 26

Production of methyl 2-bromo-2,5-dihydro-5-oxo-2-furancarboxylate [Compound (26)]:

In 4 ml of dichloromethane was dissolved 184 mg of methyl 5-acetoxy-2-furancarboxylate. To the solution was gradually added one ml of dichloromethane solution dissolving 0.045 ml of bromine. The reaction solution was stirred at room temperature for 30 minutes. Then, the solvent and acetyl bromide formed as the by-product were evaporated off under reduced pressure to give 220 mg of the subject Compound (26) as pale yellow oil.

IRν$_{max}^{Neat}$ cm$^{-1}$: 1805,1760,1435,1265,1210,1105,880
NMR (90 MHz, CDCl$_3$)δ: 3.88(3H,s),6.27(1H,d,J=6 Hz),7.8(1H,d,J=6 Hz)

EXAMPLE 27

Production of methyl 2-chloro-2,5-dihydro-5-oxo-2-furancarboxylate [Compound (27)]:

In 4 ml of dichloromethane was dissolved 184 mg of methyl 5-acetoxy-2-furancarboxylate. To the solution was added 1.5 ml of a chlorine-containing carbon tetrachloride solution (2 mol.). The mixture was stirred at room temperature for 30 minutes. Then, the solvent and acetyl chloride formed as the by-product were evaporated off under reduced pressure to give 176 mg of the subject Compound (27) as colorless oil.

IRν$_{max}^{Neat}$ cm$^{-1}$:1810,1760,1440,1270,1210,1100,880
NMR (90 MHz, CDCl$_3$)δ:3.90(3H,s),6.13(1H,d,J=6 Hz),7.60(1H,d,J=6 Hz)

EXAMPLE 28

Production of benzyl 2-chloro-2,5-dihydro-5-oxo-2-furancarboxylate [Compound (28)]:

In a mixture of 50 ml of acetic acid and 10 ml of acetic anhydride was dissolved 10.1 g of 2-furancarboxylic acid. Into the solution was introduced 4.55 g of chlorine gas under stirring while keeping the inner temperature at 7° C. The mixture was allowed to stand at room temperature for 40 hours, then the solvent was evaporated off, followed by elimination of fractions distilling out at 170° C. (bath temperature) under 0.5 mmHg. The residue was subjected to a silica-gel column chromatography, followed by elution with hexane-ethyl acetate (6:1) to give 2.6 g of benzyl 5-acetoxy-2-furancarboxylate as colorless oil.

IRν$_{max}^{Neat}$ cm$^{-1}$:1770,1700,1520,1480,1300,1205,1140,1020
NMR(90 MHz, CDCl$_3$)δ: 2.28(3H,s),5.30(2H,s),6.07(1H,d,J=3 Hz),7.19(1H,d,J=3 Hz), 7.37(5H,s)

Mass Spectrum m/e: 2 6 0(M+) In 4 ml of dichlormethane was dissolved 260 mg of this product. To the solution was added 1.4 ml of chlorine-containing carbon tetrachloride (2 mol), and the mixture was stirred at room temperature for 30 minutes. The solvent and acetyl chloride formed as the by-product were evaporated off under reduced pressure to give 250 mg of the subject Compound (28) as colorless oil.

IRν$_{max}^{Neat}$ cm$^{-1}$:1810,1760,1260,1210,1100,1060,880
NMR(90 MHz, CDCl$_3$)δ: 5.30(2H,s),6.27(1H,d,J=6 Hz),7.40(5H,s),7.58(1H,d,J=6 Hz)

EXAMPLE 29

Production of methyl 2-[(4R)-4-benzyloxycarbonylamino-3-oxo-2-isoxazolidinyl]-5-oxo-2,5-dihydro-2-furancarboxylate [Compound (29)]:

In 25 ml of dichloromethane was dissolved 240 mg of (4R)-4-benzyloxycarbonylamino-3-isoxazolidininone. To the solution were added, under ice-cooling and stirring, 0.25 ml of triethylamine and 2 ml of dichloromethane solution dissolving 220 mg of the Compound (26) obtained in Example 26. The reaction solution was stirred at room temperature for 30 minutes, then washed with water, and dried (Na$_2$SO$_4$). The solvent was evaporated off, and the residue was subjected to a silica gel column chromatography, followed by elution with hexane-ethyl acetate (2:1→1:1) to give 150 mg of the subject Compound (29) as pale yellow oil:

IRν$_{max}^{Neat}$cm$^{-1}$:3350,1810,1770–1710, 1530,1260,1080,1040,960, 900
NMR(90MHz, CDCl$_3$)δ: 3.85(3H,s),4.2(1H,m),4.8(2H,m),5.11(2H,s),5.4(1H,b),6.32(1H,d,J=6 Hz),7.35(5H,s),7.60(1H,d,J=6 Hz)

Mass spectrum m/e: 3 7 6 (M+)

EXAMPLE 30

Production of methyl 2-[(4R)-4-phenylacetamido-3-oxo-2-isoxazolidinyl]-5-oxo-2,5-dihydro-2-furancarboxylate [Compound (30)]:

(a) In 8 ml of dichloromethane was suspended 110 mg of (4R)-4-phenylacetamido-3-isoxazolidinone. To the suspension were added, under ice-cooling and stirring, 0.14 ml of triethylamine and 2 ml of dichloromethane solution dissolving 106 mg of the Compound (27) obtained in Example (27). The reaction solution was stirred at room temperature for 40 minutes, washed with water and dried (Na$_2$SO$_4$). The solvent was then evaporated off. The residue was subjected to a silica gel column chromatography, followed by elution with hexane-ethyl acetate (2:3) to give 78 mg of the subject Compound (30) as colorless oil.

IRν$_{max}^{Neat}$cm$^{-1}$:3300,1800,1750,1660,1530,1260,1080, 1040,900
NMR(90 MHz, CDCl$_3$)δ: 3.59(2H,s),3.83(3H,s),4.1(1H,m),4.8(2H,m),6.5(1H,b),6.30(1H,d), 7.30(5H,s),7.53(0.5H,d,J=6 Hz),7.60(0.5H,d,J=6 Hz), Mass spectrum m/e: 3 6 0 (M+)

(b) In 3 ml of anhydrous N,N-dimethylformamide was dissolved 220 mg of (4R)-4-phenylacetamido-3-isoxazolidinone. To the solution were added, under ice-cooling and stirring, 60 mg of sodium hydride (50% mineral oil) and 0.5 ml of anhydrous N,N-dimethylformamide solution dissolving 220 mg of the Compound (26) obtained in Example 26. The reaction solution was stirred for 69 minutes under ice-cooling, which was then poured into a mixture of ethyl acetate and water. The ethyl acetate layer was taken, washed with water and dried (Na$_2$SO$_4$). The solvent was evaporated off, and the residue was subjected to a silica gel column chromatography, followed by elution with hexaneethyl acetate (2:1→2:3) to give 32 mg of the subject Compound (30) as colorless oil.

EXAMPLE 31

Production of methyl 2-[(4R)-4-phenylacetamido-3-oxo-2-isoxazolidinyl]-5-oxo-2-tetrahydrofurancarboxylate [Compound (31)]:

In 3 ml of tetrahydrofuran was dissolved 30 mg of the Compound (30) obtained in Example 30. To the solution was added 30 mg of 10% palladium-carbon, and the mixture was stirred at room temperature for 30 minutes in hydrogen streams. The catalyst was filtered off and washed with tetrahydrofuran. The filtrate and the washing were combined, then the solvent was evaporated off. The residue was subjected to a silica gel column chromatography, followed by elution with hexane-ethyl acetate (2:3) to give 24 mg of the subject Compound (31) as colorless oil.

$IR\nu_{max}^{Neat}cm^{-1}$:
3300,1800,1750,1660,1530,1270,1190,1050
NMR(90 MHz, CDCl$_3$)δ: 2.3–3.3(4H,m), 3.57(2H,s),3.82(1.5H,s),3.84(1.5H,s),4.1(1H,m),4.8-(2H,m),6.2(0.5H,b),6.4(0.5H,b), 7.30(5H,s)
Mass spectrum m/e: 3 6 2(M$^+$)

EXAMPLE 32

Production of benzyl 2-[(4R)-4-phenylacetamido-3-oxo-2-isoxazolidinyl]-5-oxo-2,5-dihydro-2-furancarboxylate [Compound (32)]:

In 3 ml of anhydrous N,N-dimethylformamide was dissolved 220 mg of (4R)-4-phenylacetamido-3-isoxazolidinone. To the solution was added, under ice-cooling and stirring, 60 mg of sodium hydride (50% mineral oil), which was stirred for 10 minutes. Then the reaction solution was cooled to −10° C., to which was added under stirring 0.7 ml of anhydrous N,N-dimethylformamide solution dissolving 250 mg of the Compound (28) obtained in Example 28. The reaction solution was stirred at the same temperature for 45 minutes, followed by pouring into a mixture of ethyl acetate and water. The ethyl acetate layer was taken, washed with water and dried (Na$_2$SO$_4$). The solvent was evaporated off, and the residue was subjected to a silica gel column chromatography, followed by elution with hexane-ethyl acetate (2:1) to give 87 mg of the subject Compound (32) as colorless foamy substance.

$IR\nu_{max}^{Neat}cm^{-1}$:3300,1800,1760,1660,1530,1260,1080, 1035,900
NMR(90 MHz, CDCl$_3$)δ: 3.59(2H,s),4.0(1H,m),5.8(2H,m),5.25(1H,s),5.27(1H,s),6.1(1H,b),6.27(1H,d,J=6 Hz),7.3(10H,s),7.50(0.5H,d,J=6 Hz),7.57(0.5H,d,J=6 Hz)
Mass spectrum m/e: 4 3 6(M$^+$)

EXAMPLE 33

Production of sodium 2-[(4R)-4phenylacetamido-3-oxo-2-isoxazolidinyl]-5-oxo-2-tetrahydrofurancarboxylate [Compound (33)]:

In a mixture of 5 ml of ethyl acetate and 5 ml of a phosphate buffer solution of pH 7.0 was dissolved 68 mg of the Compound (32) obtained in Example 32. To the solution was added 70 mg of 10% palladium-carbon. The mixture was stirred for two hours under ice-cooling in hydrogen streams. The catalyst was filtered off and washed with water. The filtrate and the washing were combined. The concentrate was purified a column of HP-20, and the fraction eluted with 5% ethanol was lyophilized to give 41 mg of the subject Compound (33) as white powder.

$IR\nu_{max}^{KBr}cm^{-1}$:3400,1775,1720,1650,1530,1370,1185,-1110,1020, 965, 900
NMR(90 MHz, D$_2$O)δ: 2.5–3.5(4H,m),3.83(2H,s),4-.3–5.3(3H,m),7.53(5H,s)

EXAMPLE 34

Production of 1-(4-nitrobenzyl) 2-oxo-3-phenylthioglutarate [Compound (34)]:

In 40 ml of dichloromethane was suspended 2.5 g of 3-bromo-2-oxoglulatic acid. To the suspension was added 1.0 ml of thiophenol under ice-cooling and stirring, to which was added 4.15 ml of triethylamine. The reaction solution was stirred at room temperature for 45 minutes. Then, the solvent was evaporated off. The residue was shaken with a mixture of ethyl acetate and 1 N-HCl. The ethyl acetate layer was taken, washed with water and dried (Na$_2$SO$_4$), followed by removal of the solvent by evaporation to give 2.28 g of 2-oxo-3-phenylthioglutaric acid as pale yellow oil.

$IR\nu_{max}^{Neat}cm^{-1}$: 1720, 1470, 1440, 1400,1280,1200
NMR(90 MHz, CDCl$_3$)δ:2.87(2H,d,J=8 Hz), 4.73(1H,t,J=8 Hz),7.40(5H,s),9.4(2H,b)

To 18 ml of N,N-dimethylformamide solution dissolving 2.28 g of this product were added, under ice-cooling and stirring, 1.43 ml of dicyclohexylamine and 1.5 g 4-nitrobenzyl bromide. The reaction solution was stirred at room temperature for 15 hours, followed by dilution with ethyl acetate. The crystals which separated out were filtered off. The filtrate was washed with water and dried (Na$_2$SO$_4$). The solvent was then evaporated off. The residue was subjected to a silica gel column chromatography, followed by elution with hexane-ethyl acetate (1:2→1:3) to give 2.25 g of the subject Compound (34) as colorless crystals. Recrystallization from ether-hexane gave colorless prisms, m.p. 119°–120° C.

$IR\nu_{max}^{Nujol}$ cm$^{-1}$: 1745, 1730, 1700, 1520, 1440,1350,1280
NMR(90 MHz, CDCl$_3$)δ:2.895(2H,d,J=8 Hz), 4.7(1H,m),5.43(2H,s),6.7(1H,b),7.35(5H,s), 7.60(2H,d,J=9 Hz)
Elemental analysis for :C$_{18}$H$_{15}$NO$_7$S
Calcd. C,55.52; H,3.88; N,3.60
Found C,55.49; H,3.90; N,3.50

EXAMPLE 35

Production of 4-nitrobenzyl 2-chloro-3-phenylthio-5-oxo-2-tetrahydrofurancarboxylate [Compound (35)]:

In 4 ml of 1,2-dichloroethane was dissolved 145 mg of the Compound (34) obtained in Example 34. To the solution was added 0.30 ml of thionyl chloride. The mixture was heated for 4 hours under reflux. The solvent was evaporated off, and the residue was subjected to a column chromatography using Florisil. Elution was conducted using hexane-ethyl acetate (3:1) to yield 116 mg of the subject Compound (35) as colorless oil.

$IR\nu_{max}^{Neat}$ cm$^{-1}$:1825,1770,1525,1350,1290,1090
NMR(90 MHz, CDCl$_3$)δ: 2.71(1H,dd,J=3,18 Hz), 3,37(1H,dd,J=8,18 Hz),4.27(1H,dd,J=3,8 Hz), 5.37(2H,ABq,J=13,22
Hz),7.35(5H,m),7.57(2H,d,J=9 Hz),8.23(2H,d,J=9 Hz)
Mass Spectrum m/e: 4 0 7,4 0 9 (M$^+$)

EXAMPLE 36

Production of 4-nitrobenzyl 2-[(4S)-4-benzyloxycarbonylamino-3-oxo-2-isoxazolidinyl]-5-oxo-3-phenylthio-2-tetrahydrofurancarboxylate [Compound (36)]:

In 7.5 ml of dichloromethane were dissolved 177 mg of (4S)-4-benzyloxycarbonylamino-3-isoxazolidinone and 380 mg of the Compound (34) obtained in Example 34. To the solution was added 210 mg of DCC, and the mixture was stirred at room temperature for one hour. The crystals which separated out were filtered off and washed with dichloromethane. The filtrate and washing were combined and washed with an aqueous solution of sodium hydrogen carbonate, then with water, followed by drying ($Na_2SO_4$). The solvent was then evaporated off, and the residue was subjected to a silica gel column chromatography, followed by elution with hexane-ethyl acetate (5:3) to give 185 mg of the subject Compound (36) as colorless oil.

IR$\nu_{max}^{Neat}$ cm$^{-1}$: 3350, 1810,1760,1730,1525,1350,1250,1055
NMR(90 MHz, CDCl$_3$)δ: 2.5–3.4(2H,m), 4.1(1H,m),4.4–5.0(3H,m),5.10(2H,s),5.3(1H,b), 5.35(2H,s),7.33(5H,s),7.5(7H,m),8.2(2H,m)

EXAMPLE 37

Production of Compound (36):

In 3 ml of dichloromethane was dissolved 48 mg of (4S)-4-benzyloxycarbonylamino-3-isoxazolidinone. To the solution were added, under ice-cooling and stirring, 0.055 ml of triethylamine and 2 ml of dichloromethane solution dissolving 110 mg of the Compound (35) obtained in Example 35. The reaction solution was stirred at room temperature for 30 minutes, washed with water and dried ($Na_2SO_4$). The solvent was then evaporated off. The residue was subjected to a silica gel column chromatography, followed by elution with hexane-ethyl acetate (5:3) to give 23 mg of the subject Compound (36) as colorless oil. The IR and NMR spectra of this product were in agreement with those of the Compound (36) of Example 36.

EXAMPLE 38

Production of sodium 2-[(4S)-4-benzyloxycarbonylamino-3-oxo-2-isoxazolidinyl]-5-oxo-3-phenyltio-2-tetrahydrofurancarboxylate [Compound (38)]:

In a mixture of 2 ml of ethyl acetate and 3 ml of a phosphate buffer solution of pH 7.0 was dissolved 70 mg of the Compound (36) obtained in Example 36. To the solution was added 140 mg of 10% palladium-carbon, and the mixture was stirred at room temperature for 2.5 hours in hydrogen streams. The catalyst was filtered off and washed with water. The filtrate and washing were combined. The aqueous layer was taken and concentrated. The concentrate was purified with a column of HP-20. The fraction eluted with 30% ethanol was lyophilized to give 20 mg of the subject Compound (38) as white powder.

IR$\nu_{max}^{KBr}$ cm$^{-1}$:1780,1710,1650,1500,1380,1240
NMR(90 MHz, D$_2$O)δ: 2.7–3.5(2H,m), 3.7–5.3(4H,m),5.20(2H,s),7.5(10H,b)

EXAMPLE 39

Production of 1-(4-nitrobenzyl) 3-ethylthio-2-oxoglutarate [Compound (39)]:

In 20 ml of dichloromethane was suspended 1.00 g of 3-bromo-2-oxoglutaric acid. To the suspension was added 0.33 ml of ethane thiol under ice-cooling and stirring, to which was added 1.83 ml of triethylamine. The reaction solution was stirred at room temperature for 3 hours, then the solvent was evaporated off. The residue was shaken with a mixture of ethyl acetate and 1N-HCl. The ethyl acetate layer was taken, washed with water and dried ($Na_2SO_4$). The solvent was evaporated off to give 0.82 g of 3-ethylthio-2-oxoglutaric acid as pale yellow oil.

IR$\nu_{max}^{Neat}$ cm$^{-1}$: 3000(b), 1720, 1400, 1250
NMR(90 MHz, CDCl$_3$)δ:1.23(3H,t,J=8 Hz), 2.55(2H,q,J=8 Hz),3.0(2H,b),4.4(1H,b),8.9(2H,b)

In 8 ml of N,N-dimethylformamide was dissolved 0.82 g of this product. To the solution were added under ice-cooling and stirring 0.65 ml of dicyclohexylamine and 0.70 g of 4-nitrobenzyl bromide. The reaction solution was stirred at room temperature for 3 hours, followed by dilution with ethyl acetate. The crystals which separated out were filtered off. The residue was subjected to a silica gel column chromatography, followed by elution with hexane-ethyl acetate (3:2) and ethyl acetate to give 0.61 g of the subject Compound (39) as colorless crystals. Recrystallization from isopropyl ester gave colorless prisms, m.p. 100°–101° C.

IR$\nu_{max}^{Nujol}$ cm$^{-1}$:1745,1720,1700,1530,1350,1255
NMR(90 MHz, CDCl$_3$)δ:1.18(3H,t,J=8 Hz), 2.48(2H,q,J=8 Hz),2.95(2H,m),4.3(1H,b), 5.41(2H,s),7.0(1H,b),7.57(2H,d,J=9 Hz), 8.25)2H,d,J=9 Hz)

Elemental analysis for :$C_{14}H_{15}NO_7S$
Calcd. C,49.26; H,4.43; N,4.10
Found C,49.32; H,4.33; N,3.99

EXAMPLE 40

Production of 4-nitrobenzyl 2-chloro-3-ethylthio-5-oxo-2-tetrahydrofurancarboxylate [Compound (40)]:

In 4 ml of 1,2-dichloroethane was dissolved 170 mg of the Compound (39) obtained in Example 39. To the solution was added 0.30 ml of thionyl chloride. The mixture was heated for 3.5 hours under reflux. The solvent was evaporated off, and the residue was subjected to a column chromatography using Florisil (Floridin Inc. U.S.A.), followed by elution with hexane and hexane-ethyl acetate (3:1) to give 79 mg of the subject Compound (40) as colorless oil.

IR$\nu_{max}^{Neat}$cm$^{-1}$:1820,1770,1610,1530,1355,1290,1145,10-90
NMR(90 MHz, CDCl$_3$)δ:1.15(3H,t,J=7 Hz), 2.7(3H,m),3.37(1H,dd,J=9,18 Hz),3.95(1H,dd,J=4,9 Hz), 5.43(2H,s),7.60(2H,d,J=9 Hz), 8.25(2H,d,J=9 Hz)
Mass Spectrum m/e: 3 5 9 , 3 6 1 (M$^+$)

EXAMPLE 41

Production of 1-t-butyl 2-oxoglutarate [Compound (41)]:

In 100 ml of dichloromethane was dissolved 5.0 g of 5-oxo-2-tetrahydrofurancarboxylic acid. To the solution was added 0.3 ml of concentrated sulfuric acid at −60° C., to which was added an excess volume of isobutene (about 50 ml). The reaction mixture was allowed to stand at room temperature overnight in a sealed vessel, which was then poured into a cooled aqueous solution of sodium hydrogen carbonate. The dichloromethane layer was taken, washed with water and dried (Na$_2$SO$_4$), followed by concentration to give t-butyl 5-oxo-2-tetrahydrofurancarboxylate as colorless oil.

IR$\nu_{max}^{Neat}$ cm$^{-1}$: 1760
NMR(60 MHz, CDCl$_3$)δ: 1.50(9H,s),2.4(4H,m),4.8(1H,m)

This produce was dissolved in 50 ml of absolute alcohol. To the solution was added, under ice-cooling and stirring, 100 mg of sodium methylate. The reaction solution was stirred for 3 hours under ice-cooling, followed by concentration. The concentrate was poured into a mixture of ethyl acetate and an aqueous solution of ammonium chloride. The ethyl acetate was taken and dried (Na$_2$SO$_4$). Then, the solvent was evaporated off to leave 8.2 g of 1-t-butyl 5-methyl-2-hydroxyglutarate colorless crystals. Recrystallization from hexane gave colorless prisms, m.p. 36°–37° C.

IR$\nu_{max}^{Nujol}$cm$^{-1}$:3450,1735,1260,1230,1160,1110
NMR(90 MHz, CDCl$_3$)δ: 1.47(9H,s), 1.7–2.6(4H,m),2.87(1H,d,J=5 Hz),3.63(3H,s),4.1 (1H,m)

Elemental analysis for :C$_{10}$H$_{18}$O$_5$
Calcd. C,55.03; H,8.31
Found C,54.60; H,8.35

In 12 ml of a dichloromethane was dissolved 0.39 ml of oxalyl chloride. To the solution was added at −70° C. while stirring under nitrogen atmosphere 4 ml of a dichloromethane solution dissolving 0.60 ml of dimethylsulfoxide. To the mixture was added 3.5 ml of a dichloromethane solution dissolving 0.95 g of the 1-t-butyl 5-methyl-2-hydroxyglutarate obtained above. The whole mixture was stirred at −70° C. for 15 minutes, followed by addition of 3.0 ml of triethylamine. The temperature of the reaction solution was raised up to −40° C., then the reaction solution was poured into ice-water, followed by extraction with dichloromethane. The extract solution was washed with water, dilute acid and water, successively, then dried (Na$_2$SO$_4$). The solvent was evaporated off, and the residue was subjected to a silica gel column chromatography, followed by elution with hexaneethyl acetate (5:1) to give 0.60 g of 1-t-butyl 5-methyl-2-oxoglutarate as pale yellow oil.

IR$\nu_{max}^{Neat}$ cm$^{-1}$:1730,1370,1295,1260,1200,1160,1080
NMR(90 MHz, CDCl$_3$)δ: 1.57(9H,s),2.63 (2H,t,J=6Hz),3.10(2H,s,J=6Hz),3.69(3H,s)

In a mixture of 1 ml of tetrahydrofuran and 1 ml of water was dissolved 108 mg of this product. To the solution was added under ice-cooling while stirring 0.4 ml of 1N-sodium hydroxide. The reaction solution was stirred for 45 minutes under ice-cooling, which was then poured into a mixture of water and ethyl acetate. The aqueous layer was taken, to which was added 1N-HCl to adjust the pH to 4, followed by extraction with ethyl acetate. The extract solution was washed with an aqueous saline solution and dried (Na$_2$SO$_4$). The solvent was evaporated off, and the residue was subjected to a silica gel column chromatography, followed by elution with hexane-ethyl acetate (3:2→1:2) to give 26 mg of the subject Compound (41) as colorless crystals m.p. 76°–77° C.

IR$\nu_{max}^{KBr}$ cm$^{-1}$:1740, 1700, 1280, 1250, 1160, 1080
NMR(90 MHz,CDCl$_3$)δ: 1.55(9H,m), 2.58–3.05(4H,m), 8.10(1H,bs)

EXAMPLE 42

Production of 1-diphenylmethyl 2-oxoglutarate [Compound (42)]:

Employing 2.93 g of 2-oxoglutaric acid, 4.75 g of diphenylmethyl bromide and 3.63 g of dicyclohexylamine, a reaction analogous to that in Example 1 (a) was conducted to give 3.2 g of the subject Compound (42) conducted as crystals, m.p. 107°–109° C.

IR$\nu_{max}^{KBr}$ cm$^{-1}$: 1730, 1710
NMR(60 MHz, CDCl$_3$)δ: 2.58–3.17(4H,m), 6.99(1H,s),7.31–7.54(10H,m)

Elemental analysis for :C$_{18}$H$_{16}$O$_5$
Calcd. C,69.22; H,5.16
Found C,69.30; H,5.18

EXAMPLE 43

Using the following ingredients, tablets are produced by the conventional means:

| | |
|---|---|
| Compound (4) as obtained in Example 4 | 300 mg |
| Corn starch | 50 mg |
| Lactose | 28 mg |
| Hydroxypropylcellulose L | 20 mg |
| Magnesium stearate | 2 mg |
| | 400 mg per tablet |

4 to 8 tablets are to be administered to an adult daily after each meal (three times per day).

EXAMPLE 44

Using the following ingredients, tablets are produced by the conventional means:

| | |
|---|---|
| Compound (25) as obtained in Example 25 | 300 mg |
| Corn starch | 50 mg |
| Lactose | 28 mg |
| Hydroxypropylcellulose L | 20 mg |
| Magnesium stearate | 2 mg |
| | 400 mg per tablet |

4 to 8 tablets are to be administered to an adult daily after each meal (three times per day).

EXAMPLE 45

Production of 4-nitrobenzyl 2-[(4S)-4-(4-nitrobenzyloxycarbonylamino)-3-oxo-2-isoxazolidinyl]-5-oxo-3-ethylthio-2-tetrahydrofurancarboxylate [Compound (45)]:

(a) In 6 ml of dichloromethane were suspended 140 mg of (4S)-4-(4-nitrobenzyloxycarbonylamino)-3-isoxazolidinone obtained in Reference Example 5 and 200 mg of the Compound (39) obtained in Example 39. To the suspension was added 120 mg of DCC, and the mixture was stirred at room temperature for 14 hours. The crystals which separated out were filtered off and washed with dichloromethane. The filtrate and the washing were combined, which was washed with an aqueous solution of sodium hydrogen carbonate and water, followed by drying (Na$_2$SO$_4$). The solvent was evaporated off, and the residue was subjected to a silica gel column chromatography, followed by elution with hexane ethyl acetate (1:1) to give 70 mg of the subject Compound (45) as pale yellow oil.

IR$\nu_{max}^{Neat}$ cm$^{-1}$:3330,1805,1750,1625,1520,1350.
NMR(90 MHz, CDCl$_3$)δ:1.15(3H,t,J=7 Hz), 2.45–3.40(3H,m),4.0–5.0(5H,m),5.20(2H,s), 5.37(2H,s),5.9(1H,b),7.55(4H,m),8.20(4H,d,J=7 Hz).

(b) In 10 ml of dichloromethane were suspended 140 mg of (4S)-4-(4-nitrobenzyloxycarbonylamino)-3-isoxazolidinone obtained in Reference Example 5 and 200 mg of the Compound (39) obtained in Example 39. To the suspension was added 160 mg of 1-ethoxycarbonyl-2-ethoxy-1,2-dihydroquinoline. The mixture was stirred at room temperature for 6 hours. The solvent was evaporated off, and the residue was subjected to a silica gel column chromatography, followed by elution with hexane-ethyl acetate (1:1) to give 165 mg of the subject Compound (45) as pale yellow oil. The IR and NMR spectra of this product were in agreement with those of the compound obtained in (a) above.

EXAMPLE 46

Production of sodium 2-{(4S)-4-[2-(2-amino-4-thiazolyl)-(Z)-2-(methoxyimino)acetamido]-3-oxo-2-isoxazolidinyl}-3-ethylthio-5-oxo-2-tetrahydrofuran carboxylate [Compound (46)]:

In a mixture of 5 ml of ethyl acetate and 5 ml of a phosphate buffer solution of pH 7.0 was dissolved 60 mg of the Compound (45) obtained in Example 45. To the solution was added 150 mg of 10% palladium-carbon, and the mixture was stirred for 4 hours in hydrogen streams under ice-cooling. The catalyst was filtered off and washed with water. The filtrate and the washing were combined, and the aqueous layer was taken, to which was added 3 ml of tetrahydrofuran. To the mixture were added, under ice-cooling and stirring, 30 mg of sodium hydrogen carbonate and 40 mg of 2-(2-chloroacetamido-4-thiazolyl)-(Z)-2-methoxyiminoacetyl chloride hydrochloride. The reaction solution was stirred for 30 minutes, to which was added 30 mg of sodium N-methyldithiocarbamate. The mixture was stirred at room temperature for one hour. Tetrahydrofuran was evaporated off under reduced pressure, and the concentrate was washed with ethyl acetate, followed by purification by means of a column of HP-20. The fraction eluted with 5% ethanol was lyophilized to give 8 mg of the subject Compound (46) as pale yellow powder.

IR$\nu_{max}^{KBr}$ cm$^{-1}$:1780,1720,1660,1530,1380,1030.
NMR(90 MHz, D$_2$O)$\delta$:1.40(3H,t,J=7Hz), 2.7–3.9(4H,m),4.17(3H,s),4.4–5.5(4H,m), 7.23(1H,s).

EXAMPLE 47

Production of 1-diphenylmethyl 2-oxo-3-phenylthioglutarate [Compound (47)]: In 30 ml of N,N-dimethylformamide was disssoved 6.7 g of crude 2-oxo-3-phenylthioglutaric acid obtained by the method of Example 34. To the solution were added at room temperature under stirring 4.0 ml of dicyclohexylamine and 5.0 g of diphenylmethylbromide. The reaction solution was stirred for 15 hours at room temperature, which was diluted with ethyl acetate. The crystals which separated out were filtered off, and the filtrate was washed with water and dried (Na$_2$SO$_4$), from which the solvent was evaporated off. The residue was subjected to a silica gel column chromatography, followed by elution with hexane-ethyl acetate (3:1→1:1) to give 3.2 g of the subject Compound (47) as pale yellow crystals. Recrystallization from hexaneethyl acetate gave colorless needles, m.p. 98°–100° C.

IR$\nu_{max}^{Nujol}$ cm$^{-1}$:1740,1205,1180.
NMR(60 MHz, CDCl$_3$)$\delta$:2.85(2H,d,J=8 Hz), 4.70(1H,t,J=8 Hz),7.05(1H,s),7.3(15H,m).

EXAMPLE 48

Production of diphenylmethyl 2-chloro-3-phenylthio-5-oxo-2-tetrahydrofuran carboxylate [Compound (48)]:

In 10 ml of 1,2-dichloroethane was dissolved 0.50 g of the Compound (4.7) obtained in Example 47. To the solution was added 0.4 ml of thionyl chloride. The mixture was heated for two hours under reflux. The solvent was evaporated off, and the residue was subjected to a column chromatography using Florisil, followed by elution with hexane-ethyl acetate (5:1) to give 0.30 g of the subject Compound (48) as colorless oil.

IR$\nu_{max}^{Neat}$ cm$^{-1}$:1820,1760,1380,1080.
NMR(90 MHz, CDCl$_3$)$\delta$:2.70(1H,dd,J=3.18 Hz), 3.29(1H,dd,J=8,18 Hz),4.20(1H,dd,J=3,8 Hz). 7.10(1H,s),7.4(15H,m).

EXAMPLE 49

Production of diphenylmethyl 2-chloro-5-oxo-2,5-dihydro-2-furancarboxylate [Compound (49)]:

In 10 ml of dichloromethane was dissolved 0.30 g of the Compound (48) obtained in Example 48. To the solution was added 150 mg of 3-chloroperbenzoic acid. The mixture was stirred at room temperature for 30 minutes. The reaction solution was washed with an aqueous solution of sodium hydrogen carbonate and water, successively. The resultant was dried (Na$_2$SO$_4$), and the solvent was evaporated off. The residue was dissoved in 6 ml of toluene, and the solution was heated at 60° C. for 30 minutes, then the solvent was evaporated off. The residue was subjected to a silica gel column chromatography, followed by elution with hexane-ethyl acetate (5:1) to give 0.15 g of the subject Compound (49) as colorless crystals. Recrystallization from ethyl acetatehexane to give colorless needless, m.p. 99°–101° C.

IR$\nu_{max}^{Nujol}$ cm$^{-1}$:1810,1760,1740,1260.
NMR(90 MHz, CDCl$_3$)$\delta$:6.27(1H,d,J=6 Hz), 6.90(1H,s),7.33(10H,s),7.58(1H,d,J=6 Hz).

EXAMPLE 50

Production of diphenylmethyl 2-[(4S)-4-phenylacetamido-3-oxo-2-isoxazolidinyl]-5-oxo-3-phenylthio-2-tetrahydrofurancarboxylate [Compound (50)]:

(a) In 10 ml of dichloromethane were suspended 110 mg of (4S)-4-phenylacetamido-3-isoxazolidinone and 252 mg of the Compound (47) obtained in Example 47. To the suspension was added 145 mg of DCC. The mixture was stirred at room temperature for two hours. The crystals which separated out were filtered off and washed with dichloromethane. The filtrate and the washing were combined, which was washed with an aqueous solution of sodium hydrogen carbonate and water, successively. The resultant was dried (Na$_2$SO$_4$), then the solvent was evaporated off. The residue was subjected to a silica gel column chromatography, followed by elution with hexane-ethyl acetate (3:1→3:2) to give 60 mg of the subject Compound (50) as colorless oil.

IR$\nu_{max}^{Neat}$cm$^{-1}$:3330,1810,1750,1670.
NMR(90 MHz, CDCl$_3$)$\delta$:2.4–3.3(2H,m),3.5(1H,s), 3.53(1H,s),3.7–5.0(4H,m),6.2(1H,m),6.9(0.5H,s), 7.0(0.5H,s),7.3(20H,m).

(b) In 10 ml of dichloromethane were suspended 110 mg of (4S)-4-phenylacetamido-3-isoxazolidinone and 252 mg of the Compound (47) obtained in Example 47. To the suspension was added 148 mg of 1-ethoxycarbonyl-2-ethoxy-1,2-dihydroquinoline. The mixture was stirred at room temperature for 14 hours. The solvent was evaporated off, and the residue was subjected to a silica gel column chromatography, followed by elution with hexane-ethyl acetate (3:1→3:2) to give 45 mg of the subject Compound (50) as pale yellow oil. The IR and NMR spectra of this product were in agreement with those of the compound in (a) above.

EXAMPLE 51

Production of diphenylmethyl 2-[(4S)-4-phenylacetamido-3-oxo-2-isoxazolidinyl]-5-oxo-2,5-dihydro-2-furancarboxylate [Compound (51)]:

(a) In 2.5 ml of dichloromethane suspension of 35 mg of (4S)-4-phenylacetamido-3-isoxazolidinone and 50 mg of diphenylmethyl 2-chloro-5-oxo-2,5-dihydro-2-furancarboxylate obtained in Example 49 was added under ice-cooling and stirring, 0.025 ml of triethylamine. The reaction solution was stirred at room temperature for 30 minutes, which was diluted with ethyl acetate, followed by washed with water and drying (Na$_2$SO$_4$). The solvent was evaporated off, and the residue was subjected to a silica gel column chromatography, followed by elution with hexane-ethyl acetate (1:1) to give 56 mg of the subject Compound (51) as colorless crystals. Recryslallization from dichloromethaneethylether afforded colorless prisms, m.p. 168°–169° C. (decomp.).

IR$\nu_{max}^{Nujol}$ cm$^{-1}$:3300,1800,1750,1670,1250.

NMR(90 MHz, CDCl$_3$)δ:3.57(2H,s),3.9(1H,m), 4.7(2H,m),6.0(1H,m),6.27(1H,d,J=6Hz),6.90(1H,-bs), 7.3(15H,s),7.57(1H,d,J=6 Hz).

(b) In 3 ml of dichloromethane was dissolved 60 mg of the Compound (50) obtained in Example 50. To the solution was added 20 mg of 3-chloroperbenzoic acid. The mixture was stirred at room temperature for 30 minutes. The reaction solution was washed with an aqueous solution of sodium hydrogen carbonate and water, successively, followed by drying (Na$_2$SO$_4$). The solvent was then evaporated off, and the residue was dissolved in 1 ml of toluene. The solution was heated at 80° C. for 30 minutes, then the solvent was evaporated off. The residue was subjected to a silica gel column chromatography, followed by elution with hexane-ethyl acetate (1:1) to give 21 mg of the subject Compound (51) as colorless crystals. The IR and NMR spectra of this product were in agreement with those of the compound obtained in (a) above.

EXAMPLE 52

Production of 4-nitrobenzyl 2-[(4S*,5R*)-4-benzyloxycarbonylamino-5-methoxycarbonyl-3-oxo-2-isoxazolidinyl]-5-oxo-2-tetrahydrofurancarboxylate [Compound (52)]:

In 6 ml of dichloromethane were dissolved 89 mg of (4S*,5R*)-4-benzyloxycarbonylamino-5-methoxycarbonyl-3-isoxazolidinone as obtained in Reference Example 7 and 93 mg of 1-(4-nitrobenzyl) 2-oxoglutarate. To the solution was added 68 mg of DCC, and the mixture was stirred at room temperature for 30 minutes. Insolubles which separated out were filtered off and washed with dichloromethane, the filtrate was contentrated, and the concentrate was subjected to a silica gel column chromatography, followed by elution with hexaneethyl acetate (2:3) to give 104 mg of the subject Compound (52) as white foamy product.

IR$\nu_{max}$ $^{Neat}$ cm$^{-1}$:3320,1805,1770–1710,1525, 1350,1240,1180,1050.

NMR(90 MHz, CDCl$_3$)δ:2.3–3.3(4H,m), 3.75(3H,s),4.5–5.1(2H,m),5.10(2H,s),5.33 (2H,s),5.94(1H,d,J=7 Hz),7.31(5H,s),7.49, 7.52(each 1H,d,J=8 Hz),8.17(2H,d,J=8 Hz).

EXAMPLE 53

Production of sodium 2-{(4S*,5R*)-4-[2-(2-amino-4-thiazolyl)-(Z)-2-(methoxyimino)acetamido]-5-methoxycarbonyl-3-oxo-2-isoxazolidinyl}-5-oxo-2-tetrahydrofurancarboxylate [Compound (53)]:

In a mixture of 3 ml of ethyl acetate and 3 ml of water was dissolved 104 mg of the Compound (52) obtained in Example 52. To the solution was added 100 mg of 5% palladium-carbon. The mixture was stirred at room temperature for 45 minutes in hydrogen streams. The catalyst was filtered off and washed with water. The filtrate and washing were combined and the aqueous layer was taken, to which was added 10 ml of tetrahydrofuran. To the mixture were added, under ice-cooling and stirring, 81 mg of 2-(2-chloroacetamido-4-thiazolyl)-(Z)-2-methoxyiminoacetyl chloride hydrochloride and an aqueous solution of sodium hydrogen carbonate. While keeping the pH at around 7.0, the reaction was allowed to proceed for 30 minutes. To the reaction mixture was added 62 mg of sodium N-methyldithiocarbamate. The mixture was stirred at room temperature for one hour. Tetrahydrofuran was evaporated off under reduced pressure. Thus concentrated solution was washed with ethyl acetate, followed by purification by means of an XAD-2 column. The factions eluted with water and 5% ethanol were combined and lyophilized to give 24 mg the subject Compound (53).

IR$\nu_{max}^{KBr}$cm$^{-1}$:1780,1760–1730,1665,1530,1040.

NMR(90 MHz,D$_2$O)δ:2.3–3.3(4H,m),3.79, 3.82(each 1.5H,s),3.91(3H,s),4.9–5.6(2H,m), 6.90(1H,s).

EXAMPLE 54

Production of 4-nitrobenzyl 2-[(4S*,5S*)-4-benzyloxycarbonylamino-5-methoxycarbonyl-3-oxo-2-isoxazolidinyl]-5-oxo-2-tetrahydrofurancarboxylate [Compound (54)]:

In 6 ml of dichloromethane were dissolved 69 mg of (4S*,5S*)-4-benzyloxycarbonylamino-5-methoxycarbonyl-3-isoxazolidinone obtained in Reference Example 8 and 60 mg of 1-(4-nitrobenzyl) 2-oxoglutarate. To the solution was added 71 mg of 1 -ethoxycarbonyl-2-ethoxy-1,2-dihydroquinoline, which was allowed to stand for 18 hours. The reaction solution was concentrated under reduced pressure. The concentrate was subjected to a silica gel column chromatography, followed by elution with hexane-ethyl acetate (1:1) to give 114 mg of the subject Compound (54) as white foamy product.

IR$\nu_{max}^{Neat}$ cm$^{-1}$:3360,1805,1770–1720,1525,1350,1240,1180,1-060.

NMR(90 MHz, CDCl$_3$)δ:2.3–3.4(4H,m), 3.63(3H,s),5.0–5.5(2H,m),5.09(2H,s),5.34(2H,s),5.8-3,6.02(each 0.5H,d,J=6 Hz),7.31(5H,s),7.50,8.17(each 2H,d,J=9 Hz).

EXAMPLE 55

Production of sodium 2-{(4S*,5S*)-4-[2-(2-amino-4-thiazolyl)-(Z)-2-(methoxyimino)acetamido]-5-methoxycarbonyl-3-oxo-2-isoxazolidinyl}-5-oxo-2-tetrahydrofurancarboxylate [Compound (55)]:

Using 114 mg of the Compound (54) obtained in Example 54, the reaction was allowed to proceed by the procedure of Example 53 to give 50 mg of the subject Compound (55).

IR$\nu_{max}^{KBr}$cm$^{-1}$:1780,1775,1740,1660,1530,1380,1200,1040

NMR(90 MHz, D$_2$O)δ:2.3–3.3(4H,m),3.68, 3.71(each 1.5H,s),3.93(3H,s),4.9–5.6(2H,m), 6.92(1H,s).

EXAMPLE 56

Production of 4-nitrobenzyl 2-(4-benzyloxycarbonyl-5-carbamoyl-3-oxo-2-isoxazolidinyl)-5-oxo-2-tetrahydrofurancarboxylate [Compound (56)]:

In 2.4 ml of concentrated ammonia water was dissolved 150 mg of 4-benzyloxycarbonylamino-5-methoxycarbonyl-3-isoxazolidinone (mixture of 4,5-cis compound and -trans compound). The solution was left standing at room temperature for 20 minutes, which was concentrated to dryness under reduced pressure. Ether was added to the concentrate to give 138 mg of 4-benzyloxycarbonylamino-5-carbamoyl-3-isoxazolidinone as crystals.

IR$\nu_{max}^{KBr}$cm$^{-1}$:3325,1730–1670,1530,1260

Then, in 10 ml of dichloromethane were suspended 130 mg of the above product and 131 mg of 1-(4-nitrobenxzyl)-2-oxoglutarate. To this suspension was added 141 mg of 1-ethoxycarbonyl-2-ethoxy-1,2-dihydroquinoline, and the mixture was stirred vigorously for 2.5 hours at room temperature. The solvent was evaporated off under reduced pressure, and the residue was subjected to a silica gel column chromatography, followed by elution with ethyl acetate to give 166 mg of the subject Compound (56) as colorless oil.

IR$\nu_{max}^{Neat}$cm$^{-1}$:3330,1800,1750(shoulder), 1730–1680,1525,1350

NMR(90 MHz, CDCl$_3$)δ:2.3–3.4(4H,m),4.5–5.2(2H,m),5.05(2H,s),5.34(2H,s),6.4–7.1(3H,bs), 7.28(5H,s),7.3–8.3(4H,m)

EXAMPLE 57

Production of sodium 2-{4-[2-(2-amino-4-thiazolyl)-(Z)-(methoxyimino)acetamido]-5-carbamoyl-3-oxo-2-isoxazolidinyl}-5-oxo-2-tetrahydrofurancarboxylate [Compound (57)]:

Using 166 mg of Compound (56), the reaction was allowed to proceed by the procedure of Example 53 to give 64 mg of the subject compound (57) as pale brown powder.

IR$\nu_{max}^{KBr}$cm$^{-1}$:1780,1690,1650,1490,1200,1040

NMR(90 MHz, D$_2$O)δ:2.3–3.4(4H,m),3.93(3H,s),4.9–5.5(2H,m),6.95,7.00(each 0.5H,s)

EXAMPLE 58

Production of 1-pivaloyloxymethyl 2-oxoglutarate [Compound (58)]:

In 20 ml of N,N-dimethylformamide were dissolved 2.93 g of 2-oxoglutaric acid and 3.48 ml of N,N-diisopropyl ethylamine. To the solution were added 3.13 g of sodium iodide and 3.02 ml of chloromethyl pivalate. The mixture was stirred at room temperature for two hours, which was diluted with ethyl acetate. The cryslats which separated out were filtered off. The filtrate was concentrated to dryness under reduced pressure. To the concentrate was added ethyl acetate, followed by washing with water and drying (MgSO$_4$). The solvent was evaporated off, and the residue was subjected to a silica gel chromatography, followed by elution with dichloromethane—ethylacetate (1:1) to give 1.52 g of the subject Compound (58) as colorless oil.

IR$\nu_{max}^{Neat}$ cm$^{-1}$:2970,1750,1710

NMR(90 MHz, CDCl$_3$)δ:1.24(9H,s),2.67–3.19(4H,m),5.89(2H,s)

EXAMPLE 59

Production of pivaloyloxymethyl 2-[5-phenyl-4-(2-thienylacetamido)-3-oxo-2-isoxazolidinyl]-5-oxo-2-tetrahydrofurancarboxylate [Compound (59)]:

From 100 mg of 5-phenyl-4-(2-thienylacetamido)-3-isoxazolidinone obtained in Reference Example 9 and 127 mg of Compound (58), there was obtained 129 mg of the subject compound (59) by a procedure of Example 2 as colorless foamy product.

IR$\nu_{max}^{KBr}$cm$^{-1}$:3300,1800,1780,1750,1655

NMR(90 MHz, CDCl$_3$)δ:1.20(9H,s),2.33–3.20(4H,m),3.20(1H,s),3.23(1H,s),5.66–5.96(3H,m),6.50–6.63(1H,m),6.73–7.00(1H,m), 7.03–7.43(6H,m)

Mass Spectrum m/e:5 4 5 (M$^+$ +1)

EXAMPLE 60

Production of pivaloyloxymethyl 2-[5-phenyl-4-(2-phenylacetamido-3oxo-2-isoxazolidinyl]-5-oxo-2-tetrahydrofurancarboxylate [Compound (60)]:

From 330 mg of 5-phenyl-4-(2-phenylacetamido)-3-isoxazolidinone obtained in Reference Example 10 and 435 mg of Compound (58), there was obtained 320 mg of the subject compound (60) as pale brown foamy product by a procedure of Example 2.

IR$\nu_{max}^{KBr}$cm$^{-1}$:1800,1740,1650–1660

NMR(90 MHz, CDCl$_3$)δ:1.15(9H,s),2.30–3.00(4H,m),3.27,3.30;3.45,3.51(2H, each s), 5.21–5.39(1H,m),5.69–5.81(2H,m)6.69–7.00 (1H,m),7.03–7.36(10H,m)

Mass Spectrum m/e:5 3 9 (M$^+$ +1)

EXAMPLE 61

Production of diphenylmethyl 2-{4-[2-(2-chloroacetamido-4-thiazolyl)-(Z)-2-(methoxyimino)acetamido]-5-phenyl-3-oxo-2-isoxazolidinyl-}-5-oxo-2-tetrahydrofurancarboxylate [Compound (61)]:

From 220 mg of 4-[2-(2-chlaoroacetamido-4-thiazolyl)-(Z)-2-(methoxyimino)acetamido]-5- phenyl-3-isoxazolidinone obtained in Reference Example 11 and 215 mg of Compound (42), there was obtained 170 mg of the subject compound (61) as colorless foamy product by a procedure of Example 2.

IR$\nu_{max}^{KBr}$cm$^{-1}$:3300,2930,1800,1730,1690,1620,1450,695

NMR(90 MHz, CDCl$_3$)δ:2.33–2.83(4H,m),4.00(3H,s), 4.19(2H,bs),6.96,7.00(1H, each s),7.21–7.33(15H,m), 7.73(1H,s)

EXAMPLE 62

Production of 1-(4-nitrobenzyl) 4-phenyl-2-oxoglutarate [Compound (62)]:

In 30 ml of a N,N-dimethylformamide was dissolved 4.26 g of 4-phenyl-2-oxoglutaric acid. To the solution were added 2.67 ml of dicyclohexylamine and 2.9 g of 4-nitrobenzyl bromide, and the mixture was stirred at room temperature for 20 hours. The reaction solution was diluted with ethyl acetate, and the cryslats which separated out were filterred off. The filtrate was washed with water and dried (MgSO$_4$), followed by distilling off the solvent. The residue was chromatographed on silica-gel. Elution with hexane-ethyl acetate (2:1→1:1) gave 2.89 g of the subject Compound (62) as pale yellow crystals. Recrystallization from ethyl acetate-hexane afforded pale yellow prisms, m.p. 149°–150° C.

IR $\nu_{max}^{KBr}$ cm$^{-1}$:1760,1740,1710,1600
NMR(90 MHz, CDCl$_3$)δ:2.5–4.5(3H,m), 5.40(2H,s),7.30(5H,s),7.68(2H,d,J=9 Hz), 8.24(2H,d,J=9 Hz)

EXAMPLE 63

Production of 4-nitrobenzyl 2-chloro-4-phenyl-5-oxo-2-tetrahydrofurancarboxylate [Compound (63)]:

In 4 ml of 1,2-dichloroethane was dissolved 100 mg of the Compound 62 obtained in Example 62. To the solution was added 0.1 ml of thionyl chloride, and the mixture was heated for 4 hours under reflux. The solvent was evaporated off, then the residue was chromatographed on Florisil, followed by elution with hexane-ethyl acetate (2:1) to give 63 mg of the subject Compound (63) as pale yellow crystals.

IR$\nu_{max}^{Neat}$ cm$^{-1}$:1820,1760,1610
NMR(90 MHz, CDCl$_3$)δ:3.08(1H,dd,J=14,22 Hz), 3.20(1H,dd,J=8,22 Hz),4.33(1H,dd,J=8,14 Hz), 5.44(2H,s),7.34(5H,m),7.57(2H,d,J=9 Hz),8.25(2H,d,J=9 Hz)

EXAMPLE 64

Production of 4-nitrobenzyl 2-[(4S)-4-benzyloxycarbonylamino-3-oxo-2-isoxazolidinyl]-4-phenyl-5-oxo-2-tetrahydrofurancarboxylate [Compound (64)]: In a mixture of 220 mg of (4S)-4-benzyloxycarbonylamino-3-isoxazolidinone and 20 ml of dichloromethane was dissolved 400 mg of the Compound (62) obtained in Example 62. To the solution was added 250 mg of DCC dissolved in 5 ml of dichloromethane. The whole mixture was stirred at room temperature for 2.5 hours. The crystals which separated out were filtered off, and the filtrate was washed with an aqueous sodium hydrogen carbonate solution and water, successively, and dried (MgSO$_4$). Then, the solvent was evaporated off, and the residue was chromatographed on silica gel, followed by elution with hexane—ethylacetate (3:1→2:1) to give 325 mg of the subject Compound (64) as pale yellow oily product.

IR$\nu_{max}^{Neat}$cm$^{-1}$:1790,1700–1780,1600
NMR(90 MHz, CDCl$_3$)δ:2.3–5.1(4H,m),5.37(2H,m), 7.33(10H,s),7.52(2H,bd.,J=10 Hz),8.18,8.20(2H,each d,J=10 Hz) Mass Spectrum m/e:5 7 5 (M$^+$)

EXAMPLE 65

Production of Compound(64): In 6 ml of dichloromethane was suspended 280 mg of (4S)-4-benzyloxycarbonylamino-3-isoxazolidinone. To the suspension were added, under ice-cooling and stirring, 0.36 ml of triethylamine and 490 mg of the Compound (63) obtained in Example 63 dissolved in 1 ml of dichloromethane. The reaction was solution stirred at room temperature for 30 minutes, which was washed with water and dried (MgSO$_4$). The solvent was evaporated off, and the residue was chromatographed on silica gel, followed by elution with hexane-ethylacetate (3:1) to give 470 mg of the subject Compound (64) as colorless oily product. The IR and NMR spectra of this product were in agreement with those of the Compound (64) obtained in Example 64.

EXAMPLE 66

Production of sodium 2-{(4S)-4-[2-(2-amino-4-thiazolyl)-(Z)-2-(methoxyimino)acetamido]-3-oxo-2-isoxazolidinyl}-4-phenyl-5-oxo-2-tetrahydrofurancarboxylate [Compound (66)]:

In a mixture of 10 ml of ethyl acetate and 15 ml of a phosphate buffer solution of pH7.0 was dissolved 432 mg of the Compound (64) obtained in Example 65. The solution was stirred for 1.5 hour under ice-cooling in hydrogen streams. The catalyst was filtered off and washed with water. The filtrate and the washing were combined. The aqueous layer was taken, to which were added 10 ml of tetrahydrofuran and 179 mg of sodium hydrogen carbonate. To the mixture was added, under ice-cooling and stirring, 266 mg of 2-(2-chloroacetamide-4-thiazolyl)-(Z)-methoxyiminoacetyl chloride hydrochloride. The mixture was stirred for 30 minutes under ice-cooling, then tetrahydrofuran was evaporated off. The aqueous layer was washed with ethyl acetate. To the aqueous layer was added 10 ml of tetrahydrofuran, to which was added 173 mg of sodium N-methyldithiocarbamate. The mixture was stirred at room temperature for 30 minutes. Tetrahydrofuran was evaporated off under reduced pressure. The concentrate was washed with ethyl acetate, followed by purification by means of an HP-20 column. The fractions eluted with water-ethanol (5:1) were lyophilized to give 220 mg of the subject Compound (66).

IR$\nu_{max}^{KBr}$ cm$^{-1}$:1780,1720,1650
NMR(90 MHz, D$_2$O)δ:2.3–4.0(3H,m),4.23(3H,s). 4.5–5.5(3H,m),7.26(1H,s),7.64(5H,s)

EXAMPLE 67

Production of 1-(4-nitrobenzyl) 3,3-dimethyl-2-oxoglutarate [Compound (67)]:

In 70 ml of 0.43M aqueous solution of sodium hydroxide was dissolved 1.57 g of 3,3-dimethyl-4-oxopentanoic acid. To the solution was added under ice-cooling and stirring 20 ml of a 1.15M aqueous solution of potassium permanganate. The mixture was stirred under ice-cooling for 4 hours, to which was added an aqueous solution of sodium hydogen sulfite. Then the resultant precipitates were filtered off. The filtrate was adjusted to pH 1 with 6N-HCl, followed by extraction with ethyl acetate. The extract solution was washed with water and dried, followed by evaporating off the solvent to leave 1.73 g of 3,3-dimethyl-2-oxoglutaric acid as a colorless oily product. This oily product was dissolved in 15 ml of N,N-dimethylformamide. To the solution were added 1.08 ml of dicyclohexylamine and 1.18 g of 4-nitrobenzyl bromide. The mixture was stirred at room temperature for 20 hours. The reaction solution was diluted with ethyl acetate and the crystals which separated out were filtered off. The filtrate was washed with water and dried (MgSO$_4$), followed by evaporating off the solvent. The residue was chromatographed on silica gel. Elution with hexane-ethyl acetate (2:1) afforded 1.30 g of the subject Compound(67) as colorless crystals. Recrystallization from ethyl acetate yielded colorless prisms, m.p. 134°–135° C.

IR$\nu_{max}^{KBr}$ cm$^{-1}$:1750,1600 NMR(90 MHz, d$_6$—DMSO)δ:1.10(6H,s), 2.4–2.6(2H,b),5.37(2H,s),7.68(2H,d,J=9 Hz), 8.25(2,d,J=9 Hz)

EXAMPLE 68

Production of 4-nitrobenzyl 2-[(4S)-4-benzyloxycarbonylamino-3-oxo-2-isoxazolidinyl]-3,3-dimethyl-5-oxo-2-tetrahydrofurancarboxylate [Compound(68)]:

In 40 ml of dichloromethane were dissolved 436 mg of (4S)-4-benzyloxycarbonylamino-3-isoxazolidinone and 600 mg of the Compound (67) obtained in Example 67. To the solution was added a solution of 495 mg of DCC in 5 ml of dichloromethane. The mixture was stirred at room temperature for 3 hours. The crystals which separated out were filtered off, and the filtrate was concentrated. The crystals which separated out again were filtered off, and the filtrate was diluted with ethyl acetate. The solution was washed with water and dried (MgSO$_4$). The solvent was evaporated off, and the residue was subjected to a silica gel column chromatography, followed by elution with hexane-ethyl acetate to give 133 mg of the subject Compound (68) as colorless oily product.

IR$\nu_{max}^{Neat}$ cm$^{-1}$:1820,1720,1620

NMR(90 MHz, CDCl$_3$)δ:1.06(3H,s),1.40(3h,s). 2.46(1H,d,J=18 Hz),2.64(1H,d,J=18 Hz),5.14(2H,s), 5.29(1H,d,J=14 Hz),5.36(1H,d,J=14 Hz),7.37(5H,s), 7.54(2H,d,J=9 Hz),8.20(2H,d,J=9 Hz)

Mass Spectrum m/e:5 2 7 (M+)

EXAMPLE 69

Production of sodium 2-{(4S)-4-[2-(2-amino-4-thiazolyl)-(Z)-2-(methoxyimino)acetamido]-3-oxo-2-isoxazolidinyl}-3,3-dimethyl-5-oxo-2-tetrahydrofuran-carboxylate [Compound (69)]:

In a mixture of 4.5 ml of ethyl acetate and 6.5 ml of a phosphate buffer of pH 7.0 was dissolved 187 mg of the Compound (68) obtained in Example 68. To the solution was added 190 mg of 10% palladium-carbon, and the mixture was stirred for 1.5 hour in hydrogen streams. The catalyst was filtered off and washed with water. The filtrate and the washing were combined, and the aqueous layer was taken. To the aqueous layer were added 6.5 ml of tetrahydrofuran and 85 mg of sodium hydrogen carbonate. To the mixture was added, while stirring under ice-cooling, 126 mg of 2-(2-chloroacetamido-4-thiazolyl)-(Z)-2-methoxy-iminoacetyl chloride hydrochloride. The mixture was stirred for 30 minutes under ice-cooling, followed by evaporating off tetrahydrofuran. The aqueous layer was washed with ethyl acetate, to which was added 6.5 ml of tetrahydrofuran, followed by addition of 82 mg of sodium N-methyl dithiocarbamate. The mixture was stirred at room temperature for 30 minutes. Tetrahydrofuran was evaporated off, and the resultant concentrate was washed with ethyl acetate, followed by purification by means of an HP-20 column. The fractions eluted with water-ethanol (20:1) were lyophilized to give 16 mg of the subject Compound (69) as white powder.

IR$\nu_{max}^{KBr}$ cm$^{-1}$:1770(b),1650

NMR(90MHz,D$_2$O)δ:1.40(3H,s),1.64(3H,s),2-.5–3.5(2H,m),4.20(3H,s),4.5–5.5(3H,m), 7.23(1H,s)

Mass Spectrum m/e:464(M++1) (SIMS)

EXAMPLE 70

Production of 1-(4-nitrobenzyl) 3-(2-acetamidoethylthio)-2-oxoglutarate [Compound (70)]:

In 20 ml of dichloromethane was suspended 1.0 g of 3-bromo-2-oxoglutaric acid. To the suspension was added, while stirring under ice-cooling, 0.5 g of 2-acetamidoethanethiol, followed by addition of 1.83 ml of triethylamine. The reaction solution was stirred at room temperature for one hour, then the solvent was evaporated off. To the residue were added ethyl acetate and water. The aqueous layer was taken, which was adjusted to pH 1~2 with 1N-HCl, followed by extraction with ethyl acetate. The extract solution was washed with water and dried (MgSO$_4$), followed by evaporating off the solvent to give 0.67 g of 3-(2-acetamidoethylthio)-2-oxoglutaric acid as a pale yellow oily product. To this product were added, while stirring under ice-cooling, 0.32 ml of dicyclohexylamine and 0.34 g of 4-nitrobenzyl bromide. The reaction solution was stirred for 15 hours at room temperature, followed by dilution with ethyl acetate. The crystals which separated out were filtered off, and the filtrate was washed with water and dried (MgSO$_4$), followed by evaporating off the solvent. The residue was subjected to a silica gel column chromatography, followed by elution with ethyl acetate then with ethyl acetate—acetic acid (100:3) to give 0.4 g of the subject Compound (70) as a pale yellow oily product.

IR$\nu_{max}^{Neat}$cm$^{-1}$:3350,1730(b),1640(b), 1525,1375,1350,1250

NMR(90MHz, CDCl$_3$)δ:1.95(3H,s),2.67(2H,t,J=6Hz), 2.9(2H,b),3.43(2H,dd,J=6,12Hz),4.3(1H,b),5.43(2-H,s), 6.2(1H,b),7.58(2H,d,J=9Hz),8.27(2H,d,J=9Hz)

EXAMPLE 71

Production of 4-nitrobenzyl 2-[(4S)-4-phenylacetamido-3-oxo-2-isoxazolidinyl]-3-(2acetamidoethylthio)-5-oxo-2-tetrahydrofurancarboxylate [Compound (71)]:

In 5 ml of dichloromethane were suspended 48 mg of (4S)-4-phenylacetamido-3-isoxazolidinone and 95 mg of the Compound (70) obtained in Example 70. To the suspension was added 71 mg of 1-ethoxycarbonyl-2-ethoxy-1,2-dihydroquinoline. The mixture was stirred for 5.5 hours at room temperature. The solvent was evaporated off, and the residue was subjected to a silica gel column chromatography, followed by elution with ethyl acetate to give 75 mg of the subject Compound (71) as a colorless oily product.

IR$\nu_{max}^{Neat}$cm$^{-1}$:3300,1800,1750,1650,1600

NMR(90MHz,CDCl$_3$)δ:1.93(3H,s),3.04(2H,t,J=7H-z), 3.40(2H,t,J=7Hz),3.5–5.4(10H,m),6.4(1H,b),7.28(-5H,s), 7.50(2H,d,J=9Hz),8.0–8.3(2H,m)

Mass Spectrum m/e:600(M+)

EXAMPLE 72

Production of sodium 2-[(4S)-4-phenylacetamido-3-oxo-2-isoxazolidinyl]-3-(2-acetamidoethylthio)-5-oxo-2-tetrahydrofurancarboxylate [Compound (72)]:

In a mixture of 6 ml of ethyl acetate and 4 ml of a phosphate buffer of pH 7.0 was dissolved 168 mg of the Compound (71) obtained in Example 71. To the solution was added 170 mg of 10% palladium-carbon, and the mixture was stirred in hydrogen streams for 1.5 hour under ice-cooling, then for 0.5 hour at room temperature. The catalyst was filtered off and washed with water. The filtrate and the washing were combined, and the aqueous layer was taken. The aqueous layer was concentrated under reduced pressure. The concentrate was subjected to a column chromatography using HP-20, followed by elution with water-ethanol (10:1). The resultant fraction was lyophilized to give 40 mg of the subject Compound (72) as white powder.

IR$\nu_{max}^{KBr}$cm$^{-1}$:1780,1720,1650

NMR(90MHz,D$_2$O)δ:2.23(3H,s),2.8–3.8(6H,m), 3.91(2H,s),4.0–5.4(4H,m),7.60(5H,s)

EXAMPLE 73

Production of 1-(4-nitrobenzyl) 4-benzyl-2-oxoglutarate [Compound (73)]:

Under nitrogen atmosphere at −78° C., 4.29 ml of 1.5 M n-butyl lithium (hexane solution) was added, while stirring, to 0.98 ml of diisopropylamine dissolved in 13 ml of anhydous tetrahydrofuran. The stirring was conducted for 15 minutes. To the resultant was added, taking 5 minutes, 1.18 g of dimethyl 2-oxoglutarate dimethyl acetal dissolved in 7 ml of anhydrous tetrahydrofuran, followed by stirring for 15 minutes. To the mixture was added, taking 5 minutes, a solution of 0.76 ml of benzyl bromide and 0.28 ml of hexamethylphosphoramide in 7 ml of anhydrous tetrahydrofuran. The mixture was stirred for 30 minutes at −78° C. The temperature of the reaction solution was raised up to −20° C. under stirring taking 2 hours, followed by addition of saturated aqueous solution of ammonium chloride, which was subjected to extraction with ethyl acetate. The extract solution was washed with water, dried ($MgSO_4$), followed by evaporating off the solvent. The residue was subjected to a silicagel column chromalography, followed by elution with hexane-ethyl acetate (5:1→2:1) to give 1.64 g of dimethyl 4-benzyl-2-oxoglutarate dimethyl acetal as a pale yellow oily product.

$IR\nu_{max}^{Neat}cm^{-1}$:1740,1600
NMR(90MHz,$CDCl_3$)δ:2.2–3.0(5H,m),3.07(3H,s), 3.17(3H,s),3.57(3H,s),3.68(3H,s),7.0–7.4(5H,m)

This product was dissolved in 10 ml of methanol, to which was added 15 ml of a 3.5 M aqueous solution of potassium hydroxide. The mixture was stirred at room temperature for 3.5 hours, followed by evaporating off methanol. To the reaction solution was added 6N HCl to render the pH to 1. The mixture was saturated with sodium chloride, followed by extraction with ethyl acetate. The extract solution was washed with a saline solution, which was dried ($Na_2SO_4$), followed by evaporating off the solvent to give 1.43 g of 4-benzyl-2-oxoglutaric acid dimethyl acetal as a yellow oily product. This oily product was dissolved in 40 ml of tetrahydrofuran. To the solution was added 40 ml of 1N HCl, and the mixture was stirred for 30 minutes. Tetrahydrofuran was evaporated off and the aqueous layer was saturated with sodium chloride, followed by extraction with ethyl acetate. The extract solution was washed with a saline solution, which was dried ($Na_2SO_4$). Then, the solvent was evaporated off to give 1.40 g of 4-benzyl-2-oxoglutaric acid as a yellow oily product. This oily product was dissolved in 10 ml of N,N-dimethylformamide. To the solution were added 0.83 ml of dicyclohexylamine and 0.90 g of 4-nitrobenzylbromide. The mixture was stirred at room temperature for 15 hours. To the reaction solution was added ethyl acetate. The crystals which separated out were filtered off, and the filtrate was washed with water, then dried ($MgSO_4$), followed by evaporating off the solvent. The residue was subjected to a silica gel column chromatography, followed by elution with hexane-ethyl acetate (2:1) to give 1.35 g of the subject Compound (73) as a colorless oily product.

$IR\nu_{max}^{Neat}cm^{-1}$:3700–3200,3150–3000, 1760(b),1600
NMR(90MHz,$CDCl_3$)δ:2.5–3.4(5H,m), 5.30(2H,s),7.0–7.4(5H,m),7.45(2H,d,J=9Hz), 8.18(2H,d,J=9Hz)
Mass Spectrum m/e:371($M^+$)

EXAMPLE 74

Production of 4-nitrobenzyl 4-benzyl-2-chloro-5-oxo-2-tetrahydrofurancarboxylate [Compound (74)]:

In 18 ml of 1,2-dichloroethane was dissolved 475 mg of the Compound (73) obtained in Example 73. The solution was heated for 5 hours under reflux. The solvent was evaporated off, and the residue was subjected to a column chromatography using Florisil, followed by elution with hexaneethyl acetate (5:1) to give 370 mg of the subject Compound (74) as a pale yellow oily product.

$IR\nu_{max}^{Neat}cm^{-1}$:1810,1760,1600
NMR(90MHz,$CDCl_3$)δ:2.3–3.6(5H,m), 5.37(2H,s),7.0–7.5(5H,m),7.52(2H,d,J=9Hz), 8.22(2H,d,J=9Hz)
Mass Spectrum m/e:389,391($M^+$)

EXAMPLE 75

Production of 4-nitrobenzyl 2-[(4S)-4-benzyloxycarbonylamino-3-oxo-2-isoxazolidinyl]-4-benzyl-5-oxo-2-tetrahydrofurancarboxylate [Compound (75)]:

In 6 ml of dichloromethane were dissolved 286 mg of (4S)-4-benzyloxycarbonylamino-3-isoxazolidinone and 540 mg of the Compound (73) obtained in Example 73. To the solution was added 325 mg of DCC dissolved in 2 ml of dichloromethane. The mixture was stirred at room temperature for 2 hours. To the reaction solution was added ethyl acetate, and the crystals which separated out were filtered off. The filtrate was washed with water and dried ($Na_2SO_4$), followed by evaporating off the solvent. The residue was subjected to a silica gel column chromatography, followed by elution with hexane-ethyl acetate (2:1) to give 553 mg of the subject Compound (75) as a pale yellow oily product.

$IR\nu_{max}^{Neat}cm^{-1}$:1790,1780–1700,1600
NMR(90 MHz,$CDCl_3$)δ:2.6–3.5(5H,m),3-.9–4.3(1H,m), 4.4–4.9(2H,m),5.10(2H,s),5.27(2H,s),5.36(1H,b) 7.0–7.6(12H,m)
Mass Spectrum m/e:589($M^+$)

EXAMPLE 76

Production of Compound (75):

In 1 ml of dichloromethane were dissolved 55 mg of (4S)-4-benzyloxycarbonylamino-3-isoxazolidinone and 0.07 ml of triethylamine. To the solution was added, under ice-cooling while stirring, 100 mg of the Compound (74) obtained in Example 74. The reaction solution was stirred at room temperature for 30 minutes, to which was added 25 ml of ethyl acetate. The mixture was washed with water, an aqueous solution of sodium hydrogen carbonate and water, successively, which was then dried ($MgSO_4$), followed by evaporating off the solvent. The residue was subjected to a silica gel column chromatography, followed by elution with hexane-ethyl acetate (2:1) to give 70 mg of the subject Compound (75) as a pale yellow oily product. The IR and NMR spectra are in agreement with those of the Compound (75) obtained in Example 75.

EXAMPLE 77

Production of sodium 2-{(4S)-4-[2-(2-amino-4-thiazolyl)-(Z)-2-(methoxyimino)acetamido]-3-oxo-2-isoxazolidinyl}-4-benzyl-5-oxo-2-tetrahydrofurancarboxylate [Compound (77)]:

In a mixture of 8 ml of ethyl acetate and 12 ml of a phosphate buffer solution of pH 7.0 was dissolved 318 mg of the Compound (75) obtained in Example 75. To the solution was added 318 mg of 10% palladium-carbon, and the mixture was stirred in hydrogen streams under ice-cooling for 1.5 hour. The catalyst was filtered off, and the filtrate was washed with ethyl acetate. To the aqueous layer were added 12 ml of tetrahydrofuran and 130 mg of sodium hydrogen carbonate. To the mixture was added, under cooling with ice while stirring, 191 mg of 2-(2-chloroacetamido-4-thiazolyl)-(Z)-2-methoxyiminoacetyl chloride hydrochloride. The mixture was stirred under ice-cooling for 30 minutes. Then, tetrahydrofuran was distilled off, and the aqueous layer was washed with ethyl acetate. To the aqueous layer was added 12 ml of tetrahydrofuran, to which was further added 125 mg of sodium N-methyl dithiocarbamate. The mixture was stirred at room temperature for one hour. Tetrahydrofuran was evaporated off under reduced pressure, and the concentrate was washed with ethyl acetate, followed by purification by means of an HP-20 column. The fraction eluted with water-ethanol (5:1) was lyophilized to give 110 mg of the subject Compound (77) as white powder.

IR$\nu_{max}^{KBr}$cm$^{-1}$:1780,1730,1650

NMR(90MHz,D$_2$O)δ:2.6–3.8(5H,m),4.18(3H,s), 4.2–5.1(2H,m),5.4(1H,m),7.21(1H,s),7.57(5H,s)

EXAMPLE 78

Production of 1-(4-nitrobenzyl) 4-methoxymethyl-2-oxoglutarate [Compound (78)]:

To 2.85 ml of diisopropylamine dissolved in 30 ml of anhydrous tetrahydrofuran was added 12.5 ml of 1.5M n-butyl lithium (hexane solution) at −78° C. under nitrogen atmosphere. The mixture was stirred for 15 minutes. To the solution was added 3.45 g of dimethyl 2-oxoglutarate dimethyl acetal in 15 ml of anhydrous tetrahydrofuran, taking 10 minutes. The mixture was stirred for 15 minutes. To the mixture was added a solution of 1.32 ml of chloromethyl methylether and 1.36 ml of hexamethylphosphoramide in anhydrous tetrahydrofuran, taking 10 minutes. The temperature of the reaction mixture was raised up to −20° C. taking 30 minutes, followed by stirring at the same temperature for 3 hours. To the reaction solution was added a saturated aqueous solution of ammonium chloride, followed by extraction with ethyl acetate. The extract solution was washed with water and dried (MgSO$_4$). The solvent was evaporated off. The residue was subjected to a silica gel column chromatography, followed by elution with hexaneethyl acetate (2:1) to give 2.28 g of dimethyl 4-methoxymethyl-2-oxoglutarate dimethyl acetal as a pale yellow oily product.

IR$\nu_{max}^{Neat}$cm$^{-1}$:1750

NMR(90MHz,CDCl$_3$)δ:2.02(1H,dd,J=5, 15Hz),2.35(1H,dd,J=9,15Hz),2.75(1H,m), 3.23(6H,s),3.28(3H,s),3.44(1H,d,J=5Hz), 3.46(1H,d,J=6Hz),3.67(3H,s),3.77(3H,s)

To a solution of 560 mg of this product in 4 ml of methanol was added 6 ml of a 1.8M aqueous solution of potassium hydroxide. The mixture was stirred at room temperature for 3 hours. Methanol was evaporated off, and the aqueous layer was washed with ether, to which was added 6N HCl to render the pH to 1, followed by saturation with sodium chloride and extraction with ethyl acetate. The extract solution was washed with a saline and dried (MgSO$_4$), followed by evaporating off the solvent to give 471 mg of 4-methoxymethyl-2-oxoglutaric acid dimethyl acetal as a yellow oily product. This product was dissolved in 10 ml of tetrahydrofuran. To the solution was added 10 ml of 1N HCl, which was stirred at room temperature for 4 days. Tetrahydrofuran was evaporated off, and the aqueous layer was saturated with sodium chloride, followed by extraction with ethyl acetate. The extract solution was washed with a saline and dried (MgSO$_4$), followed by evaporating off the solvent to give 397 mg of 4-methoxymethyl-2-oxoglutaric acid as a colourless oily product.

A 355 mg portion of this oily product was dissolved in 3 ml of N,N-dimethylformamide. To the solution were added 0.30 ml of dicyclohexylamine and 323 mg of 4-nitrobenzyl bromide, and the mixture was stirred at room temperature for 15 hours. To the reaction solution was added ethyl acetate. The crystals which separated out were filtered off, and the filtrate was washed with water and dried (MgSO$_4$). The solvent was evaporated off and the residue was subjected to a silica gel column chromatography, followed by elution with hexane—ethyl acetate (2:1) to give 293 mg of the subject Compound (78) as a yellow oily product.

IR$\nu_{max}^{Neat}$cm$^{-1}$:1750(b),1600

NMR(90MHz,CDCl$_3$)δ:3.05(3H,m),3.48(3H,s), 3.6–3.9(2H,m),5.37(2H,s),7.52(2H,d,J=9Hz), 8.21(2H,d,J=9Hz)

EXAMPLE 79

Production of 4-nitrobenzyl 2-chloro-4-methoxymethyl-5-oxo-2-tetrahydrofurancarboxylate [Compound (79)]:

A 340 mg portion of the Compound (78) obtained in Example 78 was dissolved in 14 ml of 1,2-dichloroethane. To the solution was added 0.34 ml of thionyl chloride, and the mixture was heated for 5 hours under reflux. The solvent was evaporated off, and the residue was subjected to a column chromatography using Florisil, followed by elution with hexane-ethyl acetate (5:1) to give 152 mg of the subject Compound (79) as colourless oily product.

IR$\nu_{max}^{Neat}$cm$^{-1}$:1810,1760

NMR(90MHz,CDCl$_3$)δ:2.8–3.4(3H,m),3.28(3H,s), 3.7(2H,m),5.40(2H,s),7.57(2H,d,J=9Hz),8.23(2H,d,J=9Hz)

EXAMPLE 80

Production of 4-nitrobenzyl 2-[(4S)-4-benzyloxycarbonylamino-3-oxo-2-isoxazolidinyl]-4-methoxymethyl-5-oxo-2-tetrahydrofurancarboxylate [Compound (80)]:

In 2 ml of dichloromethane were dissolved 121 mg of (4S)-4-benzyloxycarbonylamino-3-isoxazolidinone and 200 mg of the Compound (78) obtained in Example 78. To the solution was added a solution of 137 mg of DCC in 1 ml of dichloromethane. The solution was stirred at room temperature for 2 hours. To the reaction solution was added ethyl acetate. The crystals which separated out were filtered off, and the filtrate was washed with water and dried (MgSO$_4$). The solvent was evaporated off, and the residue was subjected to a silica gel column chromatography, followed by elution with hexane-ethyl acetate (2:1) to give 216 mg of the subject Compound (80) as a pale yellow oily product.

IR$\nu_{max}^{Neat}$cm$^{-1}$:1790,1770–1700,1600

NMR(90MHz,CDCl$_3$)δ:2.4–2.8(2H,m),3-.0–3.4(4H,m), 3.5–3.7(2H,m),3.9–4.4(1H,m),4-.5–4.9(2H,m),5.10(2H,s), 5.34(2H,s),5.5(1H,b),7.33(5H,s),7.50(2H,d,J=9Hz), 8.20(2H,d,J=9Hz)

EXAMPLE 81

Production of Compound (80): In 2 ml of dichloromethane was suspended 95 mg of (4S)-4-benzyloxycarbonylamino-3-isoxazolidinone. To the suspension was added under ice-cooling while stirring, a solution of 0.12 ml of triethylamine and 152 mg of the Compound (79) obtained in Example 79 in 1 ml of dichloromethane. The reaction solution was stirred at room temperature for 30 minutes, which was washed with water and dried (MgSO$_4$). Then, the solvent was evaporated off. The residue was subjected to a silica gel column chromatography, followed by elution with hexane-ethyl acetate (2:1) to give 175 mg of the subject Compound (80) as a pale yellow oily product. The IR and NMR spectra of this product were in agreement with those of the Compound (80) obtained in Example 80.

EXAMPLE 82

Production of sodium 2-{(4S)-4-[2-(2-amino-4-thiazolyl)-(Z)-2-(methoxyimino)acetamido]-3-oxo-2-isoxazolidinyl}-4-methoxymethyl-5-oxo-2-tetrahydrofurancarboxylate [Compound (82)]:

In a mixture of 5 ml of ethyl acetate and 7 ml of a phosphate buffer of pH 7.0 was dissolved 216 mg of the Compound (80) obtained in Example 80. To the solution was added 216 mg of 10% palladium-carbon, and the mixture was stirred in hydrogen streams under ice-cooling for 1.5 hour. The catalyst was filtered off and washed with water. The filtrate and the washing were combined, and the aqueous layer was separated, to which were added 9 ml of tetrahydrofuran and 95 mg of sodium hydrogen carbonate. To the mixture was added, under ice-cooling while stirring, 141 mg of 2-(2-chloroacetamido-4-thiazolyl)-(Z)-2-methoxyiminoacetyl chloride hydrochloride. The whole mixture was stirred for 30 minutes under ice-cooling, then tetrahydrofuran was evaporated off, and the aqueous layer was washed with ethyl acetate. To the aqueous layer was added 9 ml of tetrahydrofuran, to which was then added 93 mg of sodium N-methyldithiocarbamate. The mixture was stirred at room temperature for 30 minutes. Tetrahydrafuran was evaporated off under reduced pressure. The resulting concentrate was washed with ethyl acetate, which was purified by means of an HP-20 column. The fraction eluted with water-ethanol (100:5) was lyophilized to give 140 mg of the subject Compound(82) as a white powdery product.

IR$\nu_{max}^{KBr}$cm$^{-1}$:1780,1720,1660
NMR(90MHz,D$_2$O)$\delta$:2.6–3.5(3H,m),3.54, 3.55(total 3H,each s),3.8–4.2(2H,m),4.19(3H,s), 4.4–5.6(3H,m),7.23(1H,s)

EXAMPLE 83

Production of 5-phenylamino-4,5-dioxopentanoic acid [Compound (83)]:

To an acetonitrile solution (20 ml) of 1.46 g of 2-oxoglutaric acid was added 2.06 g of DCC, and the mixture was stirred at room temperature for 10 minutes. To the mixture was added 930 mg of aniline, which was stirred at room temperature for 5 hours. Resultant white precipitates were filtered off. To the filtrate was added ethyl acetate (40 ml), followed by extraction with an aqueous solution of sodium hydrogen carbonate (30 ml). With 2 N HCl was adjusted the pH of the extract to 3.0, followed by extraction with ethyl acetate. The organic layer was washed with water and dried (MgSO$_4$), which was freed of solvent. The residue was subjected to a silica gel column chromatography, followed by elution with hexaneethyl acetate (1:2) to give 390 mg of the subject Compound (83) as colorless crystals, m.p. 192°–193° C.

IR$\nu_{max}^{KBr}$cm$^{-1}$:3340,1700,1690,1600,1540,1450,1320
NMR(90MHz,CDCl$_3$—d$_6$—DMSO)$\delta$:2.-42–2.70(2H,m), 2.90–3.32(2H,m),7.01–7.90(5H,m)

EXAMPLE 84

Production 5-pyrrolidyl-4,5-dioxopentanoic acid [Compound (84)]:

Using 584 mg of 2-oxoglutaric acid and 284 mg of pyrrolidine, there was obtained 412 mg of the subject compound (84), by conducting a reaction and treatment analogous to Example 83, as colorless crystals, m.p. 101°–102° C.

IR$\nu_{max}^{KBr}$cm$^{-1}$:2970,1730,1710,1600,1390,1330,1210,-1170
NMR(90MHz,CDCl$_3$)$\delta$:1.81–2.06(4H,m), 2.65–2.84(2H,m),3.08–3.27(2H,m),3.-43–3.80(4H,m), 8.60–9.01(1H,m)

EXAMPLE 85

Production of 5-n-propylamino-4,5-dioxopentanoic acid [Compound (85)]:

Using 1.46 g of 2-oxoglutaric acid and 0.828 ml of n-propylamine, there was obtained 496 mg of the subject Compound (85), by conducting a reaction and treatment analogous to Example 83, as pale yellow crystals, m.p. 79°–81° C.

IR$\nu_{max}^{KBr}$cm$^{-1}$:3250,2960,1730,1690,1660,1530,1440,-1400
NMR(90MHz,CDCl$_3$)$\delta$:0.81–1.19(3H,t,J=6Hz), 1.36–1.75(2H,m),2.58–2.72(2H,m),3.-12–3.34(4H,m), 6.79–7.03(1H,m),7.91–8.37(1H,m)

EXAMPLE 86

Production of 2-[(4S)-4-benzyloxycarbonylamino-3-oxo-2-isoxazolidinyl]-5-oxo-2-tetrahydrofurancarboxylylphenylamide [Compound (86)]:

In acetonitrile (25 ml) were dissolved 400 mg of (4S)-4-benzyloxycarbonylamino-3-isoxazolidinone obtained in Reference Example 4 and 372 mg of Compound (83). To the solution was added 416 mg of 1-ethoxycarbonyl-2-ethoxy-1,2-dihydroquinoline, and the mixture was stirred at room temperature for 17 hours. The solvent was evaporated off under reduced pressure. The residue was subjected to a silica gel column chromatography, followed by elution with hexane-ethyl acetate (1:1) to give 124 mg of the subject Compound (86) as colorless crystals.

IR$\nu_{max}^{KBr}$cm$^{-1}$:3320,1800,1730,1690,1530,1250,1180,-1050
NMR(90MHz,CDCl$_3$)$\delta$:2.37–3.54(4H,m), 4.01–4.29(1H,m),4.52–4.79(2H,m),5.10(2H,s), 5.51–5.70(1H,m),7.09–7.60(10H,m),8.-31–8.44(1H,m)

EXAMPLE 87

Production of 2-[(4S)-4-benzyloxycarbonylamino-3-oxo-2-isoxazolidinyl]-5-oxo-2-tetrahydrofurancarboxylylpyrrolidine [Compound (37)]:

Using 400 mg of (4S)-4-benzyloxycarbonylamino-3-isoxazolidinone and 335 mg of Compound (84), there was obtained 72 mg of the subject Compound (87) as a colorless oily product by conducting a reaction and treatment analogous to Example 86.

IR$\nu_{max\text{-}}^{Neat}$cm$^{-1}$:3320,1800,1730,1640,1530,1250,1180,10-20

NMR(90MHz,CDCl$_3$)δ:1.62–2.01(4H,m), 2.39–3.26(4H,m),3.38–3.70(4H,m),4.02–4.29(1H,m), 4.51–4.80(2H,m),5.10(2H,s),5,79–6.20(1H,m), 7.15–7.42(5H,m)

EXAMPLE 88

Production of 2-[(4S)-4-(2-thienylacetamido)-3-oxo-2-isoxazolidinyl]-5-oxo-2-tetrahydrofurancarboxylyl pyrrolidine [Compound (88)]:

In acetonitrile (25 ml) were dissolved 380 mg of (4S)-4-(2-thienylacetamido)-3-isoxazolidinone and 368 mg of Compound (84). To the solution was added 458 mg of 1-ethoxycarbonyl-2-ethoxy-1,2-dihydroquinoline, and the mixture was stirred at room temperature for 23 hours. The solvent was evaporated off, and the residue was subjected to a silica gel column chromatography, followed by elution with hexane-ethyl acetate-acetic acid (6:3:0.1) then with ethyl acetate-acetic acid (10:0.1) to give 80 mg of the subject Compound (88) as a colorless oily product.

IR$\nu_{max\text{-}}^{Neat}$cm$^{-1}$:3270,1790,1720,1680,1540,1180,1040

NMR(90MHz,CDCl$_3$)δ:1.73–2.01(4H,m), 2.41–3.11(4H,m),3.40–3.71(4H,m),3.76,3.78(2-H,each s), 4.10–4.29(1H,m),4.53–4.99(2H,m),6.88–7.28(3H,m)

EXAMPLE 89

Production of 2-[(4S)-4-(2-thienylacetamido)-3-oxo-2-isoxazolidinyl]-5-oxo-2-tetrahydrofurancarboxylyl-n-propylamide [Compound (89)]:

Using 120 mg of (4S)-4-(2-thienylacetamido)-3-isoxazolidinone and 99 mg of Compound (85), a reaction and treatment analogous to Example 86 was conducted to give 30 mg of the subject Compound (89) as a colorless oily product.

IR$\nu_{max\text{-}}^{Neat}$cm$^{-1}$:3270,1800,1720,1680,1540,1180,1040

NMR(90MHz,CDCl$_3$)δ:0.81–1.00(3H,m), 1.38–1.68(2H,m),2.25–3.42(6H,m), 3.70–4.09(1H,m), 3.77(2H,s),4.59–4.98(2H.m),6.87–7.29(3H,m)

EXAMPLE 90

Production of 2-[(4S)-4-(2-thienylacetamido)-3-oxo-2-isoxazolidinyl]-5-oxo-2-tetrahydrofurancarboxylyl-phenylamide [Compound (90)]:

In ethyl acetate (5 ml) was dissolved in 124 mg of Compound (86). To the solution was added 124 mg of 10% palladium-carbon. The mixture was stirred in hydrogen streams at 0° C. for 2 hours. The catalyst was filtered off. To the filtrate were added 0.12 ml of N,N-dimethylacetamide and 45 ml of 2-thiopheneacetyl chloride. The mixture was stirred at 0° C. for 30 minutes. The reaction solution was washed with water and dried (Na$_2$SO$_4$), then the solvent was evaporated off under reduced pressure. The residue was subjected to a silica gel column chromatography, followed by elution with hexane-ethyl acetate (2:3) to give 23 mg of the subject Compound (90) as a colorless oily product.

IR$\nu_{max\text{-}}^{Neat}$cm$^{-1}$:3300,1800,1730,1690,1540,1180,1040

NMR(90MHz, CDCl$_3$)δ:2.37–3.46(4H,m), 3.81–4.08(1H,m),3.80(2H,s),4.57–5.01(2H,m), 6.58–6.83(1H,m),6.83–7.61(8H,m),8.41–8.62(1H,m)

EXAMPLE 91

Production of 1-t-butyl-2-oxoglutarate [Compound (41)]:

(a) In 10 ml of N,N-dimethylformamide were dissolved 1.46 g of 2-oxoglutaric acid and 1.21 g of triethylamine. To the solution was added 1.64 g of t-butyl bromide. The mixture was stirred at 70° C. for 5 hours. The reaction solution was poured into a saturated aqueous saline solution, followed by extraction (twice) with ethyl acetate. The organic layer was washed with water and dried (Na$_2$SO$_4$). The solvent was evaporated off, and the residue was subjected to a silica gel column chromatography, followed by elution with dichloromethane—ethyl acetate (1:1) to give 144 mg of the subject compound as crystals. The melting point, IR and NMR spectra of this product were in complete agreement with those of the Compound (41) obtained in Example 41.

(b) In a mixture of 5 ml of acetonitrile and 10 ml of t-butanol was dissolved 1.46 g of 2-oxoglutaric acid. To the solution were added 2.06 g of DCC and 50 mg of 4-dimethylaminopyridine. The mixture was stirred at room temperature for two days. The reaction solution was given the workup of the reaction mixture similar to that described in the above (a) to give 150 mg of the subject Compound (41) as crystals.

EXAMPLE 92

Production of 1-(2-trimethylsilyl)ethyl-2-oxoglutarate [Compound (92)]:

In 20 ml of acetonitrile was dissolved 1.46 g of 2-oxoglutaric acid. To the solution was added 2.06 g of DCC, and the mixture was stirred at room temperature for 30 minutes. To the resultant were added 1.42 ml of 2-trimethylsilylethanol and 50 mg of 4-dimethylaminopyridine. The mixture was stirred at room temperature for 3.5 hours. Precipitating crystals were filtered off, and the filtrate was concentrated to dryness. The concentrate was subjected to a silica gel column chromatography, followed by elution with hexane—ethyl acetate (1:1) to give 646 mg of the subject Compound (92) as an oily product.

IR$\nu_{max}^{Neat}$cm$^{-1}$:1730,1420,1250,1080,1030,840

NMR(100MHz,CDCl$_3$)δ:0.80–1.20(2H,m),2.50–2.85 (2H,m),2.98–3.20(2H,m),4.16–4.44(2H,m)

EXAMPLE 93

Production of 1-(4-nitrobenzyl) 4-methoxy-2-oxoglutarate [Compound (93)]:

In 300 ml of dichloromethane was dissolved 10 g of 4-hydroxy-2-cyclopentenone. To the solution were added 25.7 g of dihydropyran and 0.5 g of p-toluenesulfonic acid, and the mixture was stirred at room temperature for 45 minutes. The reaction solution was poured into an aqueous solution of sodium hydrogencarbonate. The organic layer was separated. The aqueous layer was further extracted with dichloromethane. The organic layers were combined, washed with a saturated aqueous saline solution, then dried (Na$_2$SO$_4$). The solvent was evaporated off, and the residue was subjected to a silica gel column chromatography, followed by elution with hexane—ethyl acetate (7:3) to give 17.4 g of 4-(2-tetrahydropyranyl)oxy-2-cyclopentenone as an oily product.

IR$\nu_{max}^{Neat}$cm$^{-1}$:2900,1720
NMR(90MHz,CDCl$_3$)δ:1.40–2.03(6H,m),2.27–2.60 (2H,m),3.63–4.00(2H,m),4.63–4.78(1H,m), 4.78–5.06(1H,m),6.18(1H,d,J=6Hz),7.63(1H, dd,J=6,1.5Hz)

In 170 ml of methanol was dissolved 15.0 g of the product obtained as above. To the solution was added 3.11 g of cerium (III) chloride. The mixture was stirred at room temperature for 45 minutes, to which was then added 1.17 g of sodium borohydride by portions, while stirring for 20 minutes. The reaction solution was concentrated under reduced pressure to about half of its original volume, to which was added a saturated aqueous saline solution, followed by extraction (twice) with ethyl acetate. The organic layer was washed with a saturated aqueous saline solution and dried (Na$_2$SO$_4$). The solvent was evaporated off, and the residue was subjected to a silica gel column chromatography, followed by elution with hexane—ethyl acetate (2:3) to give 13.2 g of 4-(2-tetrahydropyranyl)oxy-2-cyclopentenol as an oily product.

IR$\nu_{max}^{Neat}$cm$^{-1}$:3500,2950,1100
NMR(90MHz,CDCl$_3$)δ:1.33–1.87(6H,m),2.45–2.84(2H,m)3.30–3.57(1H,m),3.66–4.06(1H,m),4.48–4.75(3H,m),6.00(2H,s)

In 20 ml of tetrahydrofuran was dissolved 10.3 g of the product obtained as above. The solution was added dropwise over 3 minutes to a suspension of 3.36 g of sodium hydride (40% oily) in 100 ml of tetrahydrofuran under ice-cooling in argon streams. The mixture was stirred at room temperature for 30 minutes, followed by addition of 16 g of methyl iodide. The mixture was stirred for further 4 hours. The reaction solution was poured into water, which was subjected to extraction with diethyl ether. The organic layer was washed with an aqueous saline solution and dried (MgSO$_4$). The solvent was evaporated off, and the residue was subjected to a silica gel column chromatography, followed by elution with hexane—ethyl acetate (1:4) to give 9.7 g of 1-methoxy-4-(2-tetrahydropyranyl)oxy-2-cyclopentene as an oily product.

IR$\nu_{max}^{Neat}$cm$^{-1}$:2950,1100
NMR(90MHz,CDCl$_3$)δ:1.39–1.86(6H,m),2.46–2.89(2H,m),3.33(3H,s),3.33–3.63(1H,m),3.73–4.03(1H,m), 4.20–4.39(1H,m),4.49–4.79(2H,m),6.00(2H,s)

In 250 ml of dichloromethane was dissolved 8.0 g of the product obtained as above. Into the solution was blown ozone gas at −78° C. After one hour, nitrogen gas was introduced to purge excess ozone gas, followed by addition of 12.5 g of dimethylsulfide. The mixture was stirred at 0° C. for 2 hours. The solvent was evaporated off under reduced pressure, and the residue was dissolved in 125 ml of ethanol. To the solution was added an aqueous solution (125 ml) of 17 g of silver nitrate and 19 g of sodium hydroxide, and the mixture was stirred at room temperature for one hour. Then, precipitating crystals were filtered off, and the filtrate was neutralised with 35% hydrochloric acid, followed by concentration. The concentrate was suspended in methanol, to which was added diazomethane to cause methylation. The solvent was evaporated off, and the residue was dissolved in ethyl acetate. The organic layer was washed with water and dried (MgSO$_4$). The solvent was evaporated off, and the residue was subjected to a silica-gel column-chromatography, followed by elution with hexane—ethyl acetate (2:1) to give 7.5 g of dimethyl 2-methoxy-4-(2-tetrahydropyranyl) oxyglutarate as an oily product.

IR$\nu_{max}^{Neat}$cm$^{-1}$:2950,1740,1200
NMR(90MHz,CDCl$_3$)δ:2.21(2H,dd,J=12,3Hz),3.30, 3.36(3H,each s),3.65,3.69,3.70,3.71(6H,each s), 4.42(1H,t,J=6Hz),4.59–4.79(1H,m)

In 60 ml of methanol was dissolved 7.5 g of the product obtained as above. To the solution was added 2.5 ml of 5% hydrochloric acid. The mixture was stirred at room temperature for 30 minutes, which was neutralised with an aqueous solution of sodium hydrogencarbonate, followed by concentration under reduced pressure. The concentrate was subjected to extraction with ethyl acetate. The organic layer was washed with an aqueous saline solution, dried (Na$_2$SO$_4$), then concentrated. The concentrate was dissolved in 50 ml of acetone. To the solution was added a Jones reagent (8N solution) (until the reaction solution became orange green-colored), which was stirred at 150° C. for 15 minutes. The reaction solution was poured into water, which was then extracted with ethyl acetate. The extract was washed with an aqueous saline solution, dried (MgSO$_4$), then the solvent was evaporated off under reduced pressure. The residue was subjected to a silica gel column chromatography, followed by elution with hexane—ethyl acetate (3:2) to give 3.2 g of dimethyl 4-methoxy-2-oxoglutarate as an oily product.

IR$\nu_{max}^{Neat}$cm$^{-1}$:2950,1740
NMR(90MHz,CDCl$_3$)δ:3.25(2H,d,J=6Hz),3.43(3H,s), 3.76,3.89(3H,each s),4.29(1H,t,J=6Hz)

Then, 1.66 g of the product obtained as above was dissolved in a mixture of 30 ml of methanol and 6 ml of water. To the solution was added gradually under ice-cooling 820 g of lithium hydroxide, followed by stirring for 20 minutes. To the resultant was added 10 ml of water, which was neutralized with 35% hydrochloric acid, followed by evaporation of methanol under reduced pressure. The reaction solution was adjusted to about pH 1 with 35% hydrochloric acid, which was subjected to extraction with ethyl acetate. The organic layer was dried (MgSO$_4$), then the solvent was evaporated off to leave 1.42 g of 4-methoxy-2-oxoglutaric acid as an oily product.

IR$\nu_{max}^{Neat}$cm$^{-1}$:2950,1730,1450,1260
NMR(90MHz,d$_6$-DMSO)δ:3.28(2H,d,J=6Hz), 3.33(3H,s),4.20(1H,t,J=6Hz)

In 10 ml of N,N-dimethylformamide were dissolved 846 mg of the product obtained as above and 522 mg of dicyclohexylamine. The solution was stirred at room temperature for 30 minutes, to which was added 622 mg of 4-nitrobenzylbromide, followed by stirring at 40° C. for one hour. Precipitating crystals were filtered off. To the filtrate was added water, which was subjected to extraction with ethyl acetate. The organic layer was washed with water, dried (Na$_2$SO$_4$), followed by concentration to give 896 mg of the subject Compound (93) as an oily product.

IR$\nu_{max}^{Neat}$cm$^{-1}$:1735,1707,1530,1345,1275,1085
NMR(90MHz,CDCl$_3$)δ:3.30(2H,d,J=6Hz), 4.30(1H,t, J=6Hz),5.3(2H,s),7.6,8.2(2H,each d,J=8Hz)

EXAMPLE 94

Production of 4-nitrobenzyl 2-[(4S)-4-benzyloxycarbonylamino-3-oxo-2-isoxazolidinyl]-4-methoxy-5-oxo-2-tetrahydrofurancarboxylate [Compound (94)]:

In 10 ml of dichloromethane was dissolved 896 mg of Compound (93). To the solution were added 680 mg of (4S)-4-benzyloxycarbonylamino-3-isoxazolidinone and 593 mg of DCC, and the mixture was stirred at room temperature for one hour. Then, precipitating crystals were filtered off, and the solvent was evaporated off. The residue was subjected to a silica gel column chromatography, followed by elution with hexane—ethyl acetate (3:2) to give 723 mg of the subject Compound (94) as an oily product.

IR$\nu_{max}^{CHCl_3}$cm$^{-1}$:2930,1800,1720,1520
NMR(90MHz,CDCl$_3$)δ:3.26–3.40(1H,m),3.51, 3.56(3H,each s), 3.66–3.80(1H,m)4.-10–4.33(2H,m),4.59–4.89 (2H,m),5.10(2H,s), 5.33(2H,s),7.33(5H,s),7.50,8.23(2H,each d, J=7.5Hz)

EXAMPLE 95

Production of sodium 2-{(4S)-[2-(2-amino-4 -thiazolyl)-(Z)-2-(methoxyimino)acetamido]-3-oxo-2-isoxazolidinyl}-4-methoxy-5-oxo-2-tetrahydrofurancarboxylate [Compound (95)]:

Employing 290 mg of Compound (94), a reaction analogous to that in Example 4 was conducted to give 73 mg of the subject Compound (95) as a white powdery product.

IR$\nu_{max}^{KBr}$cm$^{-1}$:1780,1720,1660,1530,1020
NMR(100MHz,D$_2$O)δ:3.02–3.20,3.36–3.64(total 2H,m),3.38,3.58(total 3H,each s), 4.00(3H,s),7.02(1H,s)

Mass spectrum m/e:466(M$^+$+1)

EXAMPLE 96

Production of sodium 2-[(4S)-4-(2-thienylacetamido)-3-oxo-2-isoxazolidinyl]-4-methoxy-5-oxo-2-tetrahydrofurancarboxylate [Compound (96)]:

Employing 190 mg of Compound (94), a reaction analogous to that in Example 3 was conducted to give 37 mg of the subject Compound (96) as a white powdery product.

IR$\nu_{max}^{KBr}$cm$^{-1}$:1780,1720,1650,1540
NMR(90MHz,D$_2$O)δ:3.06–3.72(2H,m),3.66(2H,s), 3.46,4.00(total 3H,each s),4.17–4.56(2H,m), 4.60–5.26(2H,m),7.06–7.27(2H,m),7.43–7.56(1H,m)

Mass spectrum m/e:407(M$^+$+1)

EXAMPLE 97

Production of 1-(4-nitrobenzyl) 2-carboxy-α-oxophenylacetate [Compound (97)]:

In 10 ml of tetrahydrofuran was dissolved 388 mg of 2-carboxy-α-oxophenylacetic acid, followed by addition of 495 mg of DCC. The mixture was stirred at room temperature for 30 minutes. Resultant precipitates were filtered off. To the filtrate was added 306 mg of 4-nitrobenzyl alcohol, and the mixture was heated for 3 hours under reflux. The solvent was evaporated off, and the residue was subjected to a silica gel column chromatography, followed by elution with hexane—ethyl acetate (2:1→0:1) to give 112 mg of the subject Compound (97) as colorless crystals, m.p. 165°–167° C.

IR$\nu_{max}^{KBr}$cm$^{-1}$:3450,1760,1750,1345,1260
NMR(90MHz,CDCl$_3$)δ:5.30(2H,s),8.01–7.40(4H,m), 7.42(2H,d,J=9Hz),8.18(2H,d,J=9Hz)

EXAMPLE 98

Production of 4-nitrobenzyl 3-chloro-1,3-dihydro-1-oxoisobenzofuran-3-carboxylate [Compound (98)]:

In 15 ml of dichloroethane was dissolved 580 mg of Compound (97), followed by addition of 0.58 ml of thionyl chloride. The mixture was heated for one hour under reflux. The solvent was evaporated off, and the residue was treated with isopropylether to give 500 mg of the subject Compound (98) as colorless crystals, m.p. 132°–134° C.

IR$\nu_{max}^{KBr}$cm$^{-1}$:1795,1770,1620,1550,1265,1255,1040

EXAMPLE 99

Production of 4-nitrobenzyl 3-[(4S)-4-benzyloxycarbonylamino-3-oxo-2-isoxazolidinyl]-1,3-dihydro-1-oxoisobenzofuran-3-carboxylate [Compound (99)]:

In 5 ml of dichloromethane were dissolved 236 mg of (4S)-4-benzyloxycarbonylamino-3-isoxazolidinone and 347 mg of Compound (98). To the solution was added, under ice-cooling, 0.14 ml of triethylamine, and the mixture was stirred for 30 minutes. The solvent was evaporated off. To the residue was added ethyl acetate, which was washed with water and an aqueous saline solution. The organic layer was dried, then the solvent was evaporated off. The residue was subjected to a column chromatography using Florisil, followed by elution with hexane—ethyl acetate (2:1→1:1) to give 350 mg of the subject Compound (99) as a pale yellow oily product.

IR$\nu_{max}^{Neat}$cm$^{-1}$:3340,1785–1720,1520,1345,1250
NMR(90MHz,CDCl$_3$)δ:3.96–4.35(2H,m),4.-85–4.42(1H,m),5.10(2H,s),5.35(2H,s),5.6(1H,b),7.3-0(5H,s), 7.48(2H,d,J=9Hz),7.55–8.00(4H,m),8.19(2H,d,J=-9Hz)

Mass spectrum m/e:547(M$^+$).

EXAMPLE 100

Production os sodium 3-{(4S)-4-[2-(2-amino-4-thiazolyl)-(Z)-2-methoxyimino)acetamido]-3-oxo-2-isoxazolidinyl}-1,3-dihydro-1-oxoisobenzofuran-3-carboxylate [Compound (100)]:

In a mixture of 5 ml of ethyl acetate and 5 ml of a phosphate buffer of pH 7.0 was dissolved 350 mg of Compound (99). To the solution was added 350 mg of 10% palladium-carbon. The mixture was stirred in hydrogen streams under ice-cooling for 2 hours. The catalyst was filtered off and washed with water. The filtrate and the wasing were combined, and the aqueous layer was separated. To the aqueous layer were added 15 ml of tetrahydrofuran and 161 mg of sodium hydrogencarbonate. To the mixture was added, with stirring, 213 mg of 2-chloroacetamido-4-thiazolyl-(Z)-2-methoxyiminoacetyl chloride under ice-cooling. The stirring was further continued for 30 minutes under ice-cooling, followed by addition of 99 mg of sodium N-methyldithiocarbamate. The mixture was stirred at room temperature for one hour. The reaction mixture was washed with ether, then the aqueous layer was concentrated, and the residue was purified by means of an XAD-II column chromatography. The fractions eluted with 20% ethanol were combined and liophilized to give 65 mg of the subject Compound (100) as a white powdery product.

IR$\nu_{max}^{KBr}$cm$^{-1}$:1760,1660,1530,1385
NMR(90MHz,DMSO-d$_6$)δ:3.85(3H,s),4.70–4.20(2H,m), 4.70–5.10(1H,m),7.02(1H,s),7.1(2H,b),7.-35–7.90(4H,m),9.10(1H,d,J=8Hz)

EXAMPLE 101

Production of 1-(4-nitrobenzyl) 2-oxo-4-phenylthioglutarate [Compound (101)]:

In 35 ml of anhydrous tetrahydrofuran was dissolved 1.71 ml of diisopropylamine. To the solution was added, under nitrogen atmosphere, 7.49 ml of 1.6 M n-butyllithium (hexane solution) at −78° C. under stirring. The mixture was stirred for 15 minutes, followed by addition of 2.06 g of dimethyl 2-oxoglutarate dimethylacetal dissovled in 5 ml of anydrous tetrahydrofuran over a period of 5 minutes, and the mixture was stirred for 15 minutes.

Then, to the reaction mixture was added a solution of 2.81 g of phenyl benzenethiosulphonate and 0.81 ml of hexamethylphosphoramide in 5 ml of anhydrous tetrahydrofuran over a period of 10 minutes, followed by stirring for 30 minutes at −78° C. The reaction temperature raised to −50° C. over a period of one hour under stirring, followed by addition of a saturated aqueous solution of ammonium chloride and by extraction with ethyl acetate. The extracts was washed with water and dried ($MgSO_4$). The solvent was evaporated off, and the residue was subjected to a silica gel column chromatography, followed by elution with hexane—ethyl acetate (2:1) to give 3.02 g of dimethyl 2-xo-4-phenylthio-glutarate dimethylacetal as a pale yellow oily product.

$IR\nu_{max}^{Neat}cm^{-1}$:1740,1600

NMR(90MHz,$CDCl_3$)δ2.26(1H,dd,J=5,8Hz), 2.63(1H,dd,J=5,8Hz),3.23(6H,s),3.62(3H,s), 3.73(1H,m),3.73(3H,s),7.2–7.6(5H,m)

This product as also obtained by the above method, employing phenyl disulfide instead of phenyl benzenethiosulfonate.

In 25 ml of methanol was dissolved 3.02 g of the above product. To the solution was added 25 ml of 1.8M aqueous solution of potassium hydroxide under ice-cooling with stirring at such a rate as keeping the reaction mixture homogeneous, followed by stirring at room temperature for 3.5 hours. Methanol was evaporated off. The aqueous layer was made to pH 1 with 6N HCl, which was then saturated with sodium chloride, followed by extraction with ethyl acetate. The extracts were washed with an aqueous saline solution, dried ($MgSO_4$), and evaporated to leave 2.85 g of 2-oxo-4-phenylthio-glutaric acid dimethyl acetal as a yellow oily product. To a solution of 2.76 g of this oily product in 40 ml of tetrahydrofuran was added 40 ml of 1N hydrochloric acid. The mixture was stirred at 50° C. for 7.5 hours. Tetrahydrofuran was evaporated off and the aqueous layer was saturated with sodium chloride, followed by extraction with ethyl acetate. The extracts was washed with an aqueous saline solution, dried ($MgSO_4$), and evaporated to leave 2.25 g of 2-oxo-4-phenylthioglutaric acid as a yellow oily product. To a solution of 2.05 g of this oily product in 20 ml of dimethylformamide were added 0.96 ml of dicyclohexylamine and 1.05 g of 4-nitrobenzylbromide. The mixture was stirred for 6 hours. To the reaction solution was added ethyl acetate, and precipitating crystals were filtered off. The filtrate was washed with water, dried ($MgSO_4$), and evaporated. The residue was subjected to a silica gel column chromatography, followed by elution with hexane—ethyl acetate (3:1) to give 883 mg of the subject Compound (101) as a pale yellow oily product.

$IR\nu_{max}^{Neat}cm^{-1}$:3600–2500,1800–1700,1600

NMR(90MHz,$CDCl_3$)δ:3.03(2H,m),4.12(1H,t,J=8-Hz), 5.30(1H,m),5.33(2H,s),7.2–7.7(5H,m),7.48(2H,d,J=9Hz),8.22(2H,d,J=9Hz)

EXAMPLE 102

Production of 4-nitrobenzyl 2-{(4S)-[4-(4-nitrobenzyloxycarbonylamino)]-3-oxo-2-isoxazolidinyl}-5-oxo-4-phenylthio-2-tetrahydrofurancarboxylate [Compound (102)]:

In 4 ml of dichloromethane were suspended 180 mg of (4S)-4-(4-nitrobenzyloxycarbonylamino)-3-isoxazolidinone and 260 mg of Compound (101). To the suspension was added 206 ml of 1-ethoxycarbonyl-2-ethoxy-1,2-dihydroquinoline, and the mixture was stirred at room temperature for 3.5 hours. The solvent was evaporated off, and the residue was subjected to a silica gel column chromatography, followed by elution with hexane—ethyl acetate (2:1→1:1) to give 253 mg of the subject Compound (102) as a pale yellow oily product.

$IR\nu_{max}^{Neat}cm^{-1}$:3370,1790,1780–1700,1600,1520,1340

NMR(90MHz,$CDCl_3$)δ:2.43(1H,dd,J=9,16Hz),3.3–3.7(1H,m),4.21(2H,t,J=9Hz),4.4–5.0(2H,m),5.20(2-H,s), 5.28,5.35(total 2H,each s,2:1),5.52(1H,m), 7.2–7.7(5H,m),7.46(4H,d,J=9Hz),8.18(4H,d,J=9-Hz)

Mass spectrum m/e:652($M^+$).

EXAMPLE 103

Production of sodium 2-{(4S)-4-[2-(2-amino-4-thiazolyl)-(Z)-2-(methoxyimino)acetamido]-3-oxo-2-isoxazolidinyl}-4-phenylthio-5-oxo-2-tetrahydrofuran-carboxylate [Compound (103)]:

In a mixture of 6 ml of ethyl acetate and 9 ml of a phosphate buffer of pH 7.0 was dissolved 230 mg of Compound (102). To the solution was added 230 mg of 10% palladium-carbon. The mixture was stirred for one hour in hydrogen streams under ice-cooling and for further one hour at room temperature. The catalyst was filtered off and washed with water. The washing was combined with the filtrate, and the aquesous layer was separated. To the aqueous layer was added 11 ml of tetrahydrofuran, to which were added under ice-cooling with stirring 89 mg of sodium hydrogencarbonate and 152 mg of 2-chloroacetamido-4-thiazolyl-(Z)-2-methoxyiminoacetyl chloride hydrochloride. The reaction solution was stirred under ice-cooling for 30 minutes, followed by addition of 82 mg of sodium N-methyldithiocarbamate. The mixture was stirred at room temperature for one hour. Tetrahydrofuran was evaporated off, and the aqueous layer was washed with ethyl acetate, followed by purification by means of an HP-20 column chromatography. Fractions eluted with 10% ethanol were lyophilized to give 26 mg of the subject Compound (103) as a pale yellow powdery product.

$IR\nu_{max}^{KBr}cm^{-1}$:1780,1720,1660

NMR(90MHz,$D_2O$)δ:2.73(1H,dd,J=9,15Hz),3-.0–4.1(2H,m),4.20(2H,s),4.3–4.8(2H,m),5-.1–5.6(1H,m),7.20, 7.22(total 1H,each s),7.5–7.9(5H,m)

EXAMPLE 104

Production of 4-nitrobenzyl 2-[(4S)-4-phenylacetyamido-3-oxo-2-isoxazolidinyl]-5-oxo-3-phenylthio-2-tetrahydrofurancarboxylate [Compound (104)]:

In 5 ml of dichloromethane were suspended 227 mg of (4S)-4-phenylacetamido-3-isoxazolidinone and 405 mg of 1-4-nitrobenzyl) 2oxo-3-phenylthioglutarate. To the suspension was added a solution of 278 mg of DCC in 2.5 ml of dichloromethane. The mixture was stirred at room temperature for 1.5 hour. To the reaction solution was added ethyl acetate, and precipitating crystals were filtered off. The filtrate was washed with water, dried (MgSO$_4$), and evaporated.

The residue was subjected to a silica gel column chromatography, followed by elution with hexane—ethyl acetate (2:1→1:1) to give 288 mg of the subject Compound (104) as a pale yellow oily product.

IR$\nu_{max}^{Neat}$cm$^{-1}$:3350,1810,1760,1670,1600,1520,1350
NMR(90MHz,CDCl$_3$)δ:2.64(1H,dd,J=6,18Hz),3.22-(1H,dd,J=9,18Hz),3.60(2H,s),3.8–4.2(1H,m),4-.3–5.1(3H,m),5.2–5.5(2H,m),6.0–6.3(1H,m),7-.1–7.7(10H,m),
7.52(2H,d,J=9Hz),8.18(2H,d,J=9Hz)

EXAMPLE 105

Production of sodium 2-[(4S)-4-phenylacetylamido-3-oxo-2-isoxazolidinyl]-5-oxo-3-phenylthio-2-tetrahydrofurancarboxylate [Compound (105)]:

To a solution of 280 mg of Compound (104) in 7 ml of ethyl acetate were added 11 ml of a phosphate buffer of pH 7.0 and 280 mg of 10% palladium-carbon. The mixture was stirred for one hour in hydrogen streams under ice-cooling, and for further 30 minutes at room temperature. The catalyst was filtered off and washed with water. The washing was combined with the filtrate. The aqueous layer was separated and washed with ethyl acetate, followed by purification by means of an HP-20 column chromatography. Fractions eluted with 30% ethanol were lyophilized to give 75 mg of the subject Compound (105) as a white powdery product.

IR$\nu_{max}^{KBr}$cm$^{-1}$:1790,1720,1660
NMR(90MHz,D$_2$O)δ:2.95(1H,dd,J=6,19Hz),3.53(1H,dd,J=9,19Hz), 3.88(2H,s),4.0–5.4(4H,m), 7.4–7.9(5H,m),7.58(5H,s)

EXAMPLE 106

Production of 4-nitrobenzyl 2-chloro-phenylthio-5-oxo-2-tetrahydrofurancarboxylate [Compound (106)]:

To a solution of 315 mg of Compound (101) in 13 ml of 1,2dichloroethane was added 0.33 ml of thionyl chloride. The mixture was heated for 2 hours under reflux. The solvent was evaporated off, and the residue was subjected to a column chromatography using Florisil, followed by elution with hexane—ethyl acetate (2:1) to yield 170 mg of the subject Compound (106) as a pale brown oily product.

IR$\nu_{max}^{Neat}$cm$^{-1}$:1810,1760,1600,1520,1320
NMR(90MHz,CDCl$_3$)δ:2.83(1H,dd,J=11,15Hz),
3.14(1H,dd,J=9,15Hz),4.23(1H,dd,J=9,11Hz),
5.34(2H,s),7.2–7.7(5H,m),7.50(2H,d,J=9Hz),
8.24(2H,d,J=9Hz)
Mass spectrum m/e:409,407(M+).

EXAMPLE 107

Production of 4-nitrobenzyl 2-[(4S)-4-phenylacetamido-3-oxo-2-isoxazolidinyl]-5-oxo-4-phenylthio-2-tetrahydrofurancarboxylate [Compound (107)]:

(a) In 6 ml of dichloromethane were suspended 265 mg of (4S)-4-phenylacetamido-3-isoxazolidinone and 165 mg of 1-(4-nitrobenzyl) 2-oxo-4-phenylthioglutarate. To the suspension was added 219 mg of 1-ethoxycarbonyl-2-ethoxy-1,2-dihydroquinoline, and the mixture was stirred at room temperature for 2 hours. The solvent was evaporated off, and the residue was subjected to a silica gel column chromatography, followed by elution with hexane—ethyl acetate (2:1→1:1) to yield 200 mg of the subject Compound (107) as a colorless oily product.

IR$\nu_{max}^{Neat}$cm$^{-1}$:3350,1790,1670,1600,1520,1350
NMR(90MHz,CDCl$_3$)δ:2.40(1H,dd,J=9,15Hz),
2.7–3.5(1H,m),3.55(2H,s),3.6–4.4(2H,m),4-.5–5.0(2H,m),5.28(2H,b),6.25(1H,m),7-.1–7.7(12H,m), 8.17(2H,d,J=9Hz)

(b) In 2.5 ml of dichloromethane were dissolved 76 mg of (4S)-4-phenylacetamido-3-isoxazolidinone and 0.11 ml of triethylamine. To the solution was added under ice-cooling while stirring a solution of 155 mg of Compound (106) in 1 ml of dichloromethane. The reaction solution was stirred at room temperature for 30 minutes, followed by diluting with ethyl acetate, which was washed with water, then dried (MgSO$_4$). The solvent was evaporated off, and the residue was subjected to a silica gel column chromatography, followed by elution with hexane—ethyl acetate (2:1→1:1) to yield 56 mg of the subject Compound (107) as pale a yellow oily product. IR and NMR spectra of this product were in agreement with those of the Compound (107) obtained in (a).

EXAMPLE 108

Production of sodium 2-[(4S)-4-phenylacetamido-3-oxo-2-isoxazolizinyl]-5-oxo-4-phenylthio-2-tetrahydrofurancarboxylate [Compound (108)]:

To a solution of 250 mg of Compound (107) in 7 ml of ethyl acetate were added 10 ml of a phosphate buffer of pH 7.0 and 250 mg of 10% palladium—carbon. The mixture was stirred for one hour in hydrogen streams under ice-cooling and for further 30 minutes at room temperature. The catalyst was filtered off and washed with water. The filtrate and the washing were combined, and the aqueous layer was separated and washed with ethyl acetate, followed by purification by means of an HP-20 column chromatography. Fractions eluted with 30% ethanol were lyophilized to give 80 mg of the subject Compound (108) as a white powdery product.

IR$\nu_{max}^{KBr}$cm$^{-1}$:1790,1730,1660
NMR(90MHz,D$_2$O)δ:2.6–2.9(1H,m),3.1–3.8(1H,m),
3.86(2H,s),4.1–5.3(4H,m),7.57–7.67(10H,m)

EXAMPLE 109

Production of 4-nitrobenzyl 2-[(4S)-5-acetoxymethyl-4-tert-butoxycarbonylamino-3-oxo-2-isoxazolidinyl]-5-oxo-2-tetrahydrofurancarboxylate [Compound (109)]:

In a mixed solvent of 30 ml of tert-butanol and 60 ml of water was added 4.30 g of (2S)-2-tert-butoxycarbonylamino-3-butenoic acid which was prepared by the manner described in Journal of Organic Chemistry, 45, 4817(1980). To the mixture was added 3.75 g of O-benzylhydroxylamine hydrochloride, and then was added 4.50 g of 1-ethyl-3-(3-dimethylaminopropyl)-carbodiimide hydrochloride in five portions for 10 minutes intervals under adjusting pH to 4.2.

After stirring for 1 hour at room temperature, tert-butanol was removed by evaporation, and the residue was extracted with ether. The organic layer was washed with 1N potassium hydrogen sulfate, 0.5N sodium hydrogen carbonate, and a saturated aqueous solution of sodium chloride successively, followed by drying over MgSO$_4$. *The solvent was removed by evaporation under reduced pressure to afford* 5.12 g of (2S)-O-benzyl-2-tert-butoxycarbonylamino-3-butenohydroxamate.

IR$\nu_{max}^{KBr}$cm$^{-1}$:3330,2985,1680,1670,1528
NMR(90MHz,CDCl$_3$)δ:1.40(9H;s),4.50–4.80(1H,m), 4.90(2H,s),5.20–5.45(3H,m),5.66–6.10(1H,m), 7.35(5H,s),8.80–9.10(1H,m)

This product (2.50 g) was dissolved in 20 ml of toluene, to which was added 2.81 g of m-chloroperbenzoic acid. The mixture was stirred at 35° C. for 8 hours. The resultant was cooled to 0° C., to which was added a solution of sodium hydrogen sulfite so as to decompose the excess amount of m-chloroperbenzoic acid. To the resultant were added 50 ml of ethyl acetate and 50 ml of a solution of 0.5N sodium hydrogen carbonate, and the mixture was stirred for 1 hour. The ethyl acetate layer was recovered, the layer was washed with a solution of 0.5N sodium hydrogen carbonate and then with a saturated sodium chloride, and dried over Na$_2$SO$_4$.

The solvent was removed by evaporation under reduced pressure and the residue was subjected to flash column chromatography (silica gel), followed by elution with hexane-ether (2:3→1:2) to give diastereomer A (473 mg) and B (1.433 g) of (2S)-O-benzyl-2-tert-butoxycarbonylamino-3,4-epoxybutenohydroxamate.

(A) IR$\nu_{max}^{KBr}$cm$^{-1}$:3330,3260,1680,1670,1530
NMR(90 MHz,CDCl$_3$)δ:1.43(9H,s),2.82(2H,d,J=3Hz), 2.90–3.10(1H,dd,J=3,7.5Hz),3.75(1H,dd,J=6.6,7.5Hz),4.93(2H,s),5.60(1H,d,J=6.6Hz), 7.40(5H,s)

(B) IR$\nu_{max}^{neat}$cm$^{-1}$:3330,3250,1680,1670,1540
NMR(90MHz,CDCl$_3$)δ: 1.43(9H,s),2.53–2.83 (2H,m),3.23–3.50(1H,m),4.30–4.50(1H,bs), 4.92(2H,s),5.47(1H,d,J=8Hz),7.40(5H,s)

Thus obtained diastereomer B (914 mg) was dissolved in 15 ml of methanol. To the mixture were added 150 mg of 5% palladium-carbon and 20 mg of pyridine, and the mixture was stirred for 30 minutes at room temperature under hydrogen stream. The catalyst was removed by filtration, to the filtrate was added 184 mg of sodium methoxide, and the mixture was stirred for 4 hours at room temperature. Methanol was removed by evaporation under reduced pressure, to the residue was added 4 ml of 1N potassium hydrogen sulfate, and the mixture was extracted with a mixed solution of ethyl acetate-tert-butanol (4:1) for 4 times.

The organic layer was washed with a saturated solution of sodium chloride, and then dried over Na$_2$SO$_4$. The solvent was removed by evaporation under reduced pressure, and the residue was subjected to flash column chromatography (silica gel), followed by elution with hexane—ethyl acetate-methanol (4:8:1) to give 591 mg of (4S)-4-tertbutoxycarbonylamino-5-hydroxymethyl-3-isoxazolidinone.

IR$\nu_{max}^{KBr}$cm$^{-1}$:3360,1720,1700,1535
NMR(270MHz,CDCl$_3$)δ:1.49(9H,s),3.92(1H,dd, J=13,16Hz),4.27–4.40(1H,m),4.60–4.73(1H,m), 5.63–5.70(1H,m)

This product (116 mg) was dissolved in 1.5 ml of dichloromethane. To the solution was added 65 mg of N,N-diisopropylethylamine and then added 1.5 ml of a dichloromethane solution of 53 mg of chloromethyl methyl sulfide, and the mixture was stirred for 30 minutes. The temperature was elevated to room temperature, and the mixture was stirred overnight, and the excess amount of chloromethyl methyl sulfide was removed by evaporation. The residue was dissolved in ethyl acetate, and the organic layer was washed with water and then a saturated aqueous solution of sodium chloride, and then dried over Na$_2$SO$_4$. The residue was subjected to flash column chromatography using silica gel, followed by elution with hexane—ethyl acetate (5:6) to give 55 mg of (4S)-4-tertbutoxycarbonylamino-5-hydroxymethyl-2-methylthiomethyl-3-isoxazolidinone.

IR$\nu_{max}^{KBr}$cm$^{-1}$:3360,1715,1655,1530
NMR(90MHz,CDCl$_3$)δ:1.46(9H,s),2.25(3H,s), 3.40–3.65(1H,bs),3.85–4.05(2H,m),4.17–4.40 (1H,m),4.63(1H,dd,J=6,12Hz),5.43(1H,d, J=6Hz)

This product (55 mg) was dissolved in 1 ml of dichloromethane. To the solution was added 101 mg of triethylamine and 102 mg of acetic anhydride. The mixture was stirred for 1 hour at room temperature. The solvent was removed by evaporation under reduced pressure, and the residue was subjected to thin layer chromatography using silica gel, and developed with hexane—ethyl acetate (3:2), whereby 43 mg of (4S)-5-acetoxymethyl-4-tertbutoxycarbonylamino-2-methylthiomethyl-3-isoxazolidinone was obtained.

NMR(90 MHz,CDCl$_3$)δ:1.47(9H,s),2.13(3H,s), 2.27(3H,s),4.23–4.75(4H,m),4.67(2H,s), 5.30(1H,d,J=4Hz)

To the tetrahydrofuran-water solution (0.5 ml) of this product (33 mg) were added 2.6-lutidine and 85 mg of silver nitrate, and the mixture was stirred for 2 hours at room temperature. The reaction mixture was extracted with ethyl acetate. The organic layer was washed with saturated cupper sulfate solution (three times) and then with saturated sodium chloride solution, and dried over Na$_2$SO$_4$. The solvent was removed by evaporation under reduced pressure. The residue was subjected to thin layer chromatography using silica gel [developping solvent: hexane—ethyl acetate (2:3)], whereby 20 mg of a mixture of (4S)-5-acetoxymethyl-4-tert-butoxycarbonylamino-2-hydroxymethyl-3-isoxazolidinone and (4S)-5-acetoxymethyl-4-tert-butoxycarbonylamino-3-isoxazolidinone was obtained.

To this product were added 1 ml of ehtanol and 1 ml of a saturated sodium hydrogen sulfite solution, and the mixture was stirred for 3 hours at room temperature. The precipitate was removed by filtration and the filtrate was extracted with ethyl acetate-tert-butanol (4:1). The organic layer was washed with a saturated sodium chloride solution, and dried over Na$_2$SO$_4$, and then the solvent was removed by evaporation. To the residue was added chloroform, the precipitate was removed by filtration, and then the filtrate was concentrated under reduced pressure, whereby 15 mg of (4S)-5-acetoxymethyl-4-tert-butoxycarbonylamino-3-isoxazolidinone was obtained.

IR$\nu_{max}^{CH_2Cl_2}$cm$^{-1}$:3380,2920,1735,1720,1500
NMR(90MHz,CDCl$_3$)δ:1.47(9H,s),2.10(3H,s), 4.20–4.70(4H,m),5.13–5.45(1H,bs)

This product (10 mg) was dissolved in 1 ml of dichloromethane. To the solution were added 15 mg of 1-(4-nitrobenzyl) 2-oxoglutarate and 11 mg of DCC at 0° C., and the mixture was stirred.

After 5 minutes, the temperature of the reaction system was elevated to room temperature, and the mixture was stirred for 40 minutes. The precipitate was removed by filtration, and the filtrate was concentrated under reduced pressure. The residue was subjected to purification by thin layer chromatography using silica gel [developing solvent: hexane—ethyl acetate (2:1)], whereby 10 mg of the subject Compound (109) was obtained.

IR$\nu_{max}^{CH_2Cl_2}$cm$^{-1}$:3430,2920,1805,1745,1720,1600,1520,1500

NMR(90MHz,CDCl$_3$)δ:1.43(9H,s),2.10(3H,s), 2.30–3.20(4H,m),3.95–4.85(4H,m),5.05(1H,d, J=6Hz),5.37(2H,s),7.57(2H,d,J=9Hz), 8.23(2H,d,J=9Hz)

What we claim is:

1. A compound of the formula

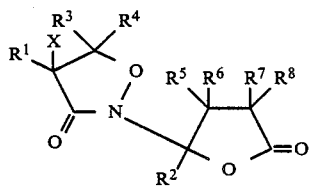

wherein R$^1$ is
(1) R$^{13}$—CO—NR$^{14}$— wherein R$^{13}$ is (a) C$_{2-6}$ alkenyl, (b) C$_{3-8}$ cycloalkyl, (c) phenyl, (d) a heterocyclic group selected from the group consisting of 2-pyridyl, 3-pyridyl, 4-pyridyl, pyrimidinyl, pyrazinyl, pyridazinyl, piperazinyl, piperidyl, pyrazolyl, pyranyl, thiopyranyl, pyrimidyl, imidazolyl, thiazolyl, isothiazolyl, oxazolyl, isoxazolyl, pyridopyrimidyl, benzopyranyl, 1,8-naphthylidyl, 1,5-naphthylidyl, 1,6-naphthylidyl, 1,7-naphthylidyl, 2,7-naphthylidyl, 2,6-naphthylidyl, quinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, hexahydro-1H-azepinyl, indolyl, isoindolyl and chromanyl, (e) C$_{1-6}$ alkoxy or (f) phenyloxy, and R$^{14}$ is hydrogen or C$_{1-6}$ alkyl;
(2) R$^{15}$NHCHR$^{16}$—CO—NH— wherein R$^{15}$ is (a) hydrogen, or (b) a group of the formula R$^{17}$—(CH$_2$)$_n$—C(=Z)— wherein R$^{17}$ is (a) C$_{1-6}$ alkoxy or (b) amino, n is 0, 1 or 2 and Z is O or S, and R$^{16}$ is C$_{1-6}$ alkyl;
(3) R$^{18}$—R$^{19}$—CO—NH— wherein R$^{18}$ is a group of the formula:

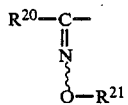

wherein R$^{20}$ is C$_{1-6}$ alkyl or a heterocyclic group selected from the group consisting of 2-pyridyl, 3-pyridyl, 4-pyridyl, pyrimidinyl, pyrazinyl, pyridazinyl, piperazinyl, piperidyl, pyrazolyl, pyranyl, thiopyranyl, pyrimidyl, imidazolyl, thiazolyl "which is unsubstituted or substituted by amino which is unprotected or is protected with halogeno acytyl", isothiazolyl, oxazolyl, isoxazolyl, pyridopyrimidyl, benzopyranyl, 1,8-naphthylidyl, 1,5-naphthylidyl, 1,6-naphthylidyl, 1,7-naphthylidyl, 2,7-naphthylidyl, 2,6-naphthylidyl, quinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, hexahydro-1H-azepinyl, indolyl, isoindolyl and chromanyl, R$^{21}$ is hydrogen or C$_{1-6}$ alkyl, R$^{19}$ is a chemical bond or a group of the formula: —CO—NH—CHR$^{24}$— wherein R$^{24}$ is C$_{1-6}$alkyl or phenyl;
(4) R$^{25}$—CHR$^{26}$—CO—NH— wherein R$^{25}$ is phenyl, and R$^{26}$ is hydroxy, sulfamoyl, sulfo, sulfoxy or C$_{1-6}$acyloxy;
(5) R$^{27}$—R$^{28}$—CH$_2$—CO—NH— wherein R$^{27}$ is (a) C$_{1-6}$ alkyl, (b) cyano, (c) phenyl, (d) phenoxy, (e) C$_{2-6}$ alkylene, (f) a heterocyclic group selected from the group consisting of 2-pyridyl, 3-pyridyl, 4-pyridyl, pyrimidinyl, pyrazinyl, pyridazinyl, piperazinyl, piperidyl, pyrazolyl, pyranyl, thiopyranyl, pyrimidyl, imidazolyl, thiazolyl, isothiazolyl, oxazolyl, isoxazolyl, pyrido[2,3-d]pyrimidyl, benzopyranyl, 1,8-naphthylidyl, 1,5-naphthylidyl, 1,6-naphthylidyl, 1,7-naphthylidyl, 2,7-naphthylidyl, 2,6-naphthylidyl, quinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl,hexahydro-1H-azepinyl, indolyl, isoindolyl and chromanyl, or (g) a group of the formula: R$^{27'}$—C(=S)— wherein R$^{27'}$is C$_{1-6}$ alkoxy, and R$^{28}$ is a chemical bond or a sulfur atom;
(6) R$^{29}$R$^{30}$N—C(=Z)—NH— wherein R$^{29}$ and R$^{30}$ are independently (a) hydrogen, (b) C$_{1-6}$ alkyl, (c) phenyl, or (d) C$_{3-8}$ cycloalkyl and Z is oxygen or sulfur atom;
(7) R$^{31}$—NH— wherein R$^{31}$ is C$_{1-6}$ alkyl, phenyl or C$_{1-6}$ alkenyl;
(8) R$^{32}$R$^{33}$N— wherein R$^{32}$ and R$^{33}$ are independently C$_{1-6}$ alkyl, phenyl or C$_{1-6}$ alkenyl;
(9) R$^{34}$R$^{35}$R$^{36}$N$^{⊕}$— wherein R$^{34}$, R$^{35}$ and R$^{36}$ are independently C$_{1-6}$ alkyl, phenyl or C$_{1-6}$ alkenyl;
(10) R$^{37}$R$^{38}$C=N— wherein R$^{37}$ and R$^{38}$ are independently hydrogen, C$_{1-6}$ alkyl, phenyl, C$_{3-8}$ cycloalkyl or amino;
(11) R$^{39}$—SOn—NH — wherein R$^{39}$ is C$_{1-6}$ alkyl or phenyl and n is 0, 1 or 2;
(12) R$^{40}$R$^{41}$R$^{42}$Si—NR$^{43}$— wherein R$^{40}$, R$^{41}$ and R$^{42}$ are independently C$_{1-6}$ alkyl or phenyl and R$^{43}$ is hydrogen or silyl;
(13) R$^{44}$R$^{45}$P(=O)—NH— wherein R$^{44}$ and R$^{45}$ are independently C$_{1-6}$ alkyl, phenyl, C$_{1-6}$ alkoxy or phenoxy; or
(14) R$^{46}$—CO—CO—NH— wherein R$^{46}$ is hydrogen, C$_{1-6}$ alkyl, C$_{1-6}$ alkoxy, phenyl, phenoxy or amino;

R$^2$ is carboxy which may be esterified or amidated;
R$^3$ and R$^4$ are independently hydrogen, C$_{1-6}$ alkyl which may be substituted, C$_{1-3}$ acyloxy, phenyl or carboxy which may be esterified or amidated;
R$^5$, R$^6$, R$^7$ and R$^8$ are independently hydrogen, C$_{1-6}$ alkyl, phenyl or benzyl which may be substituted with C$_{1-6}$ acylamino or C$_{1-6}$ alkoxy and which may be bonded through an oxygen or a sulfur atom, or R$^5$ and R$^6$ forms with R$^7$ or R$^8$ a chemical bond to form a double bond or R$^5$ or R$^6$ with R$^6$ or R$^7$ form a phenyl ring; X is hydrogen, methoxy or formylamino; provided that all of R$^3$, R$^4$, R$^5$, R$^6$, R$^7$ and R$^8$ are not hydrogen simultaneously, or a pharmaceutically acceptable salt thereof.

2. A compound as claimed in claim 1, wherein R$^1$ is
(1) R$^{13}$—CO—NR$^{14}$— wherein R$^{13}$ is C$_{1-6}$ alkoxy which is unsubstituted or is substituted by phenyl and R$^{14}$ is hydrogen;
(2) R$^{15}$NHCHR$^{16}$—CO—NH— wherein R$^{15}$ is hydrogen and R$^{16}$ is C$_{1-6}$ alkyl which is unsubstituted or is substituted by hydroxy or amino;

(3) R$^{18}$—R$^{19}$—CONH— wherein R$^{18}$ is a group of the formula

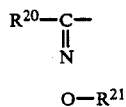

wherein R$^{20}$ is (a) a heterocyclic group selected from the group consistging of 2-pyridyl, 3-pyridyl, 4-pyridyl, pyrimidinyl, pyrazinyl, pyridazinyl, piperazinyl, piperidyl, pyrazolyl, pyranyl, thiopyranyl, pyrimidyl, imidazolyl, thiazolyl "which is unsubstituted or substituted by amino which is unprotected or is protected with halogeno acytyl", isothiazolyl, oxazolyl, isoxazolyl, pyrido[2,3-d]pyrimidyl, benzopyranyl, 1,8-naphthylidyl, 1,5-naphthylidyl, 1,6-naphthylidyl, 1,7-naphthylidyl, 2,7-naphthylidyl, 2,6naphthylidyl, quinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, hexahydro-1H-azepinyl, indolyl, isoindolyl and chromanyl, or (b) phenyl which is unsubstituted or is substituted by amino or nitro, R$^{21}$ is hydrogen or C$_{1-6}$ alkyl which is unsubstituted or is substituted by carboxy and R$^{19}$ is a chemical bond;

(4) R$^{25}$CHR$^{26}$—CONH— wherein R$^{25}$ is phenyl or cyclohexenyl and R$^{26}$ is hydroxy or sulfoxy, or (5) R$^{27}$—R$^{28}$—CH$_2$—CONH— wherein R$^{27}$ is C$_{1-6}$ alkyl, cyano, phenyl or a heterocyclic group selected from the group consisting of 2-pyridyl, 3-pyridyl, 4-pyridyl, pyrimidinyl, pyrazinyl, pyridazinyl, piperazinyl, piperidyl, pyrazolyl, pyranyl, thiopyranyl, pyrimidyl, imidazolyl, thiazolyl, isothiazolyl, oxazolyl, isoxazolyl, pyrido[2,3-d]pyrimidyl, benzopyranyl, 1,8-naphthylidyl, 1,5-naphthylidyl, 1,6-naphthylidyl, 1,7-naphthylidyl, 2,7-naphthylidyl, 2,6-naphthylidyl, uinolyl, thieno[2,3-b]pyridyl, tetrazolyl, thiadiazolyl, oxadiazolyl, triazinyl, triazolyl, thienyl, pyrrolyl, furyl, pyrrolidinyl, imidazolidinyl, dithiethane, tetrahydropyranyl, tetrahydrofuranyl, benzothienyl, hexahydro-1H-azepinyl, indolyl, isoindolyl and chromanyl, said heterocyclic groups being unsubstituted or substituted by amino or nitro and R$^{28}$ is a chemical bond.

3. A compound as claimed in claim 2, wherein the group of the formula: R$^{13}$—CO—NR$^{14}$— is C$_{1-6}$ alkoxycarbonylamino or benzyloxycarbonylamino which is unsubstituted or is substituted by nitro.

4. A compound is claimed in claim 2, wherein the group of the formula: R$^{18}$—R$^{19}$—CONH— is a group of the formula

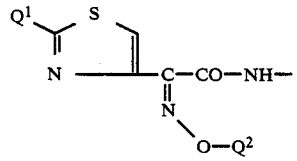

wherein Q$^1$ is amino which is unprotected or is protected with halogeno acetyl and Q$^2$ is C$_{1-3}$ alkyl or —C(CH$_3$)$_2$COOH.

5. A compound as claimed in claim 2, wherein the group of the formula: R$^{27}$—R$^{28}$—CH$_2$—CO—NH— is thienylacetamido or phenylacetamido.

6. A compound as claimed in claim 1, wherein R$^2$ is carboxy.

7. A compound as claimed in claim 1, wherein R$^2$ is a carboxy ester.

8. A compound as claimed in claim 7, wherein the carboxy ester is p-nitrobenzyl, methyl, diphenylmethyl or pivaloyloxymethyl ester.

9. A compound as claimed in claim 1, wherein R$^2$ is a carboxyamide.

10. A compound as claimed in claim 9, wherein the carboxyamide is phenylamide, propylamide or pyrrolidineamide.

11. A compound as claimed in claim 1, wherein one of R$^3$ and R$^4$ is C$_{1-3}$ alkyl, phenyl or carboxy which is free or is esterified or amidated and the other is hydrogen.

12. A compound as claimed in claim 11, wherein R$^3$ is methyl, phenyl, methoxycarbonyl or carboxamide and R$^4$ is hydrogen.

13. A compound as claimed in claim 1, wherein R$^5$ and R$^7$ are hydrogen, C$_1$-alkyl which is unsubstituted or bears a substituent, C$_{1-6}$ alkylthio or phenylthio, respectively, R$^6$ is hydrogen or C$_{1-6}$ alkyl and R$^8$ is hydrogen.

14. A compound as claimed in claim 13, wherein R$^5$ is methyl, ethylthio, acetylaminoethylthio or phenylthio, R$^6$ is hydrogen or methyl, and R$^7$ and R$^8$ are hydrogen.

15. A compound as claimed in claim 14, wherein R$^5$ and R$^6$ are methyl.

16. A compound as claimed in claim 13, wherein R$^5$, R$^6$ and R$^8$ are hydrogen and R$^7$ is methyl, methoxymethyl, benzyl, phenyl or phenylthio.

17. A compound as claimed in claim 1, wherein the compound is sodium 2-[(4S,5R)-4-(2-thienylacetamido)-5-methyl-3-oxo-2-isoxazolidinyl]-5-oxo-2-tetrahydrofurancarboxylate.

18. A compound as claimed in claim 1, wherein the compound is sodium 2-{(4S,5R)-4-[2-(2-amino-4-thiazolyl)-(Z)-2-(methoxyimino)acetamido]-5-methyl-3-oxo-2-isoxazolidinyl}-5-oxo-2-tetrahydrofurancarboxylate.

19. A compound as claimed in claim 1, wherein the compound is sodium 2-{(4S,5S)-4-[2-(2-amino-4-thiazolyl)-(Z)-2-(methoxyimino)acetamido]-5-methyl-3-oxo-2-isoxazolidinyl}-5-oxo-2-tetrahydrofurancarboxylate.

20. A compound as claimed in claim 1, wherein the compound is sodium 2-{(4R)-4-[2-(2-amino-4-thiazolyl)-(Z)-2-(methoxyimino)acetamido]-3-oxo-2-isoxazolidinyl}-5-oxo-2-tetrahydrofurancarboxylate.

21. A compound as claimed in claim 1, wherein the compound is sodium 2-{(4S)-4-[2-(2-amino-4-thiazolyl)-(Z)-2-(methoxyimino)acetamido]-3-oxo-2-isoxazolidinyl}-4-methyl-5-oxo-2-tetrahydrofurancarboxylate.

22. A compound as claimed in claim 1, wherein the compound is sodium 2-{(4S)-4-[2-(2-amino-4-thiazolyl)-(Z)-2-(methoxyimino)acetamido]-3-oxo-2-isoxazolidinyl}-3-ethylthio-5-oxo-2-tetrahydrofurancarboxylate.

23. A compound as claimed in claim 1, wherein the compound is sodium 2-{(4S)-4-[2-(2-amino-4-thiazolyl)-(Z)-2-(methoxyimino)acetamido]-3-oxo-2-isoxazolidinyl}-4-phenyl-5-oxo-2-tetrahydrofurancarboxylate.

24. A compound as claimed in claim 1, wherein the compound is sodium 2-{(4S)-4-[2-(2-amino-4-thiazolyl)-(Z)-2-(methoxyimino)acetamido]-3-oxo-2-isoxazolidinyl}-3,3-dimethyl-5-oxo-2-tetrahydrofurancarboxylate.

25. A compound as claimed in claim 1, wherein the compound is sodium 2-[(4S)-4-phenylacetamido-3-oxo-2-isoxazolidinyl]-3-(2-acetamidoethylthio)-5-oxo-2-tetrahydrofurancarboxylate.

26. A compound as claimed in claim 1, wherein the compound is sodium 2-{(4S)-4-[2-(2-amino-4-thiazolyl)-(Z)-2-(methoxyimino)acetamido]-3-oxo-2-isoxazolidinyl}-4-benzyl-5-oxo-2-tetrahydrofurancarboxylate.

27. A compound as claimed in claim 1, wherein the compound is sodium 2-{(4S)-4-[2-(2-amino-4-thiazolyl)-(Z)-2-(methoxyimino)acetamido]-3-oxo-2-isoxazolidinyl}4-methoxymethyl-5-oxo-2-tetrahydrofurancarboxylate.

28. A pharmaceutical composition for inhibiting the growth of microorganisms, which contains an effective amount for inhibiting the growth of microorganisms of a compound as claimed in claim 1 or a pharmaceutically acceptable salt thereof and a pharmaceutically acceptable carrier therefor.

* * * * *